(12) United States Patent
Han et al.

(10) Patent No.: US 9,493,704 B2
(45) Date of Patent: Nov. 15, 2016

(54) CYCLOHEPTANE DERIVATIVE AND PREPARATION METHOD AND USE THEREOF

(71) Applicant: SHIJIAZHUANG CHENGZHI YONGHUA DISPLAY MATERIALS CO., LTD., Shijiazhuang, Hebei (CN)

(72) Inventors: Yaohua Han, Shijiazhuang (CN); Zhiguo Xia, Shijiazhuang (CN); Ruimao Hua, Shijiazhuang (CN); Zengjia Yang, Shijiazhuang (CN); Kui Wang, Shijiazhuang (CN); Hongfeng Li, Shijiazhuang (CN); Jianli Zhang, Shijiazhuang (CN)

(73) Assignee: Shijiazhuang Chengzhi Yonghua Display Materials Co., Ltd., Shijiazhuang (CN)

( * ) Notice: Subject to any disclaimer, the term of this patent is extended or adjusted under 35 U.S.C. 154(b) by 0 days.

(21) Appl. No.: 14/430,536

(22) PCT Filed: Sep. 17, 2013

(86) PCT No.: PCT/CN2013/001101
§ 371 (c)(1),
(2) Date: Mar. 23, 2015

(87) PCT Pub. No.: WO2014/044021
PCT Pub. Date: Mar. 27, 2014

(65) Prior Publication Data
US 2015/0252261 A1    Sep. 10, 2015

(30) Foreign Application Priority Data

Sep. 24, 2012 (CN) .......................... 2012 1 0359003

(51) Int. Cl.
| | | |
|---|---|---|
| *C09K 19/30* | (2006.01) | |
| *C09K 19/20* | (2006.01) | |
| *C09K 19/32* | (2006.01) | |
| *C07C 43/29* | (2006.01) | |
| *C07C 43/247* | (2006.01) | |
| *C09K 19/02* | (2006.01) | |
| *C09K 19/04* | (2006.01) | |
| *C09K 19/34* | (2006.01) | |

(52) U.S. Cl.
CPC ......... *C09K 19/3068* (2013.01); *C07C 43/247* (2013.01); *C07C 43/29* (2013.01); *C09K 19/0208* (2013.01); *C09K 19/20* (2013.01); *C09K 19/30* (2013.01); *C09K 19/3066* (2013.01); *C09K 19/321* (2013.01); *C07C 2101/14* (2013.01); *C07C 2101/18* (2013.01); *C09K 2019/0466* (2013.01); *C09K 2019/301* (2013.01); *C09K 2019/3004* (2013.01); *C09K 2019/3009* (2013.01); *C09K 2019/3016* (2013.01); *C09K 2019/3019* (2013.01); *C09K 2019/3021* (2013.01); *C09K 2019/3025* (2013.01); *C09K 2019/3027* (2013.01); *C09K 2019/3037* (2013.01); *C09K 2019/3077* (2013.01); *C09K 2019/3096* (2013.01); *C09K 2019/3422* (2013.01)

(58) Field of Classification Search
CPC  C09K 19/30; C09K 19/321; C09K 19/3066; C09K 19/0208; C09K 19/20; C09K 19/3068; C09K 2019/0466; C09K 2019/3422; C09K 2019/3077; C09K 2019/3096; C09K 2019/3004; C09K 2019/3009; C09K 2019/3016; C09K 2019/3019; C09K 2019/3021; C09K 2019/3025; C09K 2019/3027; C09K 2019/3037; C09K 2019/301; C07C 43/247; C07C 43/29; C07C 2101/14; C07C 2101/18
See application file for complete search history.

(56) References Cited

U.S. PATENT DOCUMENTS

| | | | | |
|---|---|---|---|---|
| 5,792,386 | A | 8/1998 | Matsui et al. | |
| 8,405,799 | B2 * | 3/2013 | Fujisawa | C09K 19/3852 252/299.01 |
| 8,641,923 | B2 * | 2/2014 | Lee | C08F 2/48 252/299.01 |
| 8,685,274 | B2 * | 4/2014 | Masukawa | C07D 307/10 252/299.01 |

FOREIGN PATENT DOCUMENTS

| | | |
|---|---|---|
| CN | 101544893 A | 9/2009 |
| CN | 101544894 A | 9/2009 |

OTHER PUBLICATIONS

ISA State Intellectual Property Office of the People's Republic of China, International Search Report Issued in Chinese Patent Application No. PCT/CN2013/001101, Dec. 26, 2013, WIPO, 4 pages.

* cited by examiner

*Primary Examiner* — Shean C Wu
(74) *Attorney, Agent, or Firm* — Alleman Hall McCoy Russell & Tuttle LLP

(57) ABSTRACT

A cycloheptane derivative as represented by formula (I), and preparation method and use thereof; the compound has photostability and thermostability, wide nematic phase and liquid crystalline state temperature range, and good low-temperature intersolubility, and particularly has low rotary viscosity $\gamma_1$ and good dielectric anisotropy ($\Delta\epsilon>0$).

(I)

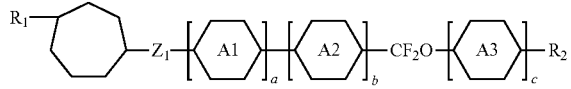

9 Claims, 6 Drawing Sheets

CYCLOHEPTANE DERIVATIVE AND PREPARATION METHOD AND USE THEREOF

CROSS REFERENCE TO RELATED APPLICATIONS

The present application is a U.S. National Phase of International Patent Application Serial No. PCT/CN2013/001101, entitled "CYCLOHEPTANE DERIVATIVE AND PREPARATION METHOD AND USE THEREOF," filed on Sep. 17, 2013, which claims priority to Chinese Application No. 201210359003.5, filed on Sep. 24, 2012, the entire contents of which are hereby incorporated by reference for all purposes.

TECHNICAL FIELD OF THE INVENTION

The present invention belongs to field of synthesis and application of a liquid crystal compound and relates to a cycloheptane derivative and preparation method and use thereof.

BACKGROUND OF THE INVENTION

A liquid crystal display using a liquid crystal composition has been widely used in instruments, computers, televisions and other displays. As for the field of liquid crystal display technology, in recent years, although the market has been a very great and the technology is increasing developed, there is an increasing requirement for display technology, particularly with respect to fast response, reduction in driving voltage and lowering the power consumption and so on. As one of important optoelectronic materials of the liquid crystal display, liquid crystal materials play an important role in improving the performance of the liquid crystal display.

According to display mode, the liquid crystal display devices are classed into following modes: a twisted nematic (TN) mode, a super twisted nematic (STN) mode, an in-plane switching (IPS) mode, a vertical alignment (VA) mode. Regardless of any of the display modes, the liquid crystal composition needs to have following characteristics.

(1) stable chemical, physical properties;
(2) low viscosity;
(3) suitable Δ∈;
(4) suitable refractive index Δn;
(5) better compatibility with other liquid crystal compounds.

The liquid crystal materials used for display has been developed greatly, and there has been a lot of liquid crystal compounds. The compounds were developed from biphenyl nitrile, ester, oxygen-containing heterocyclic compounds, and pyrimidine ring liquid crystalline compound to cyclohexylbenzenes, phenylacetylenes, ethyl bridging type, end-alkenyl liquid crystals and various fluorinated aromatic liquid crystalline compounds and so on, and the display performance requirements for example TN, STN, TFT-LCD and the like are satisfied.

Any liquid crystal compositions for display need to have a broader liquid crystalline temperature, a higher stability, a suitable viscosity, a faster response speed to electric fields. To date, however, no a single crystal monomer can be used alone in the liquid crystal display to meet the performance requirements without combination with other compounds.

SUMMARY OF THE INVENTION

An object of the present invention is to provide a cycloheptane derivative and a method for preparing the same as well as its use.

The general structural formula of cycloheptane derivative of the present invention is shown in formula I,

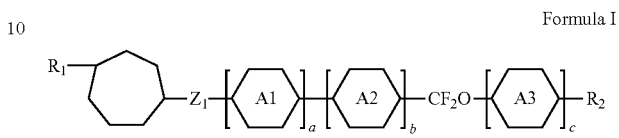

Formula I

In the formula I, both $R_1$ and $R_2$ are represented as groups shown in A, B or C:

A. at least one of H, —Cl, —F, —CN, —OCN, —OCF$_3$, —CF$_3$, —CHF$_2$, —CH$_2$F, —OCHF$_2$, —SCN, —NCS, —SF$_5$, C1-C15 alkyl, C1-C15 alkoxy, C2-C15 alkenyl and C2-C15 alkenoxy;

B. groups obtained by substituting one or at least two non-adjacent —CH$_2$— in A groups with at least one of following groups and to which oxygen atoms are not directly attached: —CH═CH—, —CC—, —COO—, —OOC—, cyclobutyl, —O— or —S—;

C. at least one of groups obtained by substituting at least one of hydrogen in A groups and B groups with fluorine or chlorine;

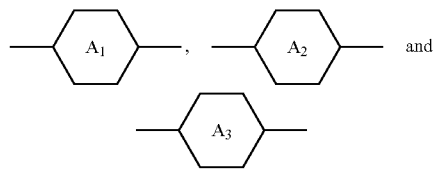

are a single bond or at least one of following groups:

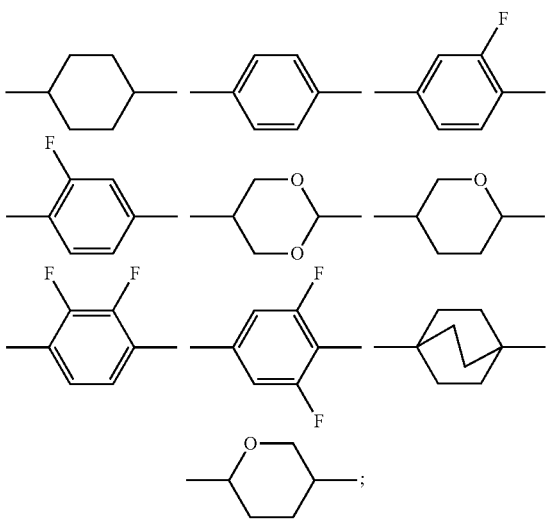

$Z_1$ is selected from at least one of a single bond, —CH$_2$—, —CH$_2$—CH$_2$—, —(CH$_2$)$_3$—, —(CH$_2$)$_4$—, —CH═CH—, —CC—, —COO—, —OOC—, —CF$_2$O—, —OCH$_2$—, —CH$_2$O—, —OCF$_2$—, —CF$_2$CH$_2$—, —CH$_2$CF$_2$—, —C$_2$F$_4$— and —CF═CF—;

a, b and c are all integer from 0 to 3, and a+b+c≤5;

when a, b and c represents 2 or 3 respectively, the groups represented by

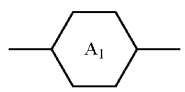

can be same or different, the groups represented by

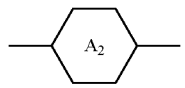

can be same or different, and the groups represented by

can be same or different.

In the above formula I, the C1-C15 alkyl is particularly selected from at least one of C2-C15 alkyl, C3-C15 alkyl, C4-C15 alkyl, C5-C15 alkyl, C6-C15 alkyl, C1-C6 alkyl, C2-C6 alkyl, C3-C6 alkyl, C4-C6 alkyl, C5-C6 alkyl, C1-C5 alkyl, C2-C5 alkyl, C3-C5 alkyl, C4-C5 alkyl, C1-C4 alkyl, C2-C4 alkyl, C3-C4 alkyl, C1-C3 alkyl, C1-C10 alkyl, C2-C10 alkyl, C3-C10 alkyl, C1-C10 alkyl, C1-C2 alkyl and C2-C3 alkyl;

The C1-C15 alkoxy is particularly selected from at least one of C2-C15 alkoxy, C3-C15 alkoxy, C4-C15 alkoxy, C5-C15 alkoxy, C6-C15 alkoxy, C1-C6 alkoxy, C2-C6 alkoxy, C3-C6 alkoxy, C4-C6 alkoxy, C5-C6 alkoxy, C1-C5 alkoxy, C2-C5 alkoxy, C3-C5 alkoxy, C4-C5 alkoxy, C1-C4 alkoxy, C2-C4 alkoxy, C3-C4 alkoxy, C1-C3 alkoxy, C1-C10 alkoxy, C2-C10 alkoxy, C3-C10 alkoxy, C1-C10 alkoxy, C1-C2 alkoxy and C2-C3 alkoxy;

The C2-C15 alkenyl is particularly selected from at least one of C3-C15 alkenyl, C4-C15 alkenyl, C5-C15 alkenyl, C6-C15 alkenyl, C1-C6 alkenyl, C2-C6 alkenyl, C3-C6 alkenyl, C4-C6 alkenyl, C5-C6 alkenyl, C2-C5 alkenyl, C3-C5 alkenyl, C4-C5 alkenyl, C2-C4 alkenyl, C3-C4 alkenyl, C2-C10 alkenyl, C3-C10 alkenyl, C2-C8 alkenyl and C2-C3 alkenyl;

The C2-C15 alkenoxy is particularly selected from at least one of C3-C15 alkenoxy, C4-C15 alkenoxy, C5-C15 alkenoxy, C6-C15 alkenoxy, C2-C6 alkenoxy, C3-C6 alkenoxy, C4-C6 alkenoxy, C5-C6 alkenoxy, C2-C5 alkenoxy, C3-C5 alkenoxy, C4-C5 alkenoxy, C2-C4 alkenoxy, C3-C4 alkenoxy, C2-C10 alkenoxy, C3-C10 alkenoxy, C2-C8 alkenoxy and C2-C3 alkenoxy;

In particular, the compound shown in formula I is a compound shown in formula I1, Formula I1

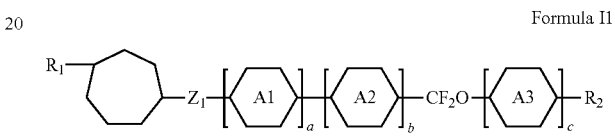

In the formula I1, the definitions of $R_1$, $R_2$, $Z_1$, a, b, c,

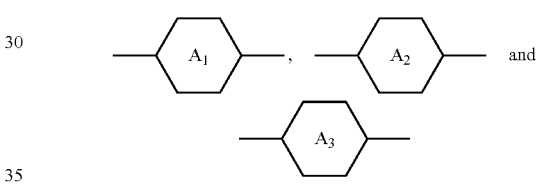

are the same as those as defined for the preceding formula I.

More specifically, the compound shown in the formula I is any one of the compounds as shown in the following formula I-1 to formula I-6:

Formula I-1

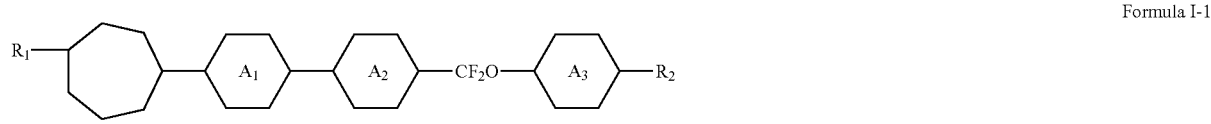

Formula I-2

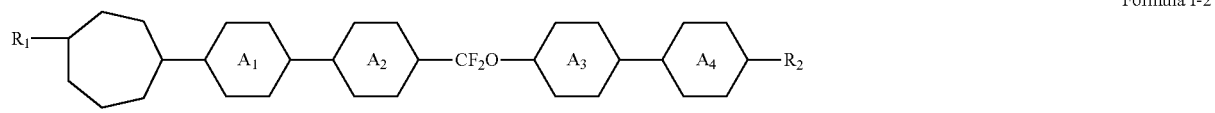

Formula I-3 Formula I-4

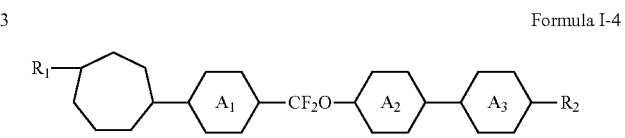

Formula I-5

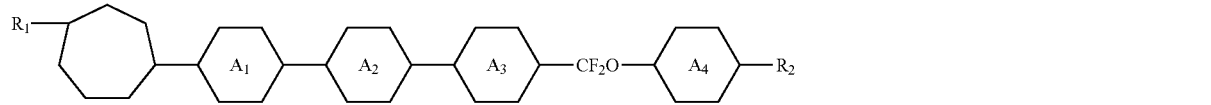

-continued

Formula I-6

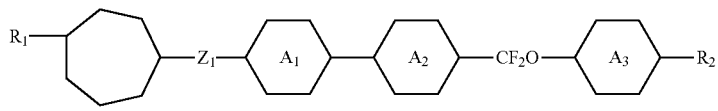

Wherein, the compound shown in the formula I-1 is more specifically the compound as shown in formula I-7, I-8, or I-17, Formula I-7

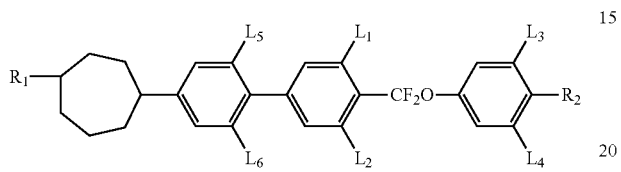

Formula I-8

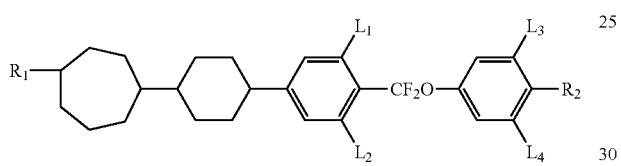

Wherein, the compound shown in the formula I-7 is more specifically the compound as shown in formula I-17, Formula I-17

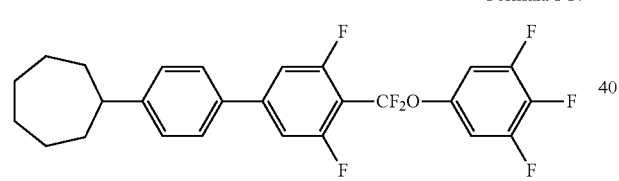

The compound shown in the formula I-2 is specifically the compound as shown in formula I-9 or formula I-10, The compound shown in the formula I-3 is specifically the compound as shown in formula I-11 or formula I-12, Formula I-11

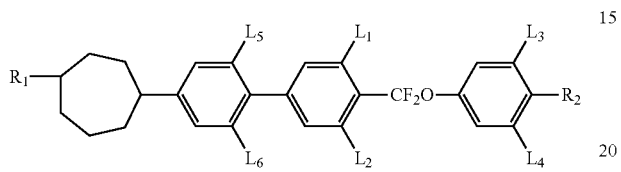

Formula I-12

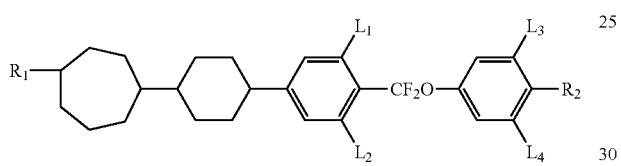

Wherein, the compound shown in the formula I-11 is more specifically the compound as shown in formula I-18, Formula I-18

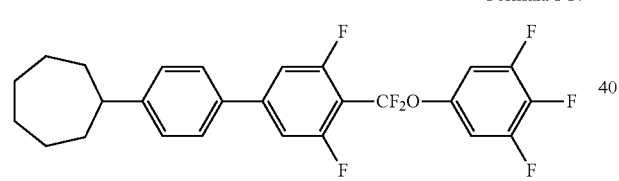

The compound shown in the formula I-12 is more specifically the compound as shown in formula I-19, Formula I-9

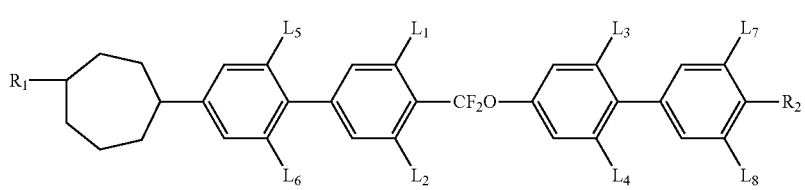

Formula I-10

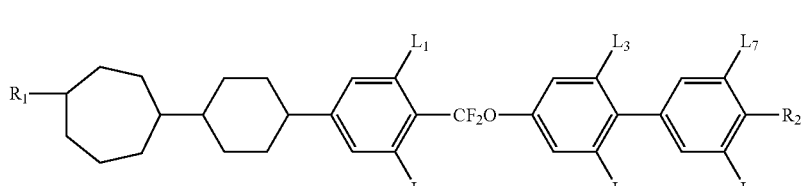

Formula I-19

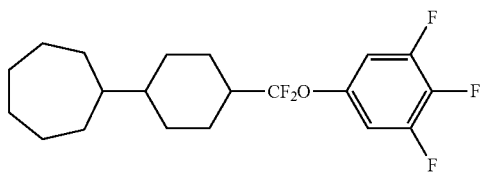

The compound shown in the formula I-4 is specifically the compound as shown in formula I-13 or formula I-14, Formula I-13

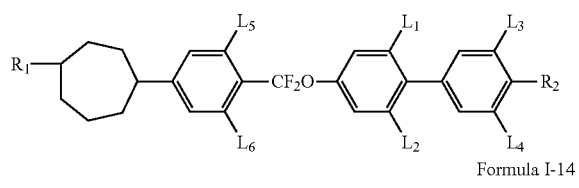

Formula I-14

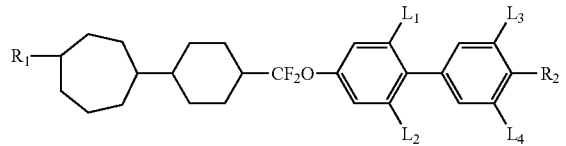

The compound shown in the formula I-5 is specifically the compound as shown in formula I-15, Formula I-15

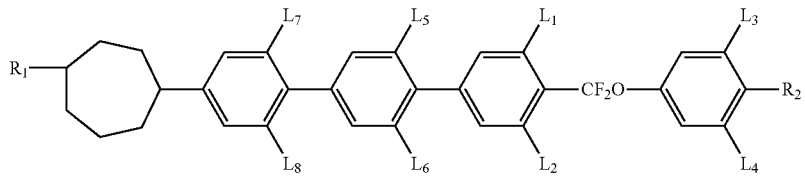

The compound shown in the formula I-15 is more specifically the compound as shown in formula I-20, Formula I-20

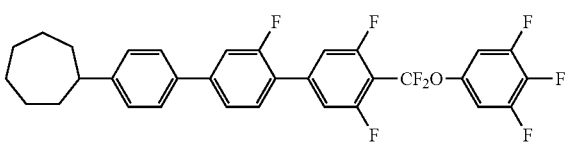

The compound shown in the formula I-6 is specifically the compound as shown in formula I-16, Formula I-16

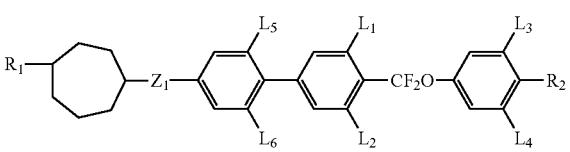

The compound shown in the formula I-16 is more specifically the compound as shown in formula I-21, Formula I-21

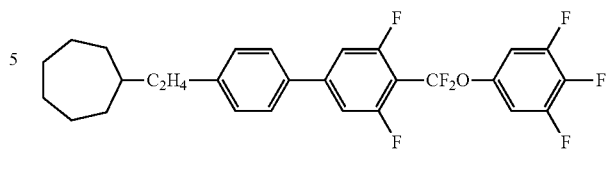

In the formula I-1 to formula I-16, the definition of

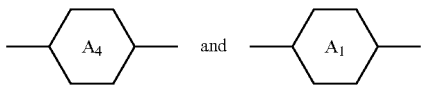

are same;

$L_1, L_2, L_3, L_4, L_5, L_6, L_7$ and $L_8$ are all selected from any one of hydrogen and fluorine;

The definitions of $R_1, R_2, Z_1$, a, b, c,

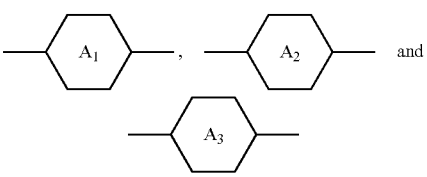

are same with those for formula I.

The compound shown in the above formula I can be obtained according to following processes I to IV:

process I: when the compound is (I-7), (I-9) or (I-16), it is according to the following process:

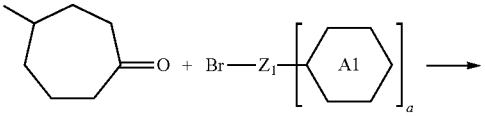

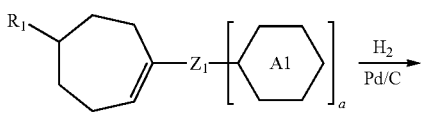

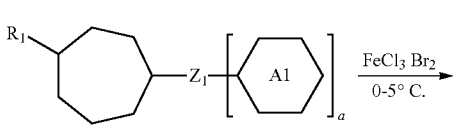

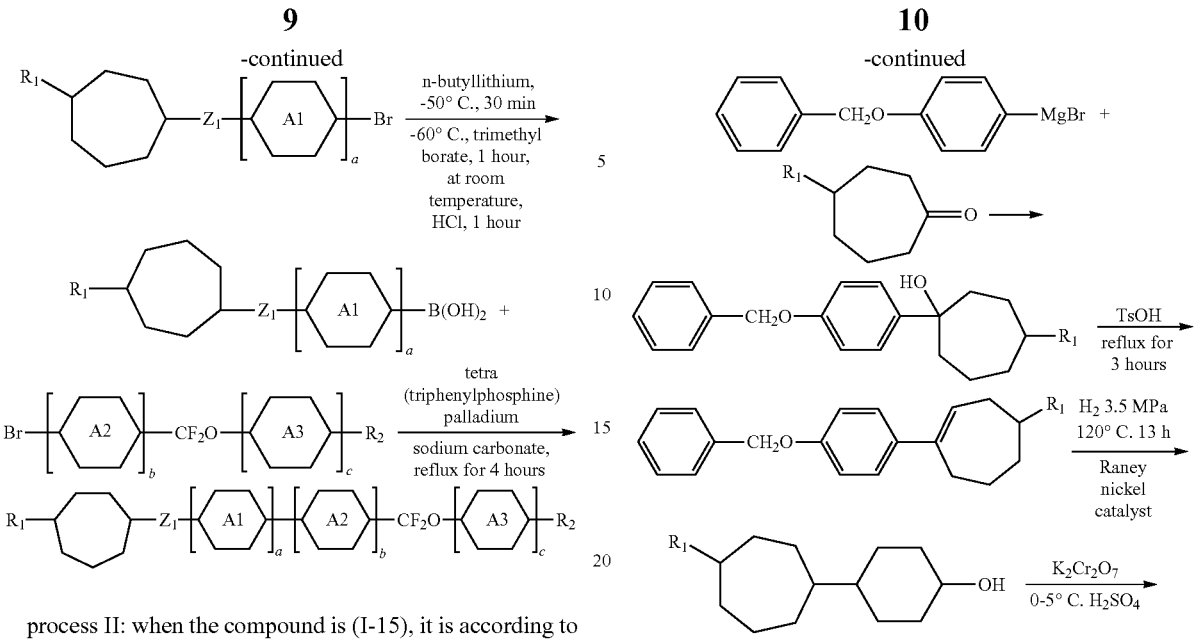
process II: when the compound is (I-15), it is according to the following process:
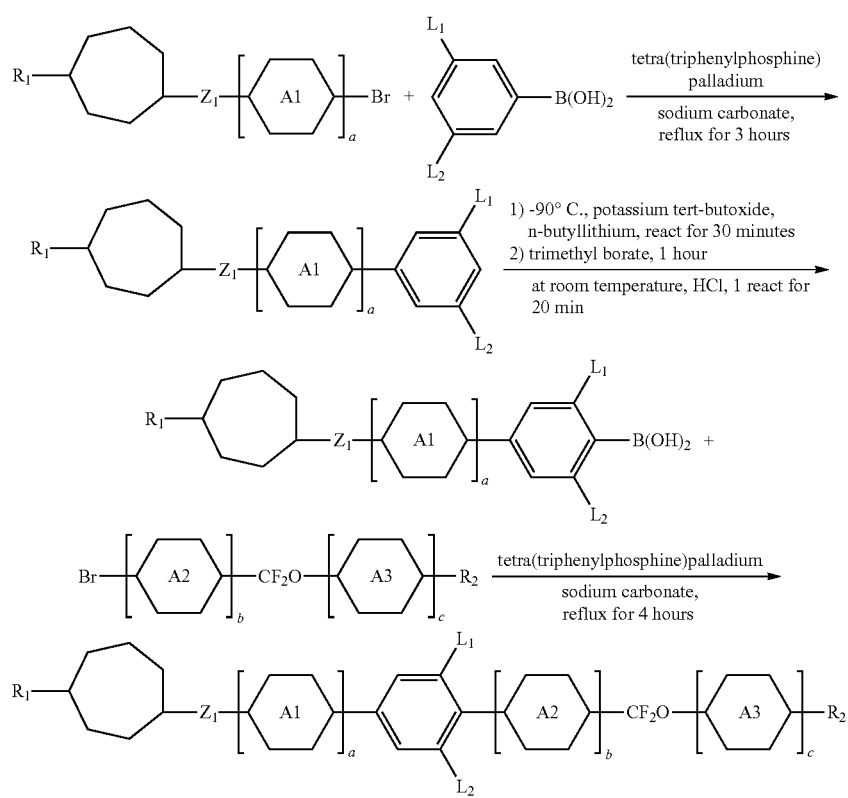
process III: when the compound is (I-12) or (I-14), it is according to the following process:
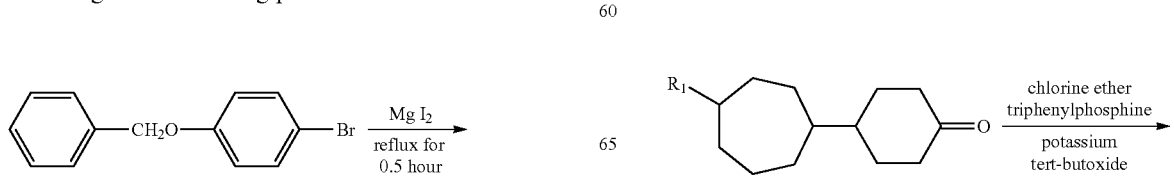

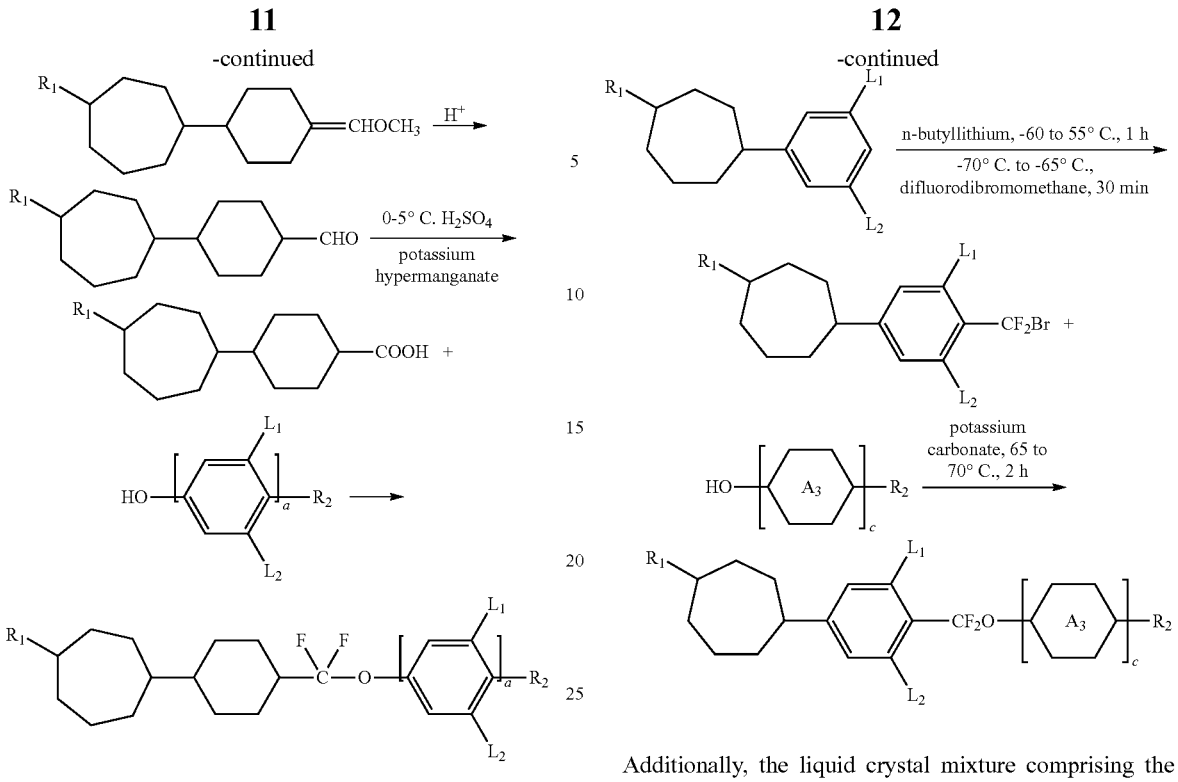

process IV: when the compound is (I-8), (I-10), (I-11) or (I-13), it is according to the following process:

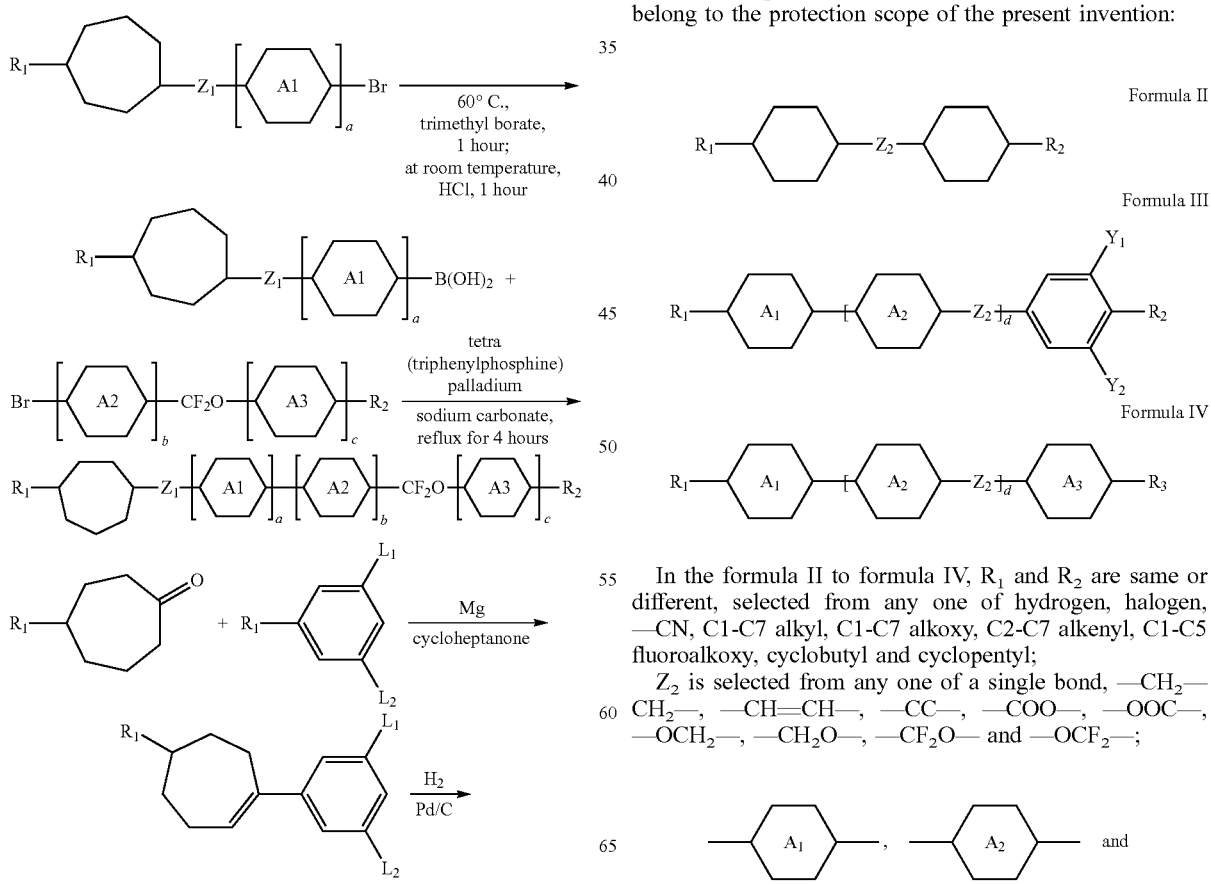

Additionally, the liquid crystal mixture comprising the compound shown in formula I, and the liquid crystal mixture comprising the compound shown in formula I and the compounds shown in formula II to formula IV; or the liquid crystal mixture consisted of the compound shown in formula I and the compound shown in formula II to formula IV also belong to the protection scope of the present invention:

In the formula II to formula IV, $R_1$ and $R_2$ are same or different, selected from any one of hydrogen, halogen, —CN, C1-C7 alkyl, C1-C7 alkoxy, C2-C7 alkenyl, C1-C5 fluoroalkoxy, cyclobutyl and cyclopentyl;

$Z_2$ is selected from any one of a single bond, —$CH_2$—$CH_2$—, —CH=CH—, —CC—, —COO—, —OOC—, —$OCH_2$—, —$CH_2O$—, —$CF_2O$— and —$OCF_2$—;

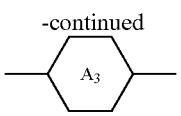

are selected from at least one of single bond and the following groups:

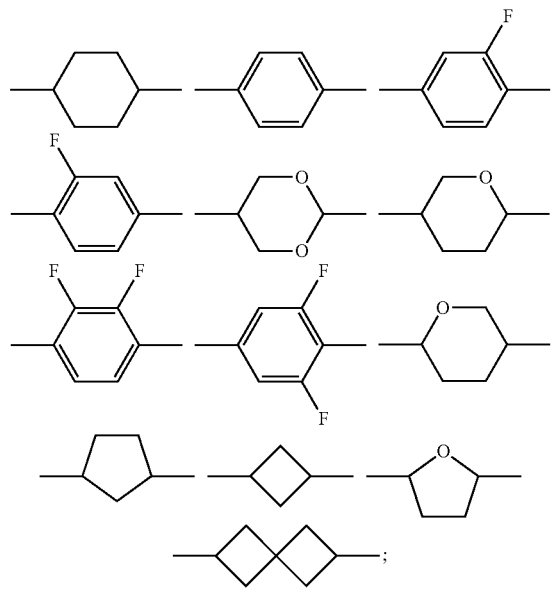

$Y_1$ and $Y_2$ are selected from any one of H and F;
d is a integer from 0 to 2.

In particular, in the formula II to formula IV, the alkyl group of C1-C7 is selected in particular from at least one of C2-C7 alkyl, C3-C7 alkyl, C4-C7 alkyl, C5-C7 alkyl, C6-C7 alkyl, C1-C6 alkyl, C2-C6 alkyl, C3-C6 alkyl, C4-C6 alkyl, C5-C6 alkyl, C1-C5 alkyl, C2-C5 alkyl, C3-C5 alkyl, C4-C5 alkyl, C1-C4 alkyl, C2-C4 alkyl, C3-C4 alkyl, C1-C3 alkyl, C1-C2 alkyl and C2-C3 alkyl;

The C1-C7 alkoxy is selected in particular from at least one of C2-C7 alkoxy, C3-C7 alkoxy, C4-C7 alkoxy, C5-C7 alkoxy, C6-C7 alkoxy, C1-C6 alkoxy, C2-C6 alkoxy, C3-C6 alkoxy, C4-C6 alkoxy, C5-C6 alkoxy, C1-C5 alkoxy, C2-C5 alkoxy, C3-C5 alkoxy, C4-C5 alkoxy, C1-C4 alkoxy, C2-C4 alkoxy, C3-C4 alkoxy, C1-C3 alkoxy, C1-C2 alkoxy and C2-C3 alkoxy;

The C2-C7 alkenyl is selected in particular from at least one of C3-C7 alkenyl, C4-C7 alkenyl, C5-C7 alkenyl, C6-C7 alkenyl, C2-C6 alkenyl, C3-C6 alkenyl, C4-C6 alkenyl, C5-C6 alkenyl, C2-C5 alkenyl, C3-C5 alkenyl, C4-C5 alkenyl, C2-C4 alkenyl, C3-C4 alkenyl and C2-C3 alkenyl;

The fluoroalkoxy with the total number of carbon atoms of 1 to 5 is selected from at least one of C2-C5 fluoroalkoxy, C3-C5 fluoroalkoxy, C4-C5 fluoroalkoxy, C1-C4 fluoroalkoxy, C2-C4 fluoroalkoxy, C3-C4 fluoroalkoxy, C1-C3 fluoroalkoxy, C1-C2 fluoroalkoxy and C2-C3 fluoroalkoxy;

In the above liquid crystal mixtures, the mass ratio of the compound represented by formula I, the compound represented by formula II, formula III and formula IV is 0-30: 4-50: 5-50:3-45, specifically 6-22: 12-36: 24-48: 14-38 or 10-14: 20-27: 41-47: 19-34, 6-11: 22-24: 41-45: 21-33; the weight of the compound represented by formula I is not 0.

In particular, the liquid crystal mixture is any one of the liquid crystal mixtures a-h:

The liquid crystal mixture a comprises or consists of the following components in the respective parts by weight thereof:

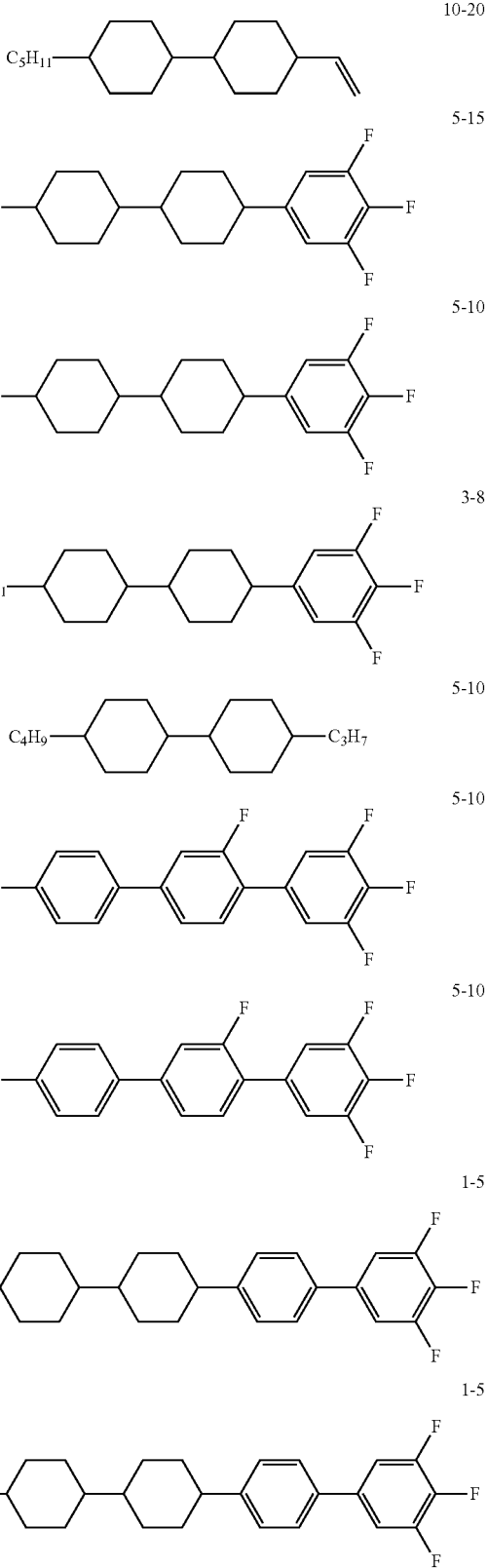

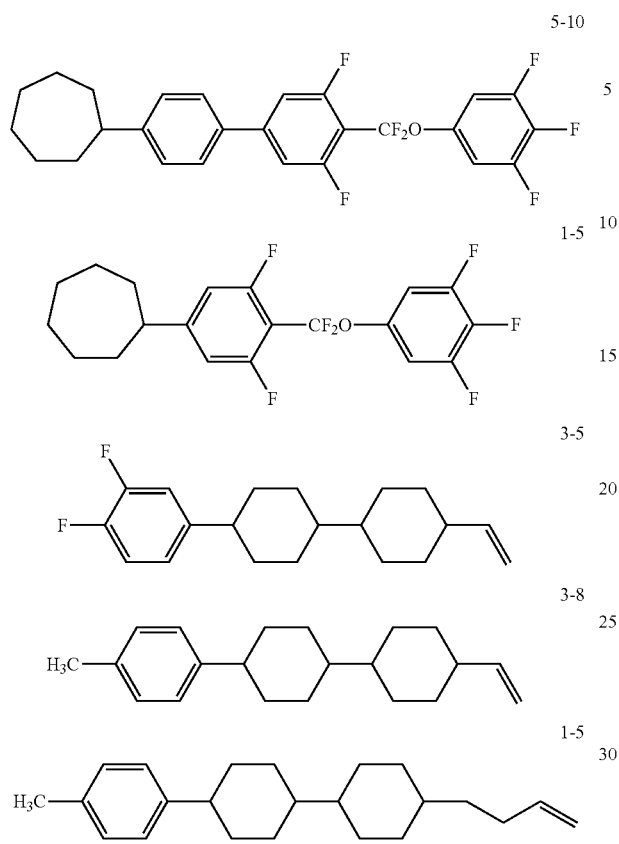
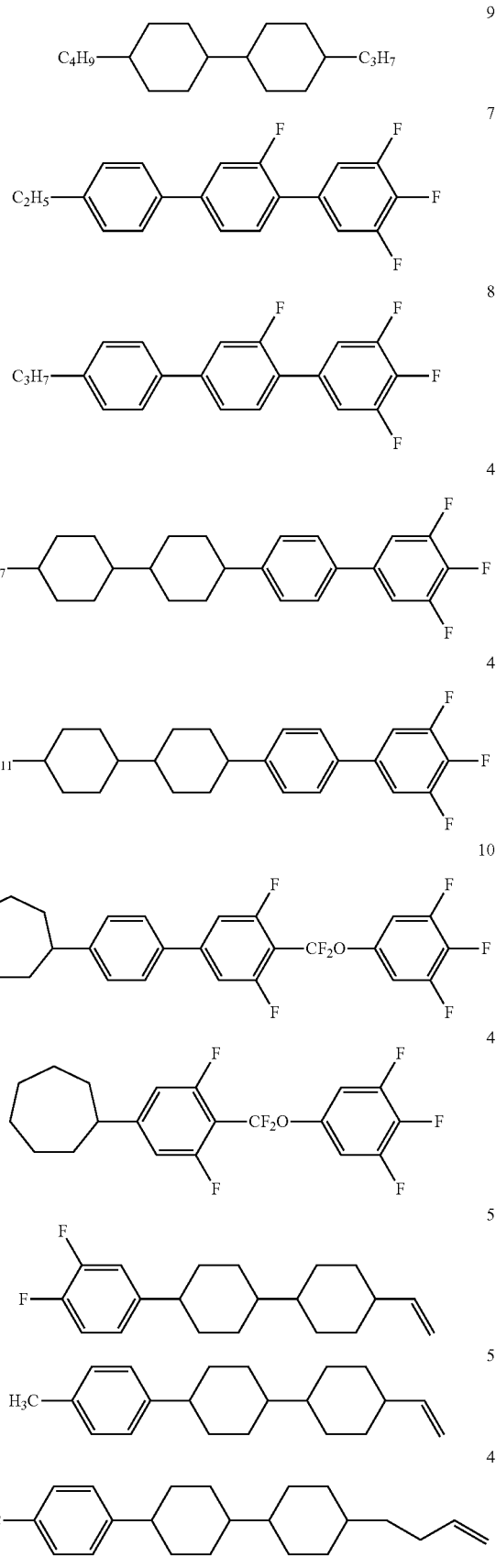
The liquid crystal mixture a specifically comprises or consists of the following components in the respective parts by weight thereof:

The liquid crystal mixture b comprises or consists of the following components in the respective parts by weight thereof:
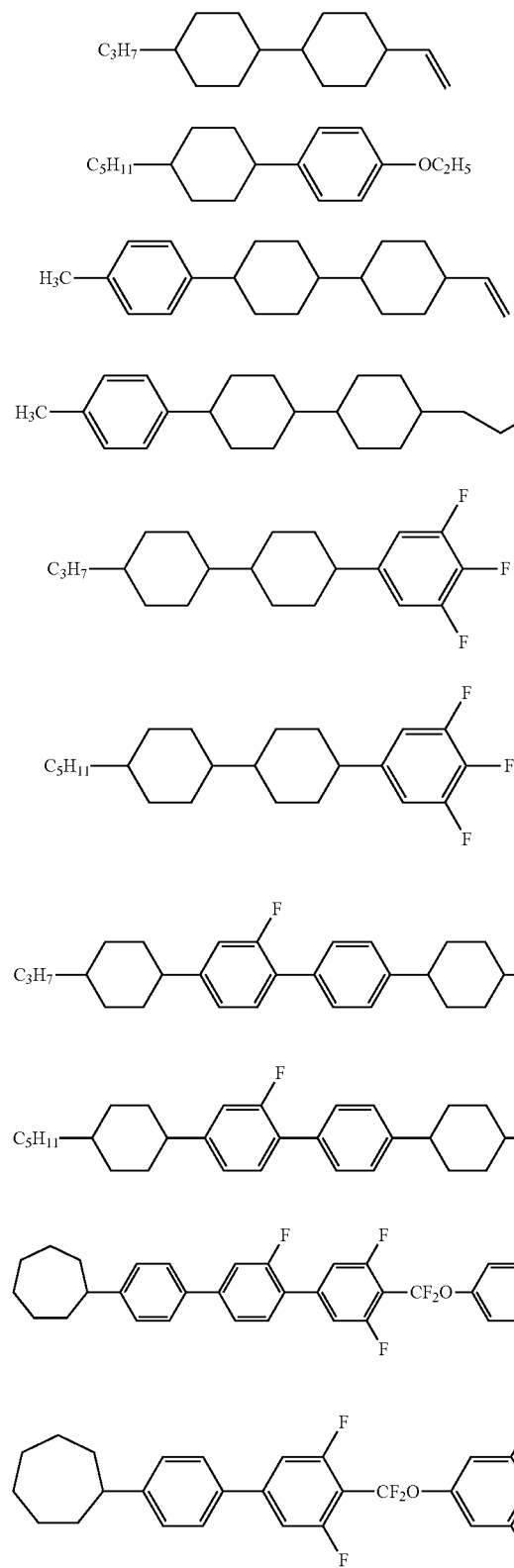
The liquid crystal mixture b specifically comprises or consists of the following components in the respective parts by weight thereof:
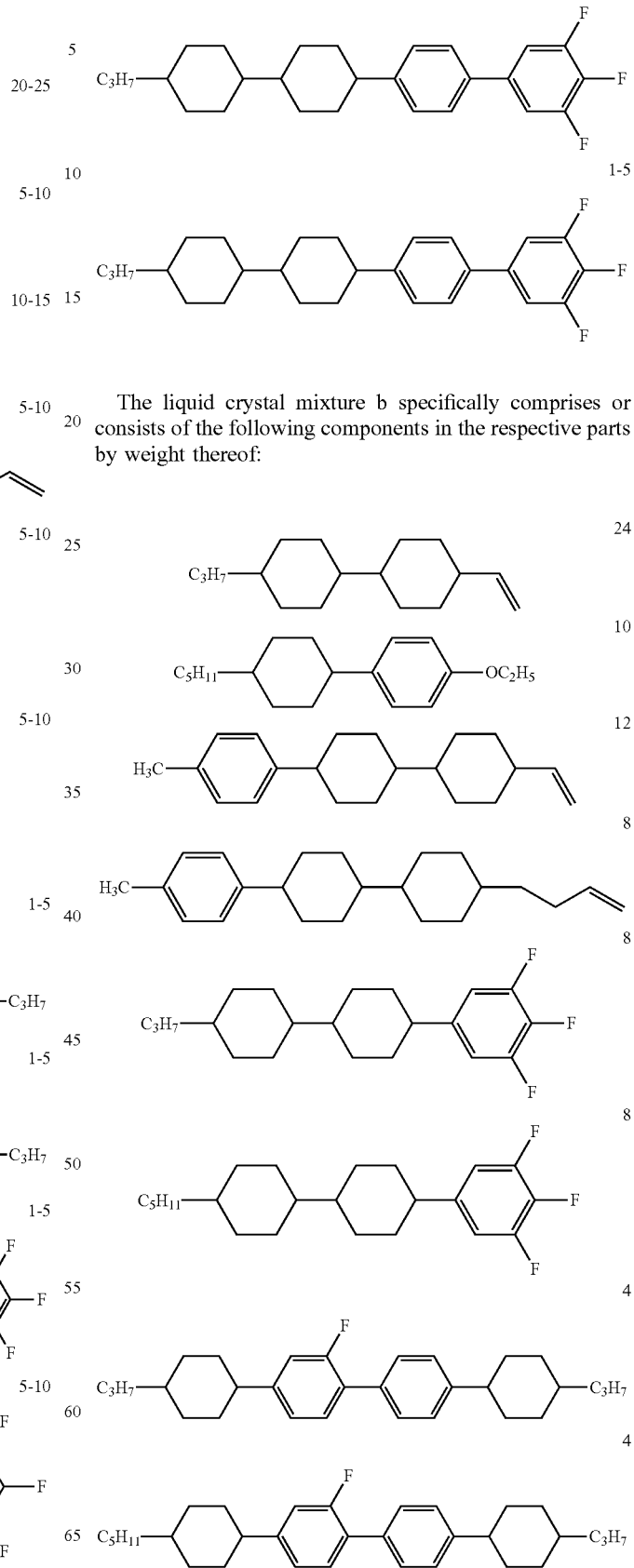

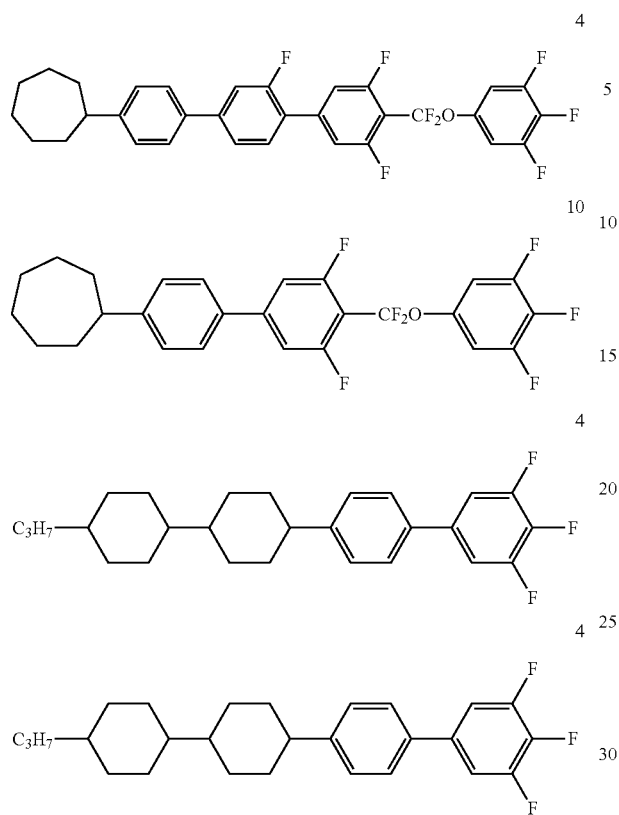
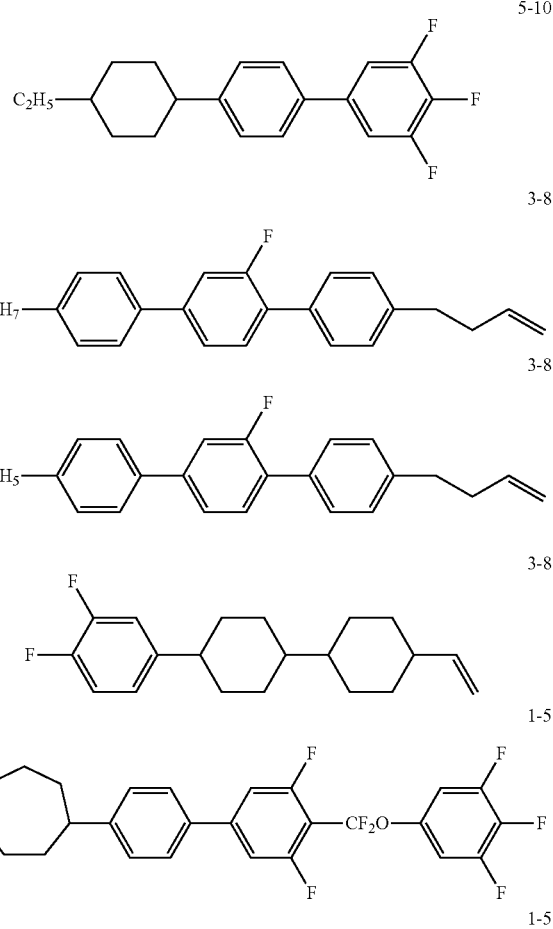
The liquid crystal mixture c comprises or consists of the following components in the respective parts by weight thereof:
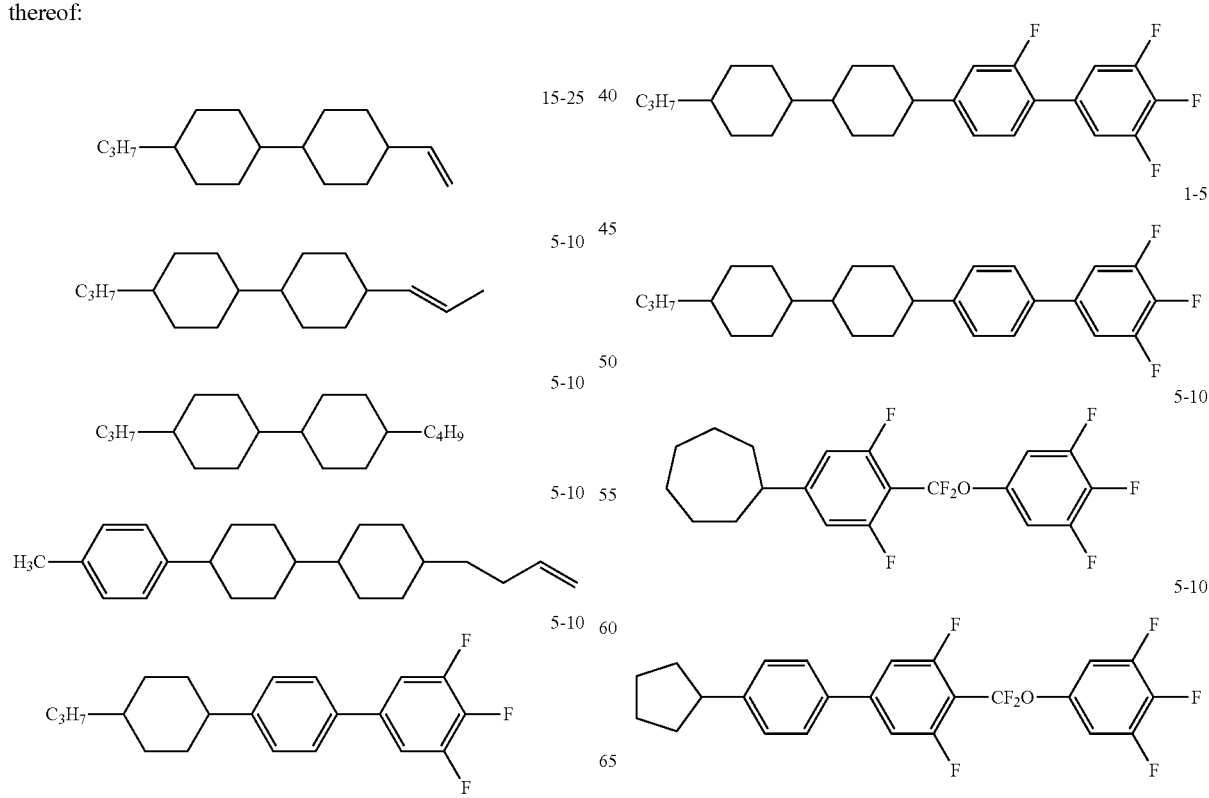

The liquid crystal mixture c specifically comprises or consists of the following components in the respective parts by weight thereof:
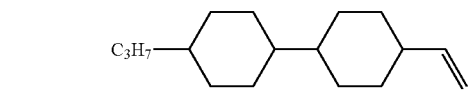
20
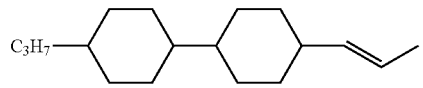
6
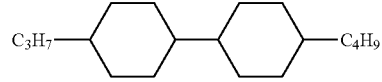
6
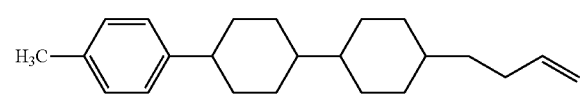
9
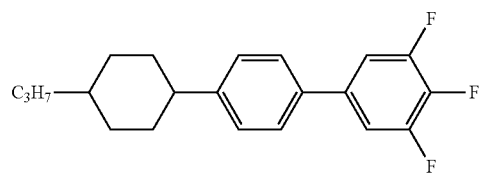
7
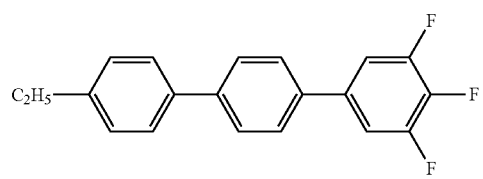
5
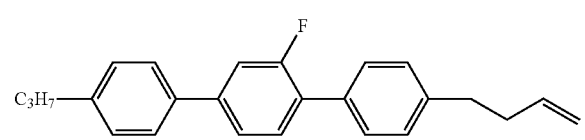
5
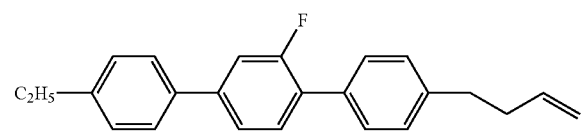
5
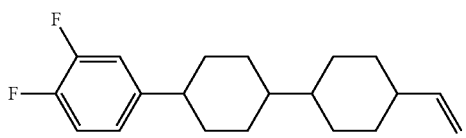
4
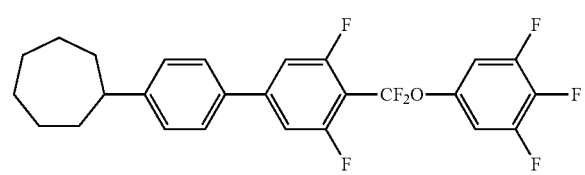
4
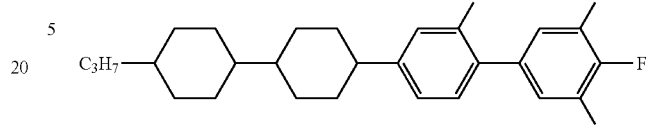
4
4
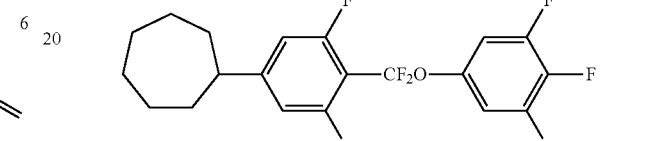
7
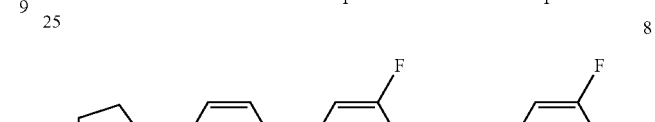
8
The liquid crystal mixture d comprises or consists of the following components in the respective parts by weight thereof:
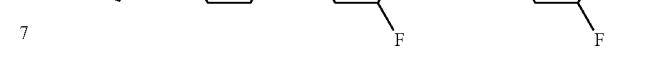
20-25
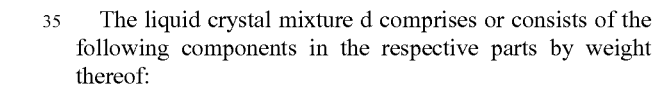
1-5
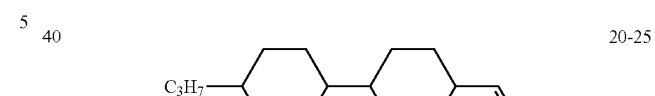
3-8
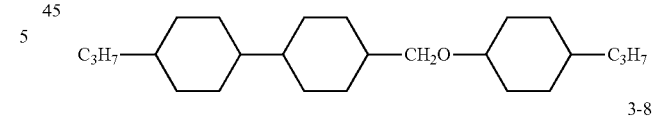
10-15
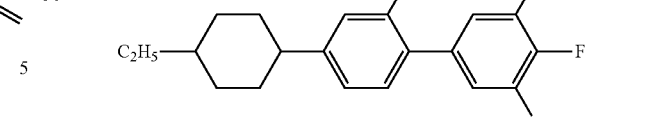
3-8
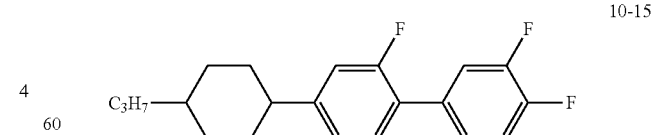
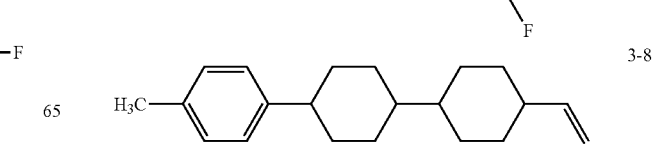

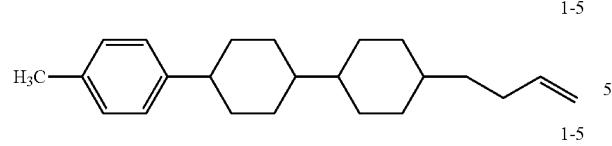
1-5
1-5
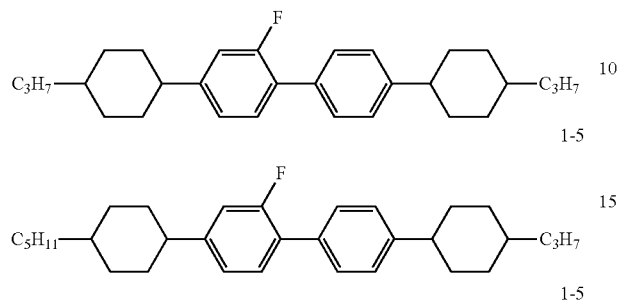
1-5
1-5
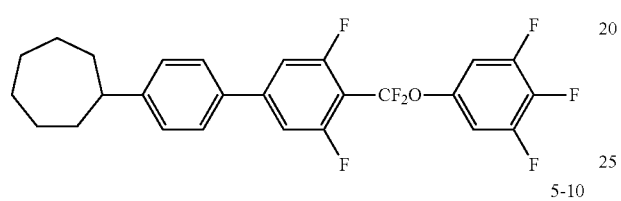
5-10
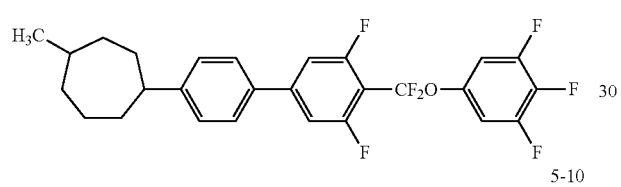
5-10
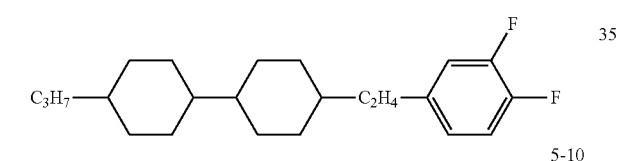
5-10
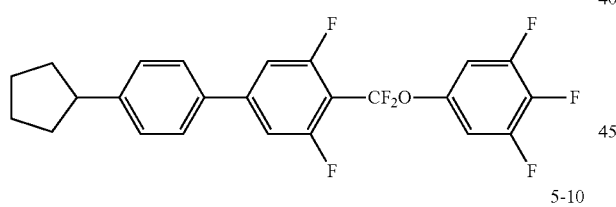
5-10
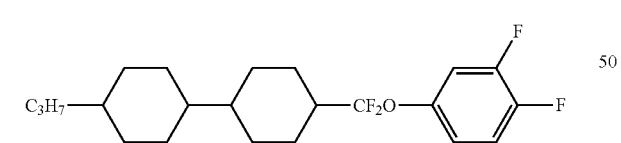
5-10
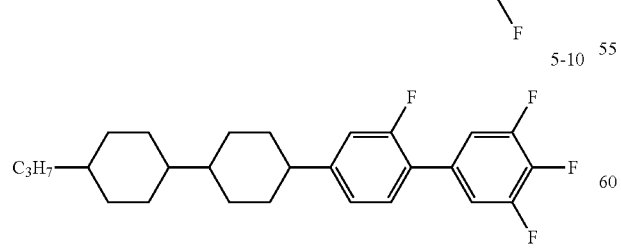
The liquid crystal mixture d specifically comprises or consists of the following components in the respective parts by weight thereof:
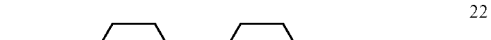
22
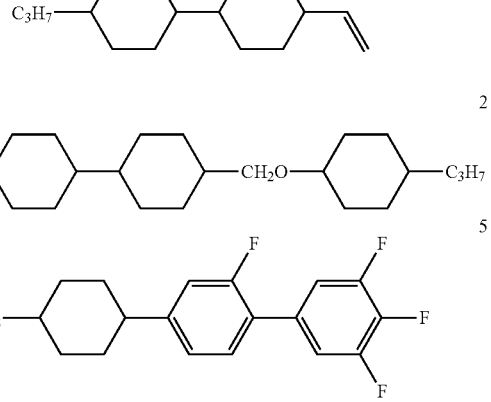
2
5
12
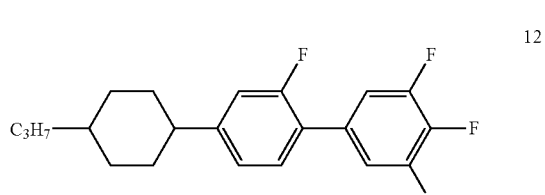
5
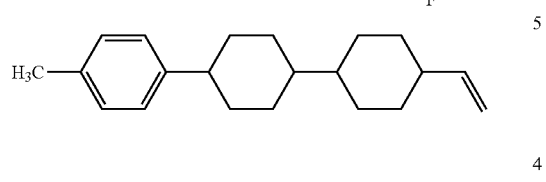
4
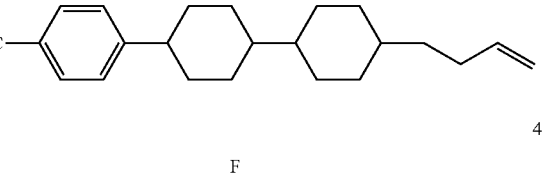
4
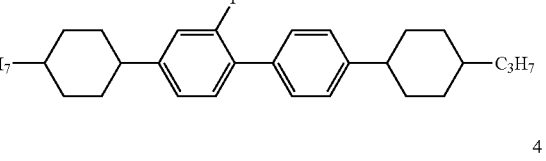
4
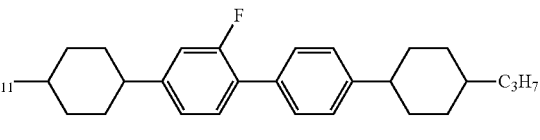
4
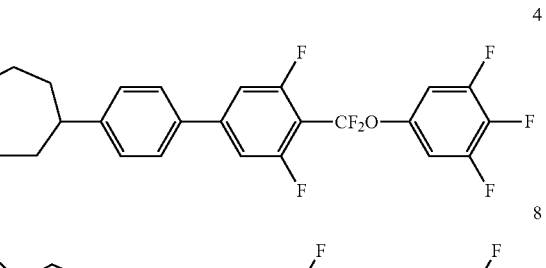
8

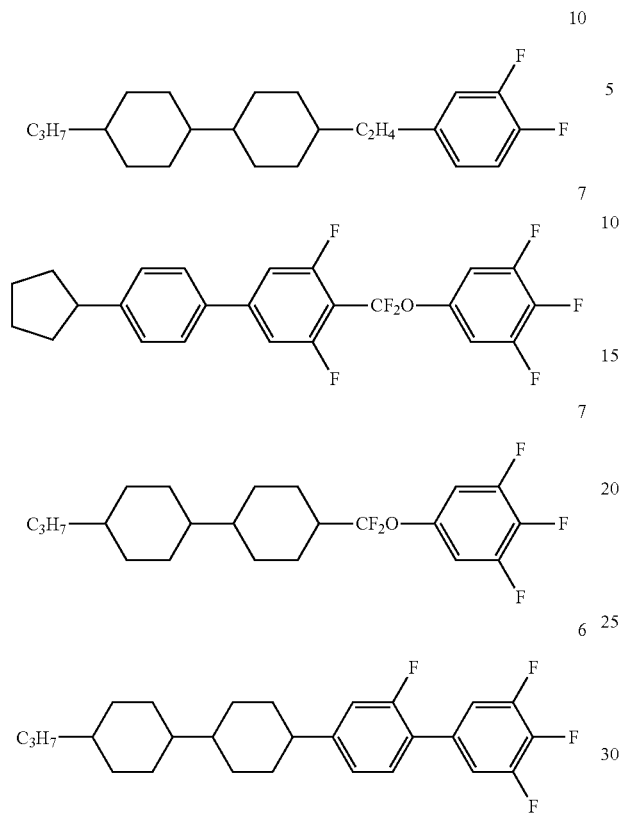
The liquid crystal mixture e comprises or consists of the following components in the respective parts by weight thereof:
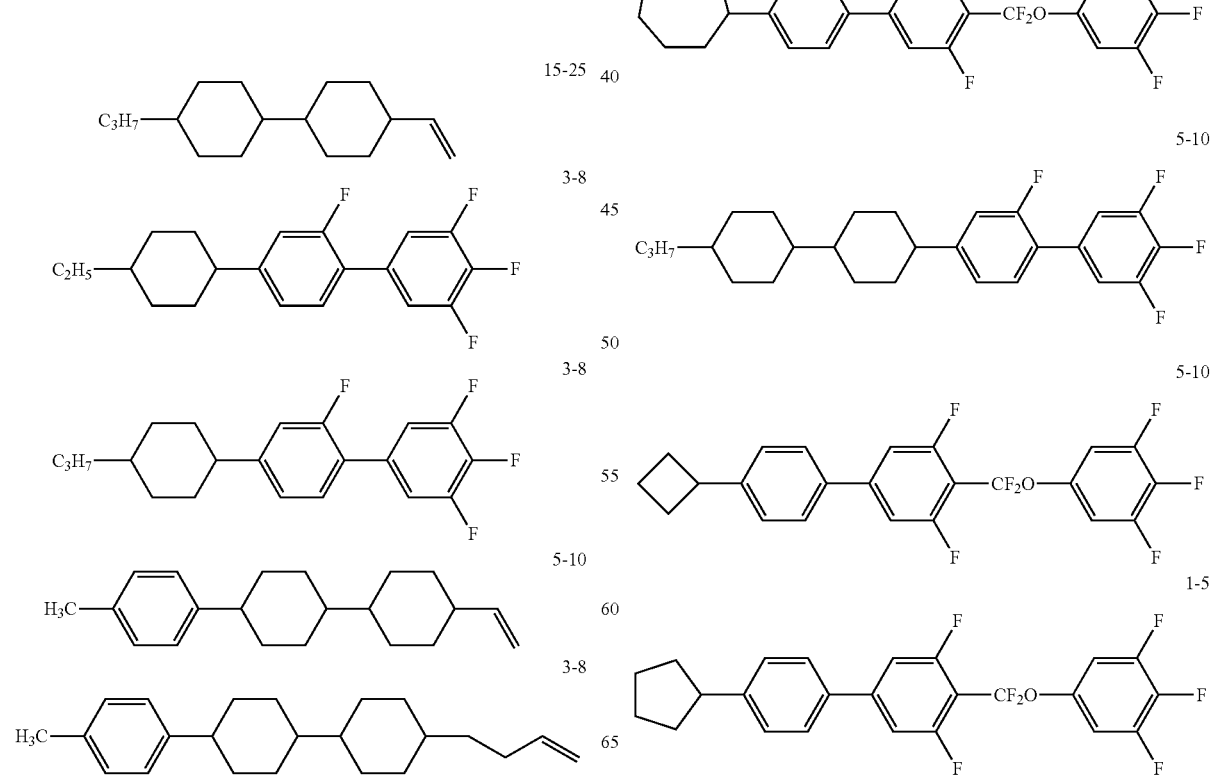

The liquid crystal mixture e specifically comprises or consists of the following components in the respective parts by weight thereof:
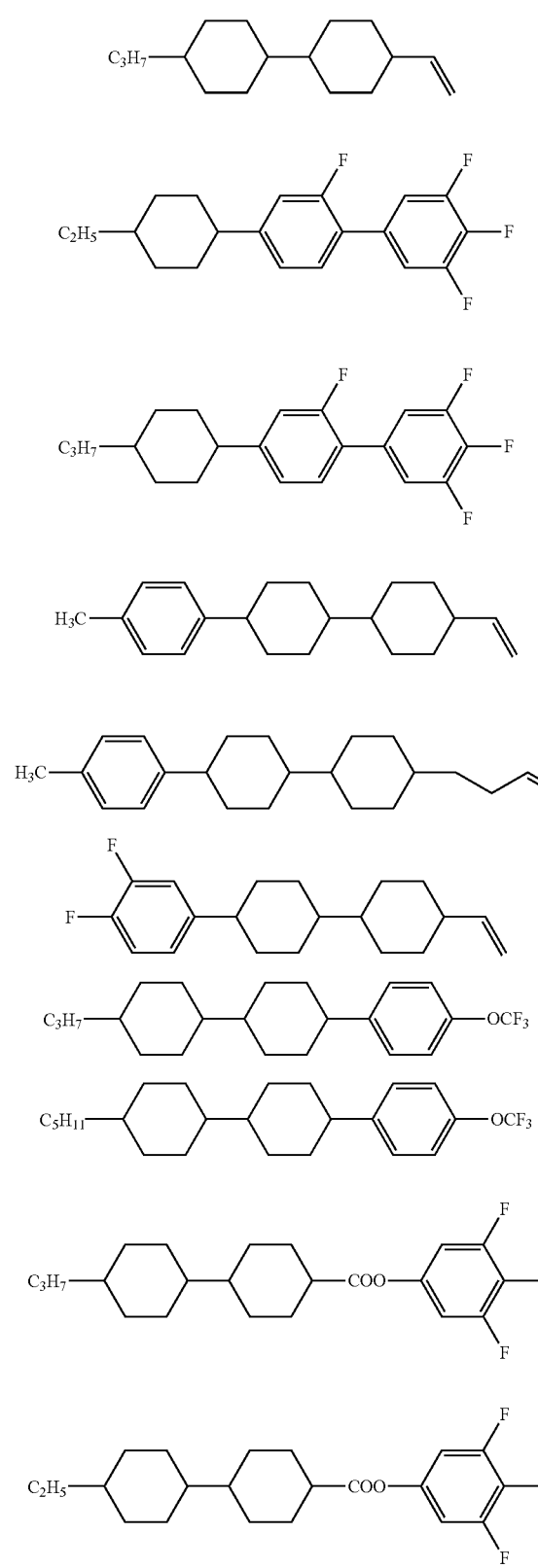
-continued
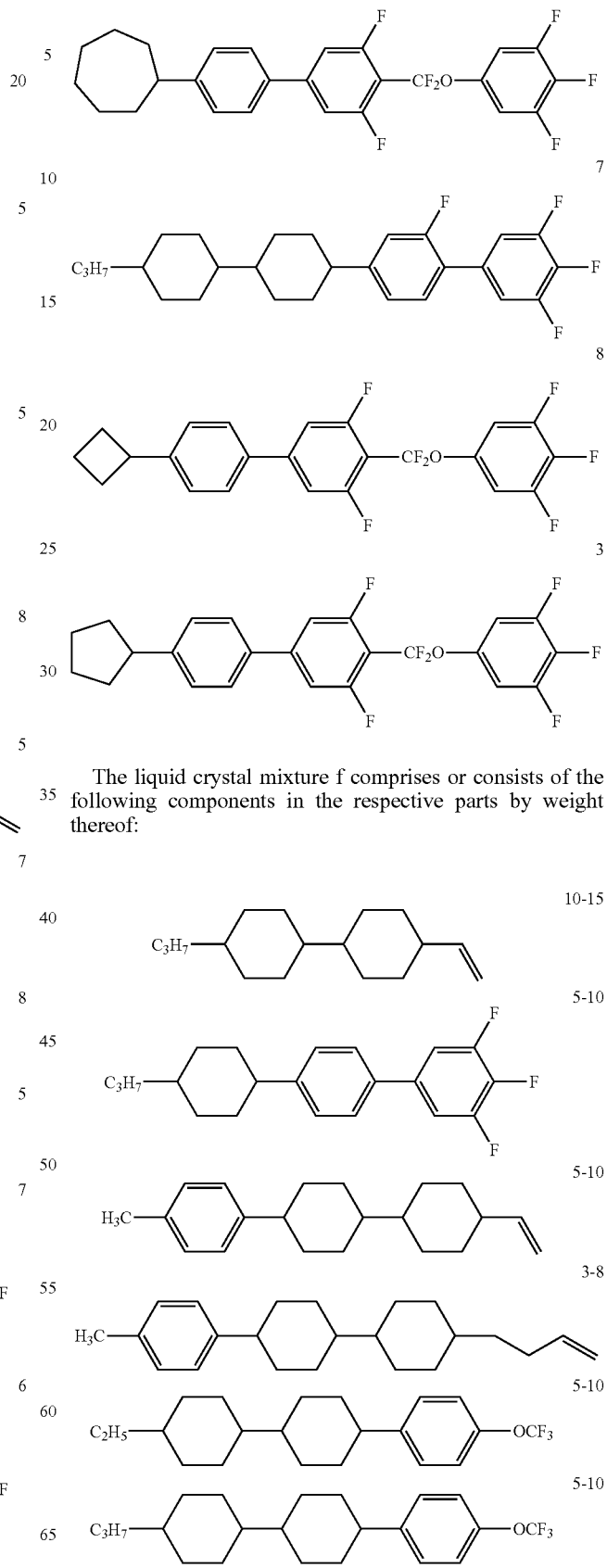
The liquid crystal mixture f comprises or consists of the following components in the respective parts by weight thereof:

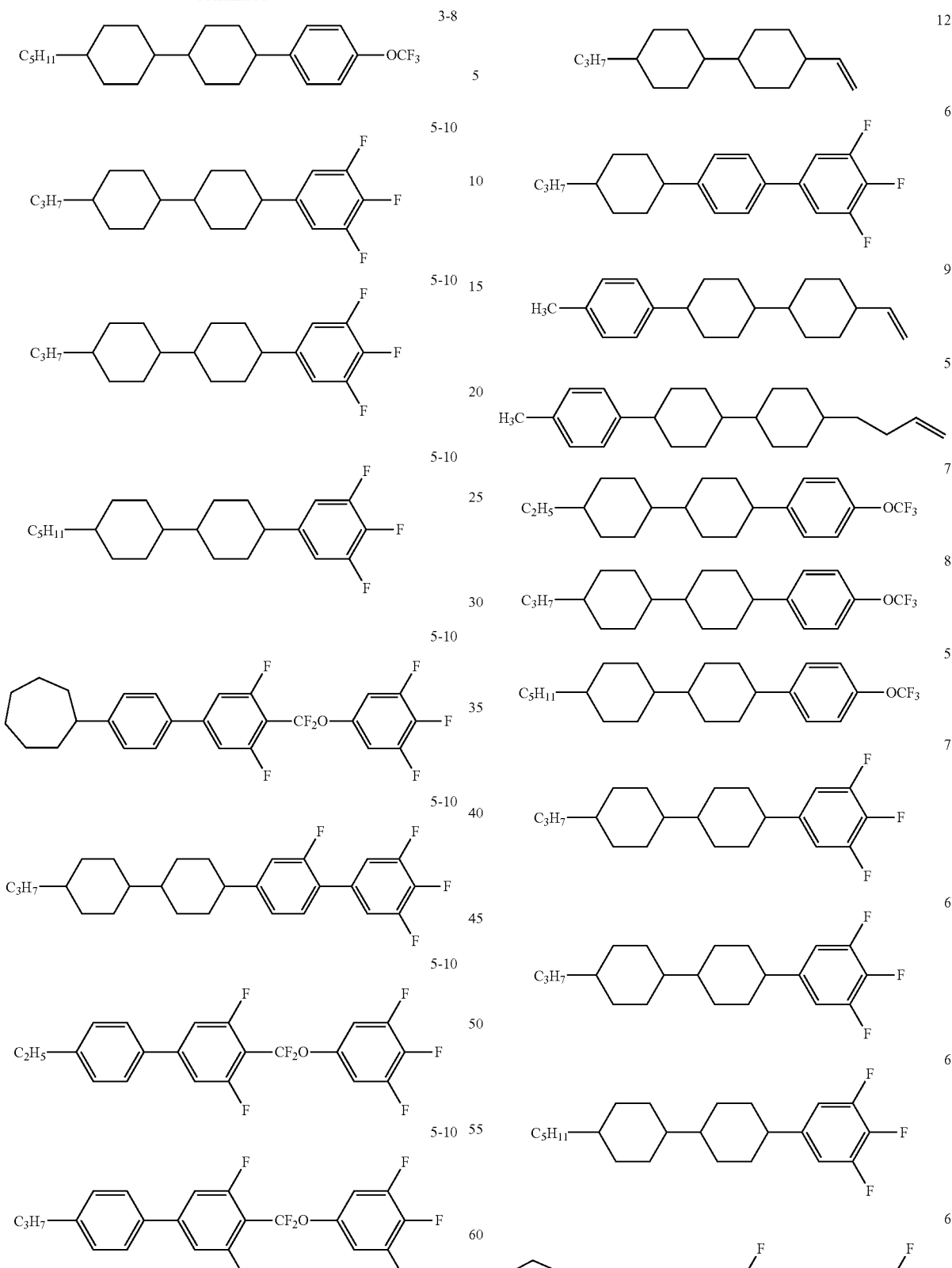
The liquid crystal mixture f specifically comprises or consists of the following components in the respective parts by weight thereof:

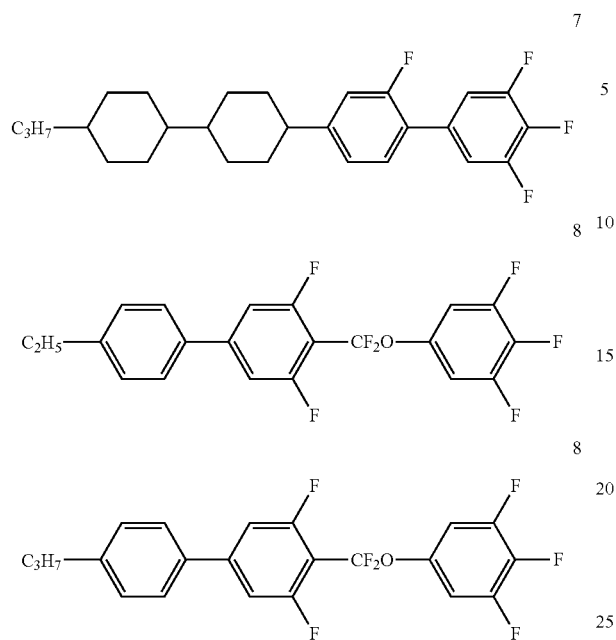
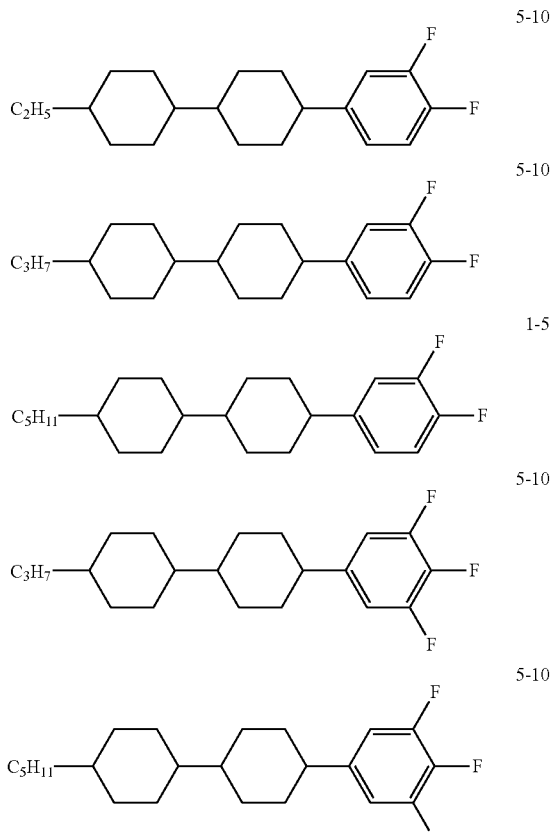
The liquid crystal mixture g comprises or consists of the following components in the respective parts by weight thereof:
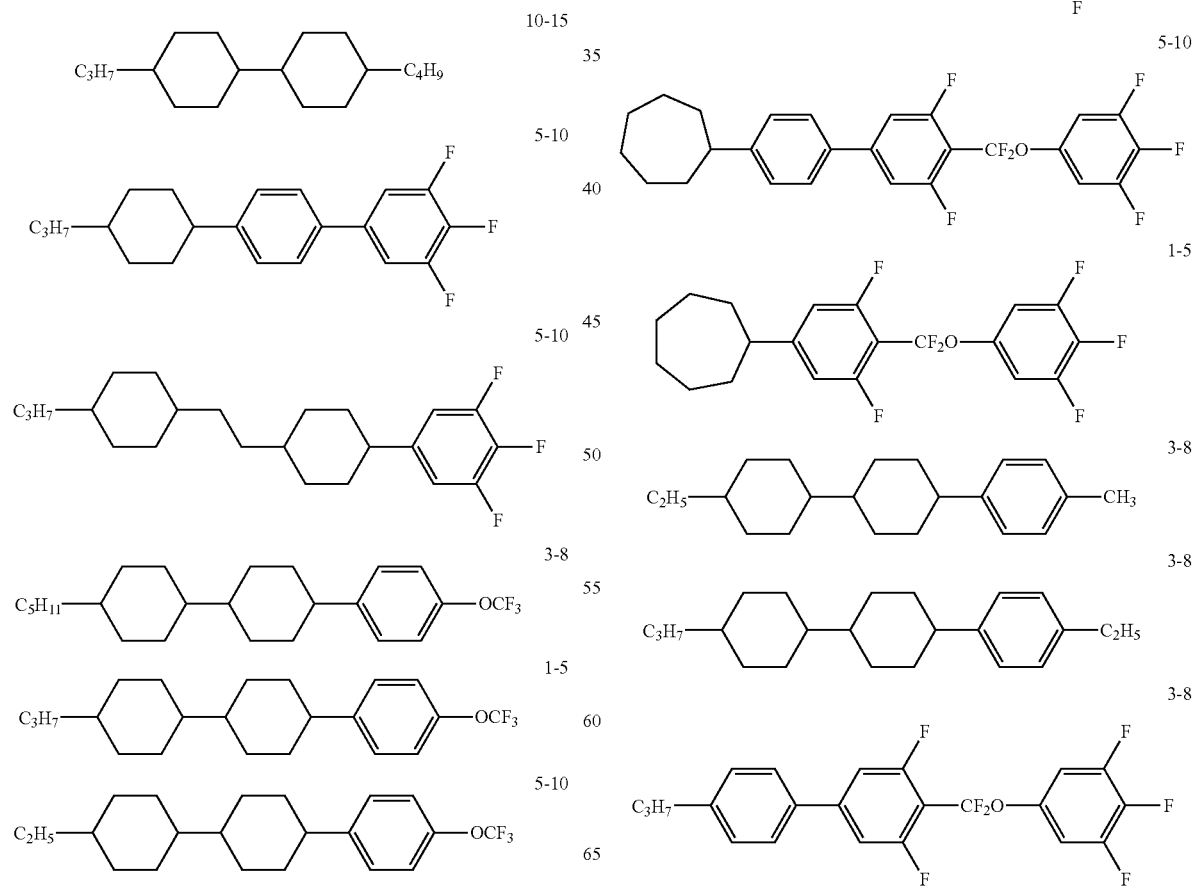

-continued
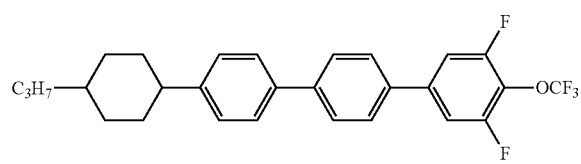
1-5
The liquid crystal mixture g specifically comprises or consists of the following components in the respective parts by weight thereof:
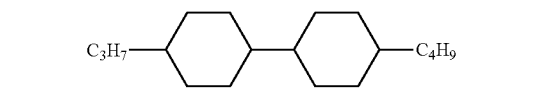
12
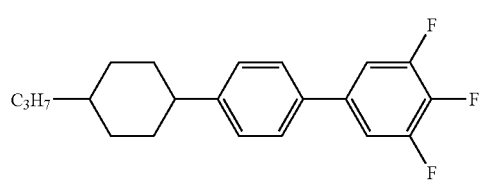
6
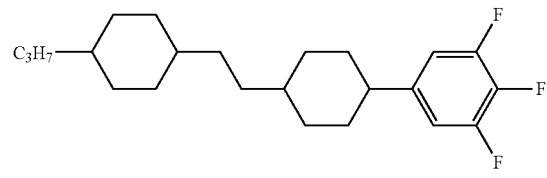
9
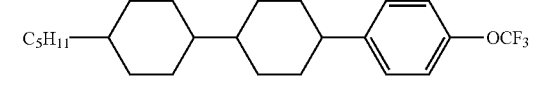
5
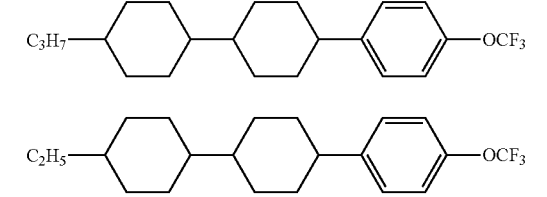
4
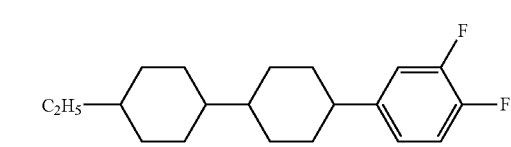
8
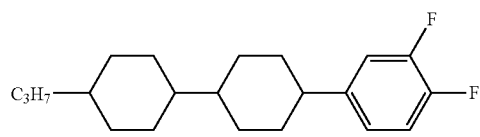
8
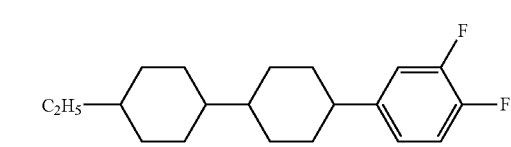
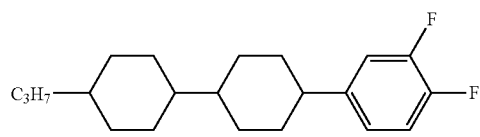
5
3
-continued
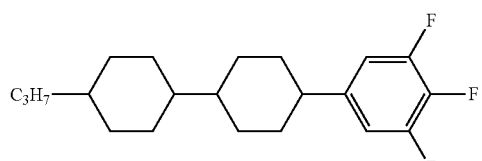
6
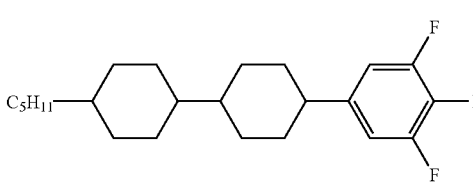
6
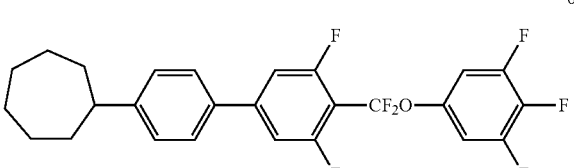
6
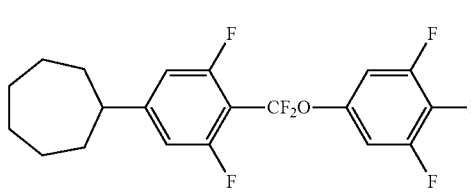
4
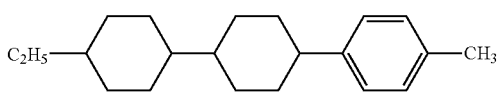
5
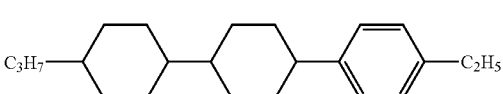
5
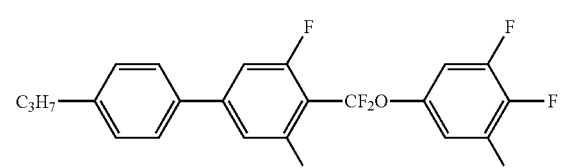
5
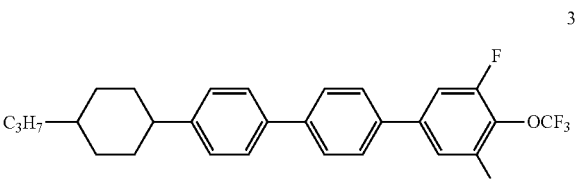
3
The liquid crystal mixture h comprises or consists of the following components in the respective parts by weight thereof:
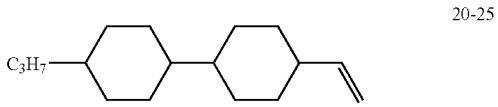
20-25

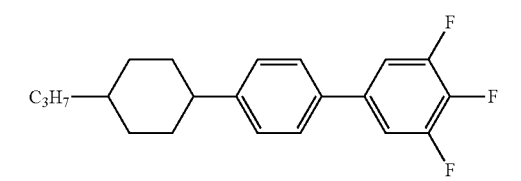 5-10
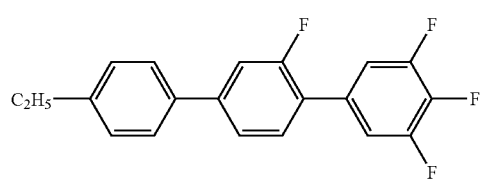 5-10
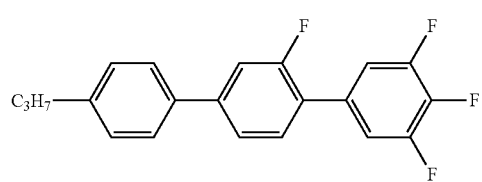 3-8
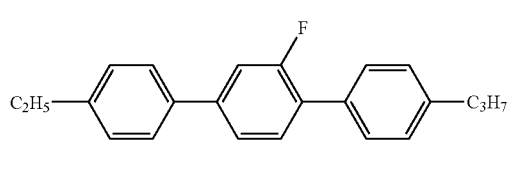 1-5
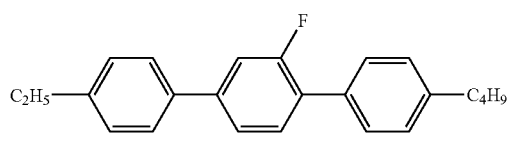 1-5
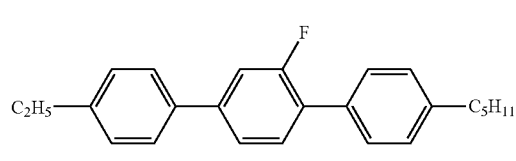 1-5
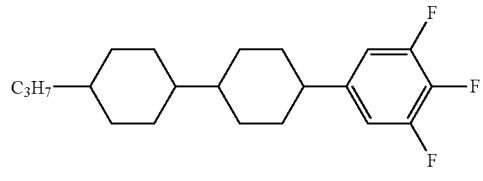 5-10
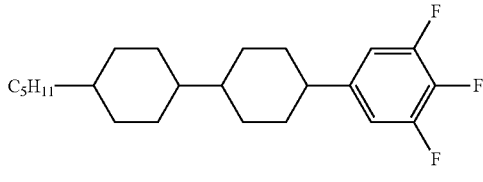 5-10
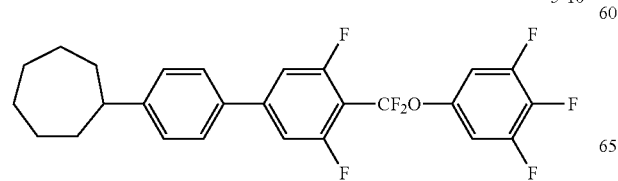 5-10
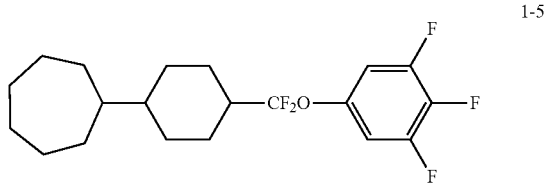 1-5
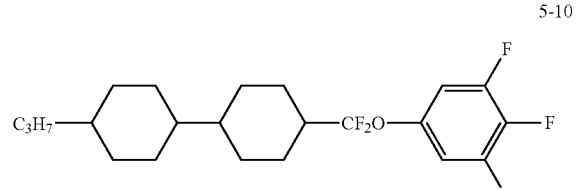 5-10
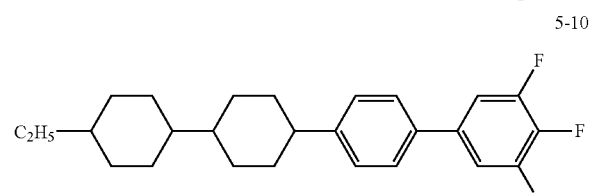 5-10
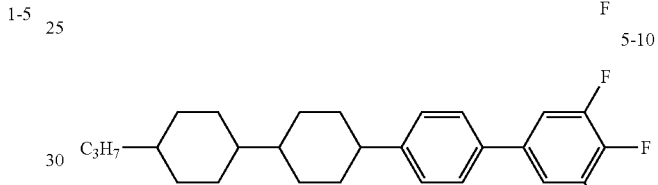 5-10
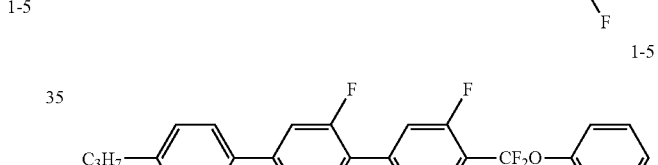 1-5
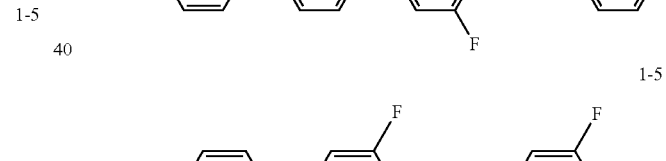 1-5
The liquid crystal mixture h specifically comprises or consists of the following components in the respective parts by weight thereof:
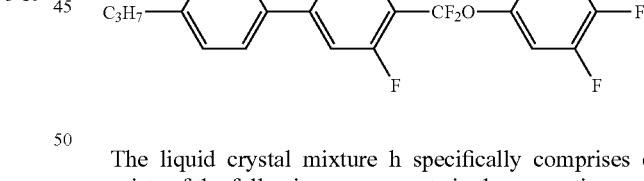 22
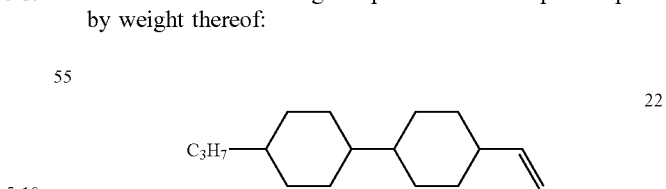 6

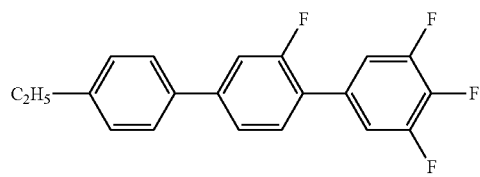
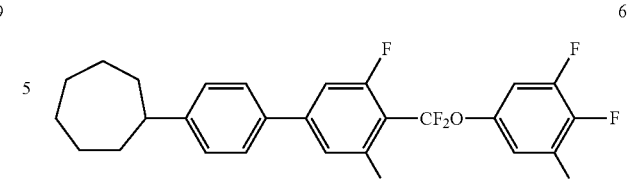
The liquid crystal mixture also comprises at least one of the following components: an optical active compound and a polymerizable compound.

The optical active compound specifically may be a chiral dopant with the following various structures:

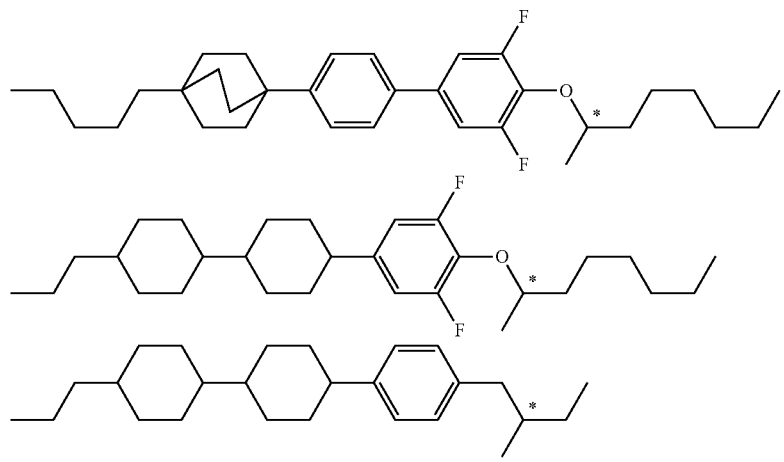

The above chiral dopant has the effect of inducing the helical structure of liquid crystal so as to adjust the necessary torsion angle and prevent the inverse torsion, the mass ratio of the additive amount of the chiral dopant to the liquid crystal mixture is 0.1 to 0.3:100.

mass ratio of the additive amount of polymerizable compound to the liquid crystal mixture is 0.1 to 2:100.

The polymerizable compounds are more specifically the following compounds:

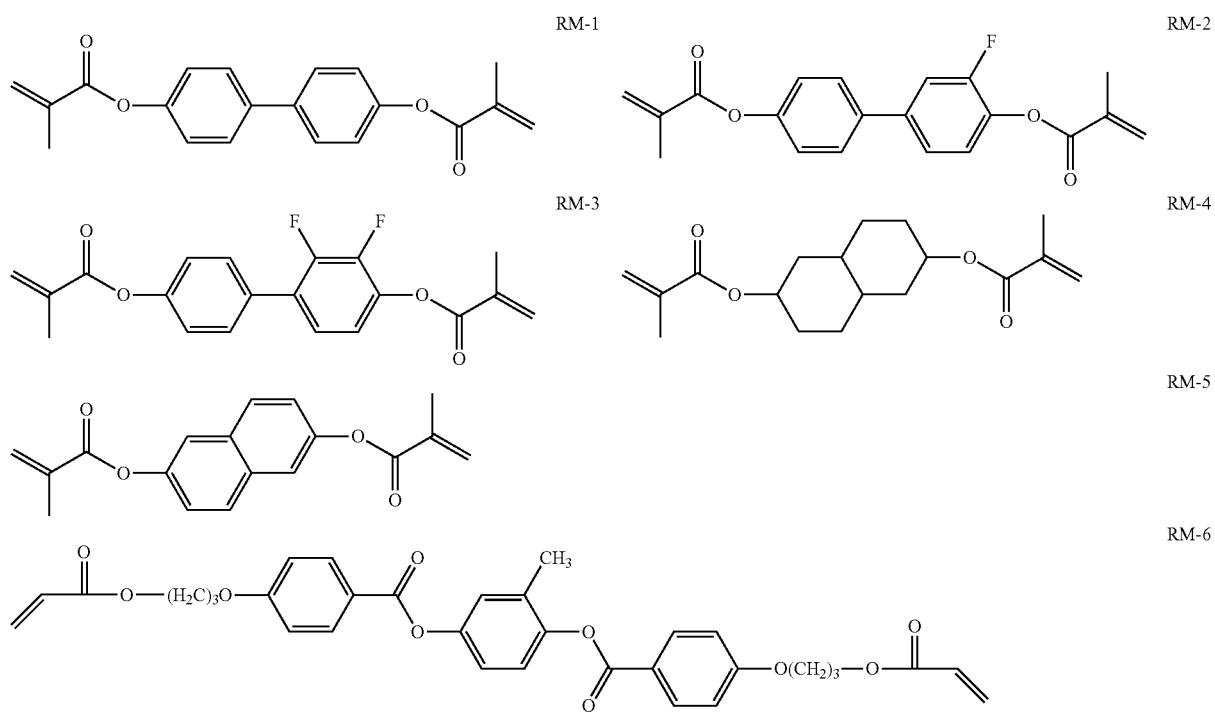

In order to be applicable to the elements of polymer sustained alignment (PSA) mode, the polymerizable compound can be mixed in the liquid crystal mixture. The preferred examples of polymerizable compound are the compounds with polymerizable groups, such as acrylate, methacrylate, vinyl compound, vinyloxy compound, propenyl ether, epoxy compound (ethylene oxide, propylene oxide), vinyl ketone, and the like. The most preferred example is the derivative of acrylate or methacrylate. The use of the compound shown in formula I and the liquid crystal composition provided by the above invention in the manufacture of a liquid crystal display material or an electro-optical display material also belongs to the scope of the present invention. Wherein, the liquid crystal display material or electro-optical display material is a display, in particularly a TN type display, VA type display, IPS type display or PDLC type display.

BEST MODES OF THE EMBODIMENTS

Figure 1:
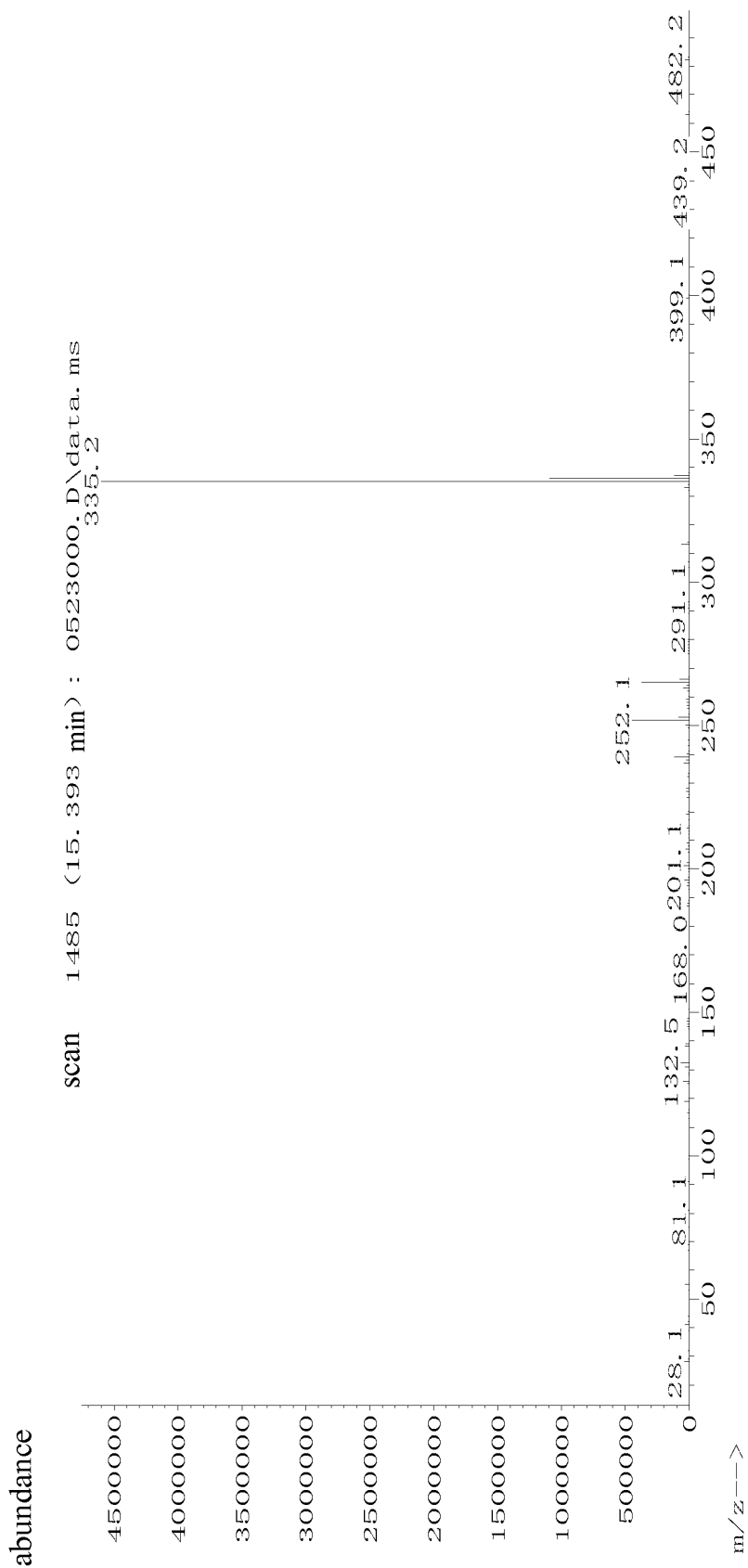
FIG. 1 is a mass spectrogram of the product of Example 1.

The following examples serve to illustrate the present invention, but the present invention is not limited to the embodiments below. The methods are conventional methods if not otherwise specified. The materials can be available commercially from market if not otherwise specified. The mass percentage concentration of the concentrated sulfuric acid used in all the following examples is 98%, and the mass percentage concentration of all the used concentrated hydrochloric acid is 37%.

In the following Examples, GC represents gas chromatography purity, HPLC represents the liquid chromatography purity, MP means melting point, MS represents mass spectrum, $^1$H-NMR represents nuclear magnetic resonance spectrum of hydrogen, $\Delta\epsilon$ represents dielectric anisotropy, and $\Delta n$ represents optical anisotropy.

The structures of the product shown in formula I obtained from the following examples are confirmed by using gas chromatography, liquid chromatography, GC-MS and 1H-NMR spectra. GC is measured by HP6820 type gas chromatograph analyzer of Agilent, GC-MS analysis device is Agilent MS5975C type, 1H-NMR is measured by DRX-500 analysis device of Bruker. B I osp In company, melting point is determined by using the WRX-1S microscopic thermal analyzer with the heating rate set as 3° C./min.

Physical properties of the product of formula I obtained from the following examples are determined in two ways: the compound itself as a sample for measurement and the compound mixed with the mother liquid crystal as a sample for measurement. The measurement mode of the physical properties of the compound by mixing the compound with a mother liquid crystal as a sample: the sample is first prepared by mixing 15% of the liquid crystal compound and 85% of the mother liquid crystal, then according to the obtained measured values of the sample, the extrapolated values are calculated according to the extrapolation shown in the following formula, extrapolated value=[100×(measured value of sample)−(weight percentage of mother liquid crystal)×(measured value of mother liquid crystal)]/weight percentage of the compound, Thus, the physical properties of monomer liquid crystal compound are obtained.

The composition of the used mother liquid crystal is as follows:

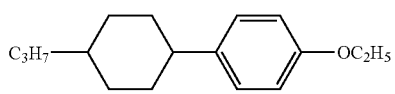 15%

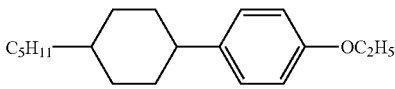 15%

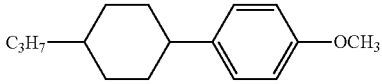 10%

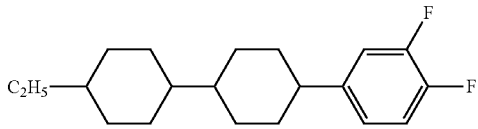 10%

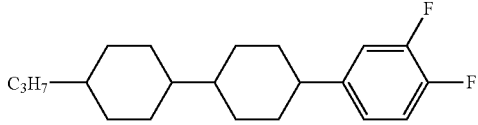 10%

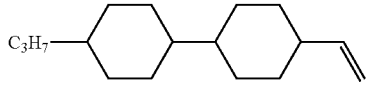 10%

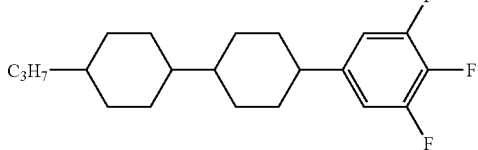 12%

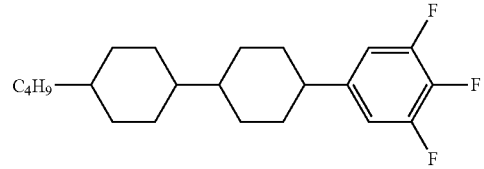 6%

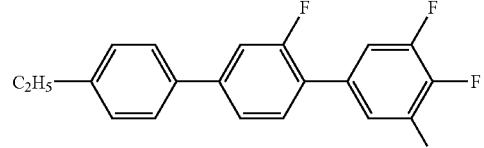 5%

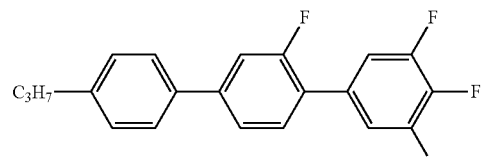 7%

Physical properties determination methods of liquid crystal compounds are in accordance with the industry norms, see "LCD Device Handbook," Aviation Industry Publishing House.

The method for measuring physical properties of the compound:

1. The determination of the phase structure and transfer temperature (° C.)

① melting point apparatus equipped with a polarizing microscope [Mettler Company FP-52 type], the compound is placed on a heating plate, while heating at a rate of 3°

C./min, while using a polarizing microscope to observe the phase change, so as to determine the phase species.

② using the differential calorimetry twist scanner DSC822e of Mettler company, heating or cooling at a rate of 1° C./min, using extrapolation to obtain the starting point of endothermic or exothermic peak crest associated with the phase change of the sample, so as to determine the transfer temperature.

a crystal is represented by C, a smectic phase is S, a nematic phase is N, the liquid is I.

2. The viscosity η is measured under 20° C. (mPa·s) by using E type rotary viscometer.

$\gamma_1$ is measured under 20° C. (cPa) by using ToYo6254 liquid crystal general-purpose Tester.

3. The optical anisotropy (refractive index anisotropy was measured at 25° C. (Δn)), which is measured by using an Abbe refractometer at 25° C. with a light with a wavelength of 589 nm (Δn). After the friction to the surface of the main prism (Prism) in one direction, the sample was added dropwise onto the main prism. The refractive index ($n_{||}$) is a obtained value measured when the direction of polarized light is parallel to the direction of friction, the refractive index ($n_\perp$) is a obtained value measured when the direction of polarized light is perpendicular to the direction of friction, the value of optical anisotropy (Δn) is calculated by $\Delta n = n_{||} - n_\perp$.

4. The dielectric constant anisotropy (ΔЄ, measured at 25° C.) is measured by HP4284a precision LCR meter of Hewlett-Packard Company. The dielectric constant Є|| in the major axis direction of the liquid crystal molecules is determined, the dielectric anisotropy ($Є_\perp$) in the minor axis direction of the liquid crystal molecules is determined, the dielectric anisotropy ΔЄ is calculated by $\Delta Є = Є_{||} - Є_\perp$.

In the measured values, when used the liquid crystal compound itself as a sample, the obtained values are recorded as the experimental value, when used the mixture of the liquid crystal compound and mother liquid as a sample, the values obtained by extrapolation are recorded as experimental value.

Example 1

Preparing the Compound Shown in Formula I-17 (Process I)

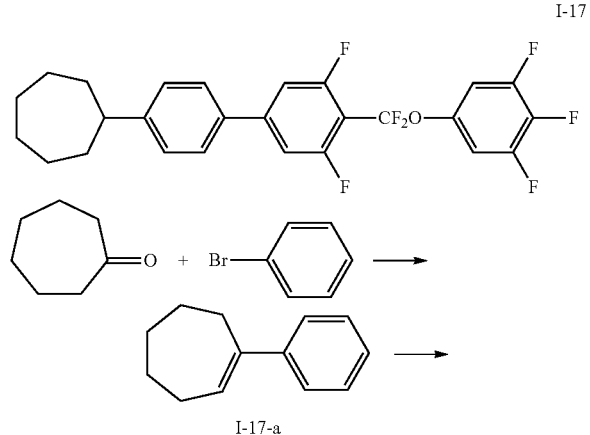

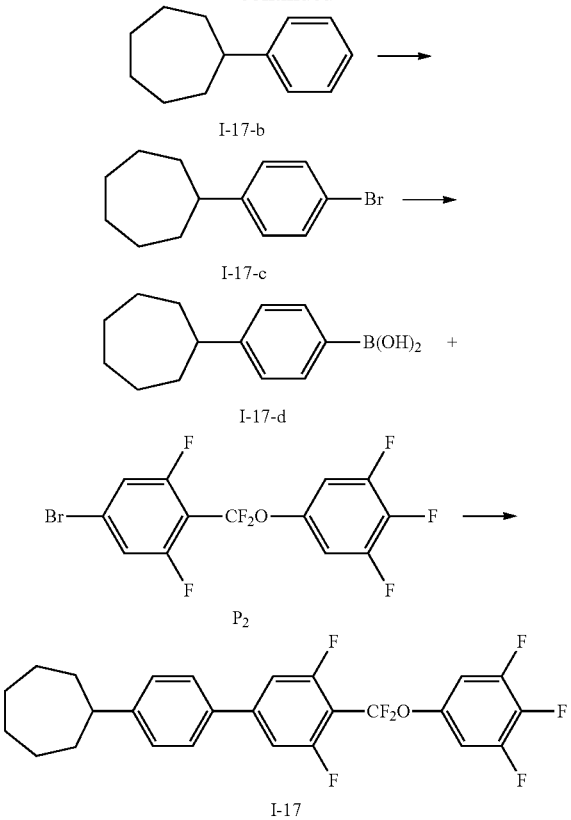

Step 1.1—The Preparation for Phenyl Cycloheptene (Formula I-17-a)

To a 2 L three-necked flask was added 29 g magnesium (reactant), 0.5 L tetrahydrofuran (solvent), 10 g bromobenzene (reactant), a grain of iodine, heating to initiate. After the initiation, adding dropwise the remaining 163 g bromobenzene (reactant), while maintaining micro refluxing. After the dropwise addition was completed, continuing to reflux for 1 hour. Again, adding dropwise 112 g cycloheptanone (reactant), after the dropwise addition, continuing to reflux for 1 hour. After the reaction was completed, the reaction liquid was poured into 2 L ice water, adding 120 g hydrochloric acid (reactant), stirring 10 minutes, and separating the liquids. Extracting the aqueous phase with 1 L toluene for three times, and combined with organic phase. The organic phase was washed with 2 L deionized water for three times, then adding 2 L toluene, 30 g Para-toluene sulphonic acid, heating to evaporate the low-boiling point solvent, when the temperature has risen to above 100° C., continuing to reflux for 5 h. Reduce the temperature to room temperature, added 1.5 L water for three times, the organic phase passed through a chromatographic column filled with 250 g silica gel, flushing the column with 1 L toluene. After concentration, distilling under reduced pressure to collect the fraction of 115-116° C. (10 mmHg), and 147 g product (formula I-17-a) was obtained, with a yield of 85%

Step 2. The preparation for phenyl cycloheptane (formula I-17-b)

To a 3 L three-necked flask was added 0.5 L ethanol (solvent), 147 g 1-phenyl cycloheptene (formula I-17-a) (reactant), 5 g 5% Pd/C (catalyst), hydrogenated under room temperature with stirring for 5 hours. After the reaction was completed, filtrating and the filtrate was obtained, the solvent was evaporated, distilling under reduced pressure to collect the fraction of 112-113° C. (10 mmHg), and 142.6 g product (formula I-17-b) was obtained, with a yield of 97%

Step 3. The Preparation for 1-(4-Bromophenyl) Cycloheptane (Formula I-17-c)

To a 5 L three-necked flask was added 142.6 g phenyl cycloheptane (formula I-17-b)(reactant), 10 g ferric trichloride (reactant), 0.5 L petroleum ether, 100 ml dichloromethane (solvent), cooling to 0° C. to 5° C., and the exhaust absorption device was installed. Adding dropwise 132 g liquid bromine (reactant), maintaining the temperature, and continued to react for 1 hour after the dropwise addition. The reaction liquid was poured into 1 L deionized water containing 10% sodium hydrogen sulfite, stirring for 20 minutes, and separating the liquids. Extracting the aqueous phase with 1 L toluene for three times, and combined with organic phase. The organic phase was washed with 2 L deionized water for three times. Drying by anhydrous sodium sulfate, concentrated, then passed through the chromatographic column (petroleum ether). Concentrated, the crude product was recrystallized with twice the ethanol, filtrating, then 99 g white solid 1-(4-bromophenyl) cycloheptane (formula I-17-c) was obtained, with a yield of 48%.

Step 4. The Synthesis of Cycloheptyl Phenylboronic Acid (Formula I-17-d)

To a reaction vessel was added 25.3 g (0.1 mol) 4-(cycloheptyl) p-bromobenzene (formula I-17-c)(reactant), 80 ml tetrahydrofuran (solvent), under the protection of nitrogen gases, cooling to −60° C., adding dropwise the petroleum ether (solvent) solution of 0.1 mol n-butyllithium (reactant), the dropwise addition will be finished within 1 hour, stirring to react for 30 minutes under −50° C. Then, cooling to −60° C., adding dropwise 70 ml tetrahydrofuran (solvent) solution of 13 g (0.13 mol) trimethyl borate (reactant) within 1 hour, after the addition, continuing to control the temperature and stirring to react for 1 hour, warming up to room temperature, adding 0.2 mol hydrochloric acid and stirring for 1 hour, after adding water to wash, extracting 50 ml ethyl acetate (solvent) and separating the liquids, washing the organic phase to become neutral, drying by distilling the solvent, 17.4 g compound (II-c) was obtained, with a yield of 80%, and a liquid chromatography purity of 97%.

Step 5 the Synthesis of the Compound Formula I-17

Figure 2:
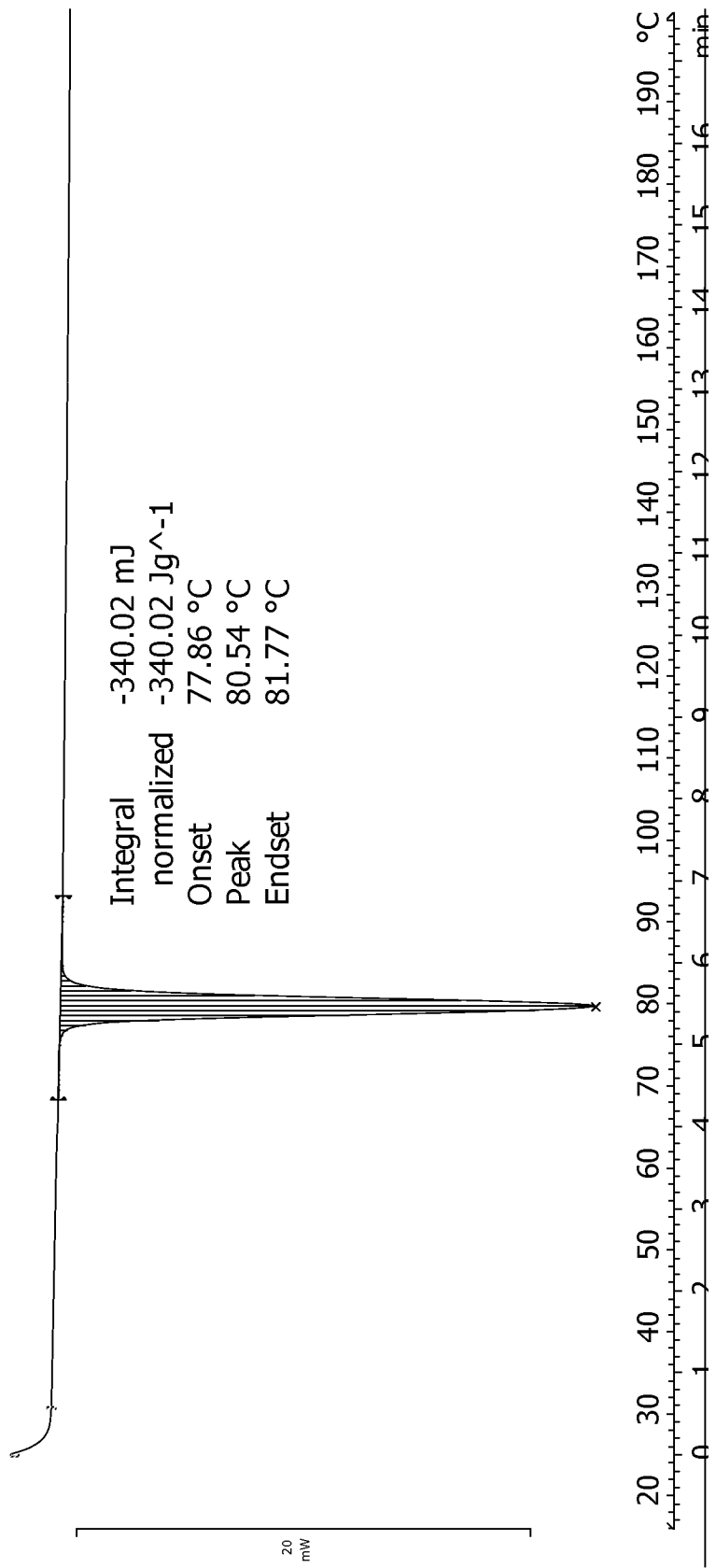
FIG. 2 is a differential thermal chart of the product of Example 1.

To a reaction vessel was added 24 g (0.11 mol) cycloheptyl phenylboronic acid (formula I-17-d)(reactant), 38.9 g (0.1 mol) gP2 (reactant)(according to Peer. K I rsch et al., Angew. Chem. I nt. Ed. 2001.40.1480. synthesis), 0.3 g tetra(triphenylphosphine)palladium (catalyst), 15 g sodium carbonate (catalyst), 100 ml toluene (solvent), 100 ml water, 100 ml ethanol (solvent), heating to reflux for 4 hours, adding 100 ml water, separating the liquids, distilling the organic phase to dryness, and experienced the column chromatography, recrystallize so as to obtain 33.7 g product of formula I-17, with a yield of 70%, the experimental results are as follows:

(1) GC: 99.9%;
(2) MP: 80.5° C.;
(3) MS: m/s % 482 (2.6), 335 (100), 252 (3.2), 265 (5.4);
(4) $^1$H-NMR: δ(ppm) 1.50 (m, 10H), 1.71 (m, 2H), 2.76 (m, 1H) 6.89 (m, 2H), 7.22 (d, 2H), 7.37 (s, 4H);

The mass spectrogram is shown in FIG. 1.
The differential thermal chart is shown in FIG. 2.
It can be seen from the above that the structure of the product is right, belong to the target product of formula I.

The measurement results of liquid crystal properties and viscosity of the product are as follows:

(5) Δ∈: 20.28V;
(6) Δn: 0.128.
(7) η: 56.0.

It can be seen from the above that the product is stable to light and heat, with wider nematic phase, a wider liquid crystal state temperature range, and a better low temperature miscibility.

Example 2

Preparing the Compound Shown in Formula I-21 (Process I)

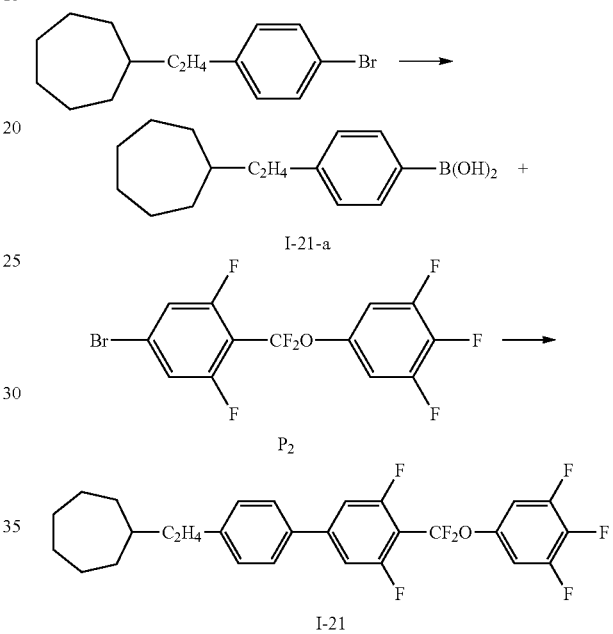

Step 1. The Synthesis of Cycloheptyl Ethyl Phenylboronic Acid

To a reaction vessel was added 27.7 g (0.1 mol) 4-bromophenyl ethyl cycloheptane (reactant), 80 ml tetrahydrofuran (solvent), under the protection of nitrogen gases, cooling to −60° C., adding dropwise the petroleum ether (solvent) solution of 0.1 mol n-butyllithium (reactant), the dropwise addition will be finished within 1 hour, stirring to react for 30 minutes under −50° C. Then, cooling to −60° C., adding dropwise 70 ml tetrahydrofuran (solvent) solution of 13 g (0.13 mol) trimethyl borate (reactant) within 1 hour, after the addition, continuing to control the temperature and stirring to react for 1 hour, warming up to room temperature, adding 0.2 mol hydrochloric acid and stirring for 1 hour, after adding water to wash, extracting 50 ml ethyl acetate (solvent) and separating the liquids, washing the organic phase to become neutral, drying by distilling the solvent, 19.4 g of the compound (II-c) was obtained, with a yield of 80%, and the purity by liquid chromatography is 97%.

Step 2. The Synthesis of the Compound 1-21

To a reaction vessel was added 26.6 g (0.11 mol) cycloheptyl ethyl phenylboronic acid (reactant), 38.9 g (0.1 mol)g P$_2$(reactant) (according to Peer. K I rsch et al., Angew. Chem. I nt. Ed.2001.40.1480. synthesis), 0.3 g tetra(triphenylphosphine)palladium (catalyst), 15 g sodium carbonate (catalyst), 100 ml toluene (solvent), 100 ml water, 100 ml ethanol (solvent), heating to reflux for 4 hours, adding 100 ml water, separating the liquids, distilling the organic phase to dryness, and by column chromatography, recrystallize it so as to obtain 35.4 g product 1-21, with a yield of 70%.

The experimental results are as follows:
(1) GC: 99.9%
(2) MP: 47° C.
(3) MS: m/s % 510 (0.8), 363 (35.2), 253 (100), 97 (1.3)
(4) $^1$H-NMR: δ(ppm) 1.12 (m, 2H), 1.50 (m, 13H), 2.62 (t, 2H), 6.89 (m, 2H), 7.22 (d, 2H), 7.38 (m, 4H)

It can be seen from the above that the structure of the product is right, belong to the target product of formula I.

The measurement results of liquid crystal properties and viscosity of the product are as follows:
(5) Δ∈: 21.0V;
(6) Δn: 0.128.
(7) η: 76.0.

It can be seen from the above that the product is stable to light and heat, with wider nematic phase, a wider liquid crystal state temperature range, and a better low temperature miscibility.

Example 3

Preparing the Compound Shown in Formula I-20 (Process II)

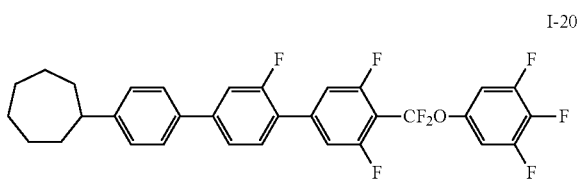
I-20

Step 1

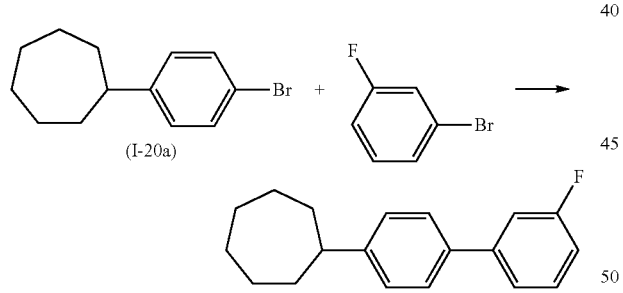

To a reaction vessel was added 0.1 mol 1-(4-bromophenyl) cycloheptane, 0.12 mol m-fluorophenyl boronic acid (reactant), 0.3 mol potassium carbonate (reactant), 80 ml toluene (solvent), 60 ml ethanol (solvent), 60 ml water (solvent), under the protection of nitrogen gases, adding 0.4 g tetra(triphenylphosphine)palladium (catalyst), heating with stirring to refluxing reaction for 3 hours. Cooling to room temperature, separating the liquids, extracting aqueous phase with 50 ml toluene (solvent), the organic phase was combined and washed to become natural. Drying by distilling the solvent, with the resultant dissolved in 100 ml toluene, decolorized by the silica gel column, eluting with toluene (solvent), collecting the eluent and drying by distilling the solvent, freeze recrystallize under −20° C. after dissolved with triple petroleum ether, suction filtration, so as to obtain white crystals (I-20-a). With a yield of 90%, the purity by gas chromatography is 99.5%.

Step 2

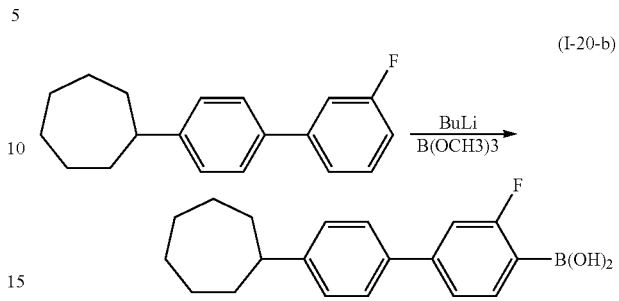

To a reaction vessel was added 0.1 mol (I-20-a)(reactant), 0.11 mol potassium tert-butoxide, 80 ml tetrahydrofuran (solvent), under the protection of nitrogen gases, cooling to −90° C., adding dropwise the petroleum ether (solvent) solution of 0.12 mol n-butyllithium (reactant), the dropwise addition will be finished within 1 hour, stirring to react for 30 minutes under −90° C. Still control the temperature to −90° C., adding dropwise 70 ml tetrahydrofuran (solvent) solution of 0.11 mol trimethyl borate (reactant) within 1 hour, after the addition, continuing to control the temperature and stirring to react for 1 hour, warming up to 0° C., adding 100 ml water and 20 ml concentrated hydrochloric acid, stirring for 20 minutes, separating the liquids, extracting petroleum ether (solvent) and separating the liquids, washing the organic phase to become neutral, after drying by distilling the solvent, freeze recrystallize under −20° C. after heated and dissolved with twice petroleum ether, suction filtration, so as to obtain white crystals (I-20-b). With a yield of 60%, the purity by gas chromatography is 99.5%.

Step 3

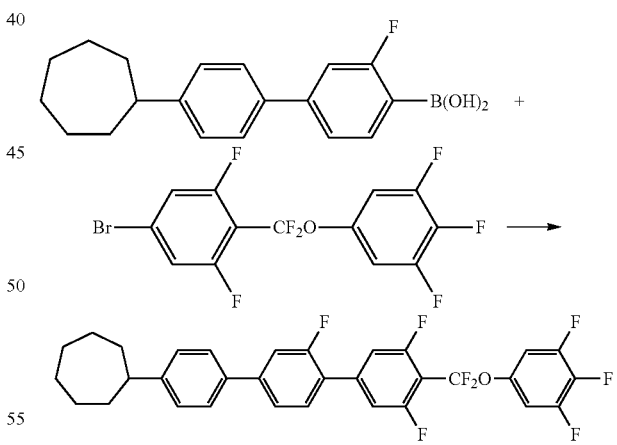

Figure 3:
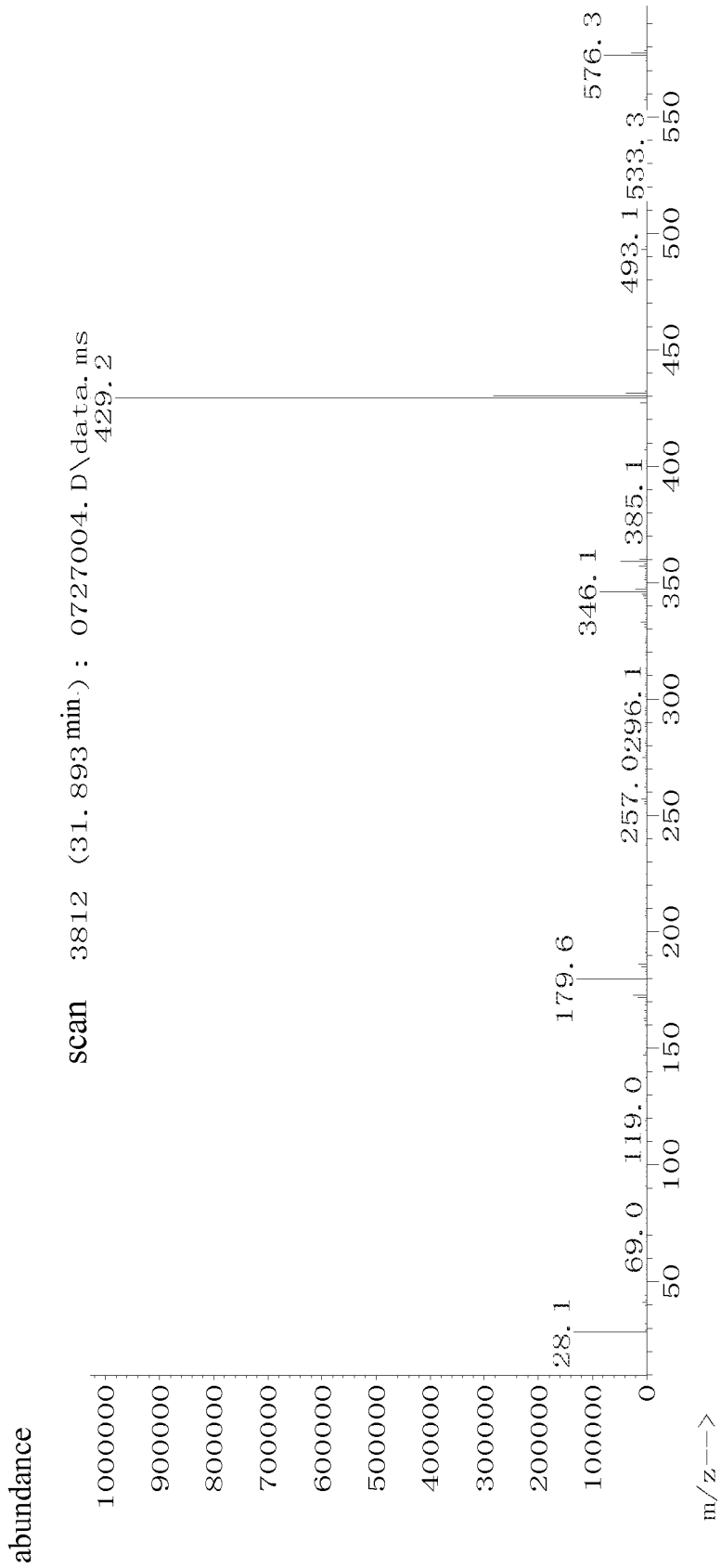
FIG. 3 is a mass spectrogram of the product of Example 3.
Figure 4:
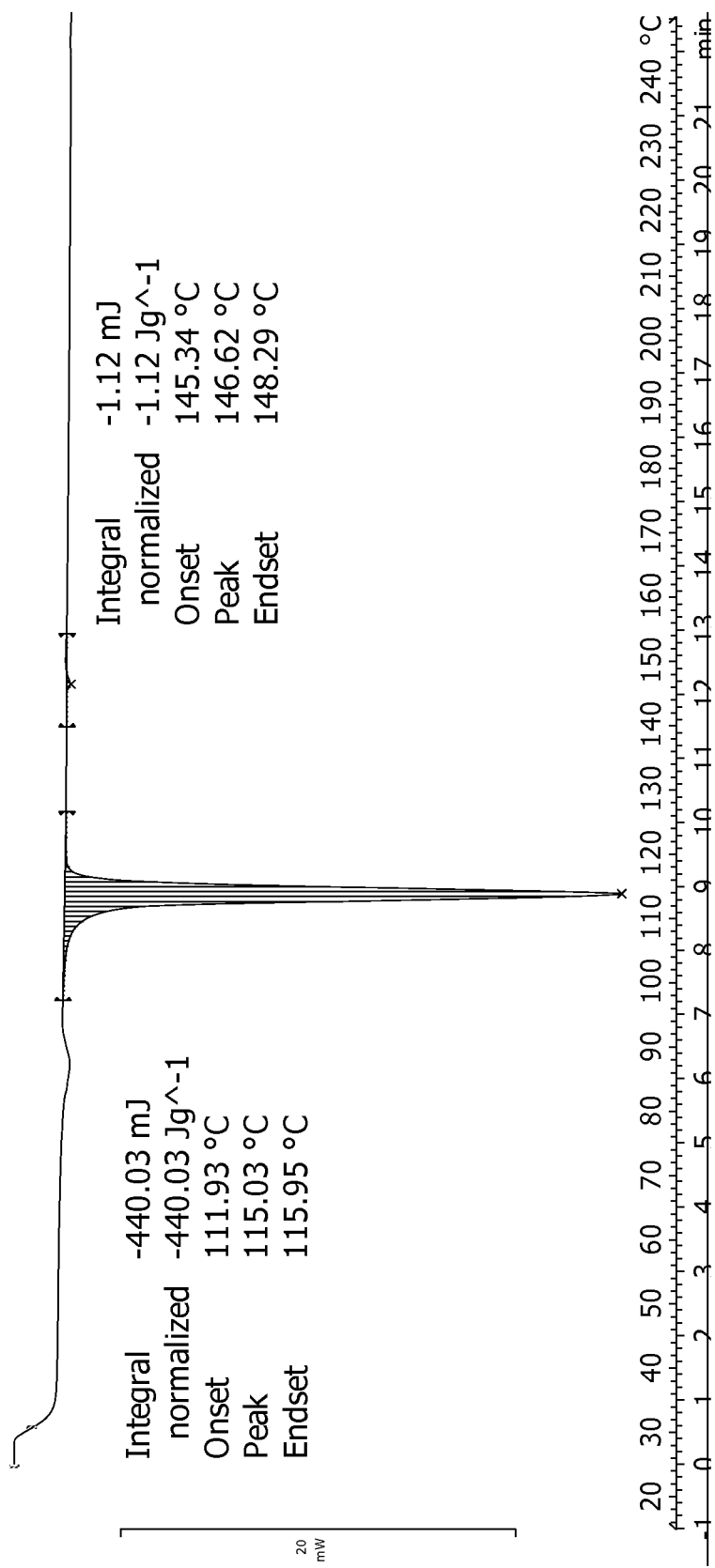
FIG. 4 is a differential thermal chart of the product of Example 3.

To a reaction vessel was added 34.3 g (0.11 mol) I-20-b (reactant), 38.9 g (0.1 mol) P 2 (reactant) (according to Peer. K I rsch et al., Angew. Chem. I nt. Ed.2001.40.1480. synthesis), 0.3 g tetra(triphenylphosphine)palladium (catalyst), 15 g sodium carbonate (catalyst), 100 ml toluene (solvent), 100 ml water, 100 ml ethanol (solvent), heating to reflux for 4 hours, adding 100 ml water, separating the liquids, distilling the organic phase to dryness, and experienced the column chromatography, recrystallize so as to obtain 40.3 g product 1-20, with a yield of 70%, The experimental results are as follows:
(1) GC: 99.9%;
(2) MP: 115° C.; CP: 146.6° C.
(3) MS: m/s % 576 (7.7), 429 (100), 346 (8.4), 359 (4.8);
(4) ¹H-NMR: δ(ppm) 1.50 (m, 10H), 1.71 (m, 2H), 2.76 (m, 1H) 6.89 (m, 2H), 7.02 (d, 1H), 7.22 (d, 2H), 7.37 (s, 4H), 7.58 (d, 1H), 7.83 (m, 1H);

The mass spectrogram is shown as in FIG. 3.
The differential thermal chart is shown as in FIG. 4.
It can be seen from the above that the structure of the product is right, belong to the target product of formula I.
The measurement results of liquid crystal properties and viscosity of the product are as follows:
(5) Δ∈: 19.8V;
(6) Δn: 0.198.
(7) η: 154.0.

It can be seen from the above that the product is stable to light and heat, with wider nematic phase, a wider liquid crystal state temperature range, and a better low temperature miscibility.

Example 4

Preparing the Compound Shown in Formula I-19 (Process III)

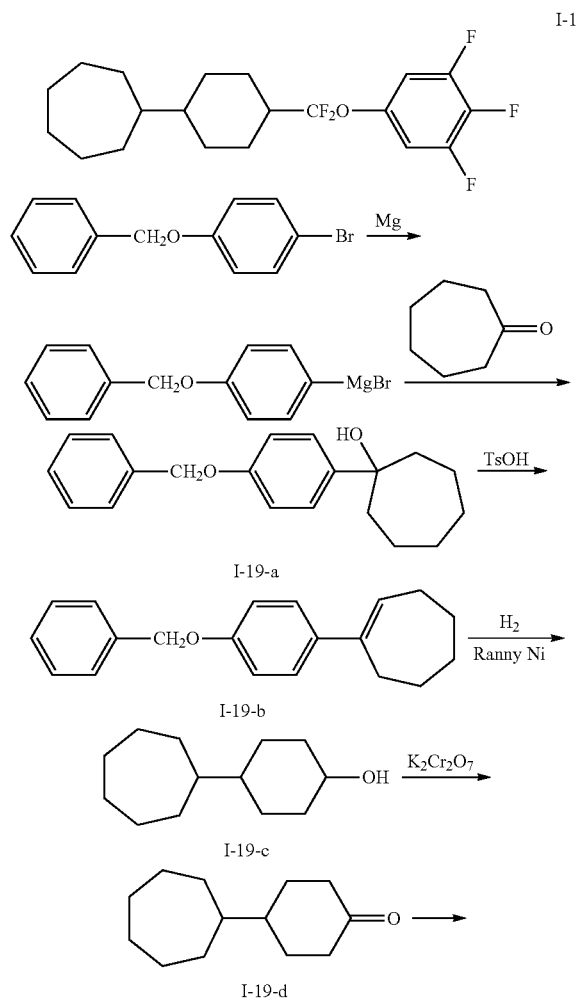

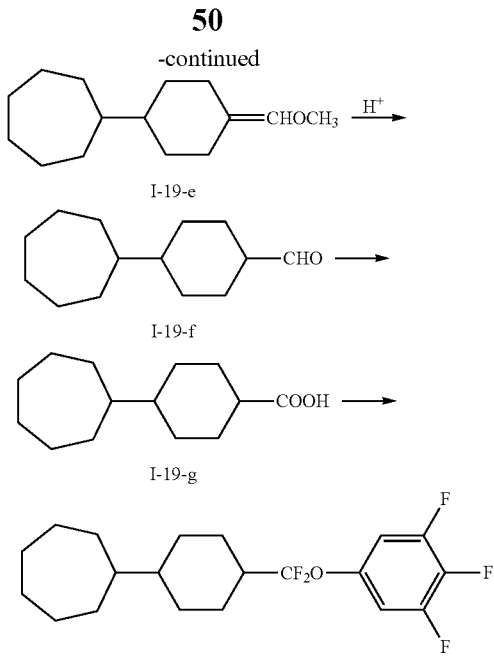

Step 1. The Synthesis of (I-19-a)

To a 2 L three-necked flask was added 28.8 g (1.2 mol) freshly prepared magnesium turnings (reactant) and 200 ml dried tetrahydrofuran (solvent), a grain of iodine (initiator), heating to refluxing, adding dropwise a small amount of solution that dissolved 263 g (1 mol) benzyloxy bromobenzene (reactant) with 500 ml dried tetrahydrofuran (solvent), after initiating the Grignard reaction, maintaining the reaction slightly refluxing, continuing to add dropwise, then maintaining the refluxing for 30 minutes, adding dropwise 112 g (1 mol) cycloheptanone (reactant), maintaining the reaction slightly refluxing, then maintaining the refluxing for 30 minutes after the dropwise addition, cooling to room temperature, pouring into the mixed liquor of 1 kg ice (hydrolysis), 300 ml toluene and 3 mol hydrochloric acid (hydrolysis) under stirring, stirring for 30 minutes, separating the liquids, take the upper layer organic phase, extracting aqueous phase by 300 ml toluene, washing the organic phase 3 times with 1 L deionized water, after dried by anhydrous sodium sulfate, removing the solvent by vacuum water bath distillation, and 290 g (I-19-a) colourless liquid was obtained.

Step 2. The Synthesis of (I-19-b)

To a 2 L three-necked flask was added 290 g (I-19-a) (reactant) prepared last step, 20 g p-toluenesulfonic acid (dehydrant), 1 L toluene (solvent), the refluxing water distribution stopped after 3 hours, cooling to room temperature, adding 200 ml saturated sodium bicarbonate solution, separating the liquids after stirring for 10 minutes, take the upper layer organic phase, washing the organic phase twice with 500 ml deionized water, the anhydrous sodium sulfate conducted the column chromatography directly by 10 cm silica gel column after it has been dried, then using 200 ml toluene to elute, clean the solvent by water bath vacuum distillation, adding the mixed solvent of 200 ml toluene and 400 ml ethanol to recrystallize, precipitating at room temperature, filtration after freeze 4 h in the freezer, so as to obtain 244.6 g (0.88 mol)(I-19-b), GC: 99.4%, with a yield of 88%.

Step 3. The Synthesis of (I-19-c)

To a 2 L three-necked flask was added 244.6 g (0.88 mol)(I-19-b)(reactant) prepared last step, 500 ml of absolute ethyl alcohol (solvent), 60 g Raney nickel catalyst, installed vessel lid of the autoclave, with hydrogen exhaust air 5 times, increase hydrogen pressure inside the autoclave to 3.5 Mpa, heated to 120° C., a hydrogenation reaction was stirred for 13 hours, the reaction was completed, cooling to 40° C. or less, and Raney nickel was removed by filtration, washed the Raney nickel with 160 g of anhydrous ethanol and the filtrate was rotary evaporated and net of the solvent, and a pale yellow liquid of 164.6 g (0.84 mol) (I-19-c) was obtained, GC: 99.6%, with a yield of 95.4%.

Step 4. The Synthesis of (I-19-d)

To a 5 L three-necked flask was added 164.6 g (0.84 mol)(I-19-c) (reactants), 1.5 L of anhydrous diethyl ether (solvent), 610 ml acetone (solvent) and stirred until dissolved, cooling to 0° C.; preparing the solution with 600 g of concentrated sulfuric acid, 310 g of potassium dichromate and 1.5 L of deionized water, and the reaction temperature was maintained at 0 to 5° C., adding dropwise to the three-necked flask, for about 1.5 hours the addition was completed. Hydrolysis and take the upper organic phase, the organic phase was washed with saturated sodium bicarbonate solution to weakly alkaline, and then the organic phase was washed with water until neutral, the solvent was removed by rotary evaporation, distillation under reduced pressure, so as to obtain a colorless liquid of 151.3 g (I-19-d) (0.78 mol), GC: 97.8%, with a yield of 92.8%.

Step 5. The synthesis of (I-19-e)

To a 1 L three-necked flask was added 400 mL of tetrahydrofuran (solvent), 150 g (0.35 mol) chlorine ether triphenylphosphine salt (reactant), cooling to 0° C. under stirring, adding 39 g (0.35 mol) potassium tert-butoxide (reactant) in batches, stirring for 1 hour after the addition was completed, adding dropwise the solution of 31 g (0.16 mol)(I-19-c)(reactant) and 200 ml tetrahydrofuran (solvent), stirring for 1 hour after the dropwise addition was completed, adding 200 ml water, stirring for 10 minutes, separating the liquids, and netting of the solvent by distillation. 32 g (0.14 mol) of the product (I-19-e) of crude product column chromatography was obtained, GC: 98%, with a yield of 90%.

Step 6. The synthesis of (I-19-f)

To a 500 mL three-necked flask was added 32 g (0.14 mol)(I-19-e) (reactant), 200 mL tetrahydrofuran (solvent), cooling to 5° C., adding dropwise 120 g hydrochloric acid with a concentration of 20%, stirring for 4 hours under room temperature after the dropwise addition was completed, adding 200 mL of dichloromethane (solvent), stirring to make the reaction liquid clear, separating the liquids, extracting the aqueous phase with 100 ml of dichloromethane (solvent), washing the organic phase to become natural, drying by distilling the solvent, a faint yellow solid of 29.2 g was obtained, GC: 95%, with a yield of 100%.

To another 1 L three-necked flask was added 400 mL absolute methanol (solvent), 6 g potassium hydroxide (catalyst), adding above reaction product (reactant) after stirring to dissolve, cooling to 0° C. to 10° C., and maintaining the temperature and stirring for 4 hours, adding 400 mL of dichloromethane (solvent), stirring to make the reaction liquid clear, separating the liquids, extracting the aqueous phase with 100 ml of dichloromethane (solvent), washing the organic phase to become natural, drying by distilling the solvent, a faint yellow solid (I-19-f) of 26.3 g (0.13 mol) was obtained, GC: 90%, with a yield of 90%.

Step 7 cycloheptyl cyclohexyl formate (I-19-g)

To a 5 L three-necked flask was added 176.4 g (0.84 mol)(I-19-f)(reactant), 610 ml acetone (solvent), stirring to dissolve, cooling to 0° C., preparing the solution with 84 g concentrated sulfuric acid, 132 g potassium hypermanganate, 1.5 L deionized water, and the reaction temperature is maintained at 0 to 5° C., adding dropwise to the three-necked flask, for about 1.5 hours the addition was completed. Hydrolysis and take the upper organic phase, the organic phase was washed with saturated sodium bicarbonate solution to the black solid disappeared, filtration and obtained a white solid, washing with water again to become neutral, drying off and 123.5 g of cycloheptyl cyclohexyl formate (I-19-g) was obtained, with a yield of 70%.

Step 8

To a reaction vessel was added 0.1 mol (I-19-g), 30 ml of toluene (solvent) and 30 ml of isooctane (solvent), adding 14 g 1,3-propanedithiol (reactant), heating above suspension to 50° C. under stirring, adding 19.2 g trifluoromethanesulfonic acid (reactant) within 30 minutes, warming up to reflux after the addition, separating the produced water, cooling to 90° C. after separating the water completely, adding 100 ml of methyl tertiary butyl ether (solvent) within 45 minutes under the temperature between 70 to 90° C., continuing to reduce the temperature, precipitating the crystals, filtration under the protection of nitrogen gases, washing the obtained crystals with methyl tertiary butyl ether (solvent)(25 ml×4), after vacuum drying, an orange crystals (dithiane trifluoromethanesulfonate) was obtained.

To a reaction vessel was added a mixed solution of 0.1 mol 3,4,5-trifluorophenol (reactant), 0.1 mol triethylamine (reactant) and 130 ml dichloromethane (solvent), and cooling to −70° C., adding dropwise the solution of 120 ml dichloromethane (solvent) of above 0.1 mol (4-b) crystals (reactant), for 45 minutes the addition was completed, after stirring for 1 hour under this temperature, adding 0.4 mol NEt$_3$.3HF (reactant) within 5 minutes. Then, adding the solution of 30 ml dichloromethane (solvent) of 0.4 mol liquid bromine (reactant) within 1 hour under −70° C., then continuing to react for 1 hour under −70° C. T, warming up to 0° C., pouring the reaction liquid into 160 ml sodium hydroxide aqueous solution with a concentration of 32% (adjusting the pH value) and 300 g ice, adjusting the pH value of the reaction liquid to 5-8 through adding dropwise about 45 g of 32% sodium hydroxide aqueous solution. Extracting the aqueous phase with 80 ml dichloromethane (solvent) after separating the liquids, combining organic phase, and filtration with 4 g diatomite (decolorising agent), washing with water, drying by distilling the solvent under a reduced pressure. Recrystallizing the petroleum ether (solvent) after the column chromatography of the result crude product, so as to obtain a white crystal product (I-19), with a yield of 45%, GC: 99.8%.

(1) MP: 53° C.

(2) MS: m/s % 376 (97.3) 228 (100) 148 (72.5) 95 (98.6)

(3) $^1$H-NMR: δ(ppm) 1.27 (m, 6H), 1.43 (m, 16H), 2.48 (m, 1H) 6.89 (m, 2H)

It can be seen from the above that the structure of the product is right, belong to the target product of formula I.

The measurement results of liquid crystal properties and viscosity of the product are as follows:

(5) Δ∈: 12.0V;

(6) Δn: 0.087.

(7) η: 77.0.

It can be seen from the above that the product is stable to light and heat, with wider nematic phase, a wider liquid crystal state temperature range, and a better low temperature miscibility.

Example 5

Preparing the Compound Shown in Formula I-18 (Synthesis Route IV)

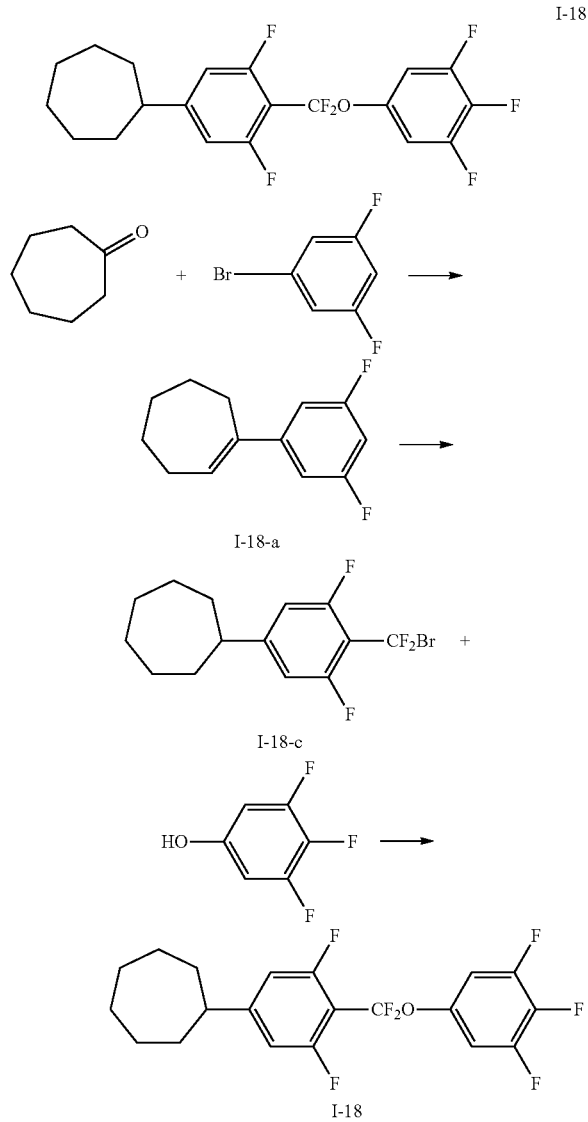

Step 1

A 1 L three-necked flask was added 6.3 g magnesium powder (reactant), 200 ml drying tetrahydrofuran (solvent), under the protection of nitrogen gases, heating to reflux, adding dropwise 46.3 g (0.24 mol) 3,5-difluorobromobenzene (reactant), refluxing for 1 hour after the dropwise addition was completed, adding dropwise a mixed solution of 0.216 mol cycloheptanone (reactant) and 50 ml drying tetrahydrofuran (solvent), stirring to reflux for 30 minutes after the addition, cooling to about 0° C., adding dropwise 200 ml of water and 30 ml of concentrated hydrochloric acid solution (adjusting the pH value), separating the liquids, extracting the aqueous phase with 200 ml toluene (solvent), washing the organic phase, separating the liquids, distilling to 110° C. under the constant pressure, supplement 100 ml toluene, adding 10 g p-toluenesulfonic acid, refluxing water distribution for 5 hours, adding 200 ml of water, separating the liquids, washing the organic phase to become neutral, so as to obtain 43 g (GC:86%) liquid (I-18-a).

Step 2:

To a reaction vessel was added (I-18-a) product, 400 ml ethanol (solvent), 5 gPd/C (catalyst), hydrogenation under constant pressure for 8 hours, filtration to remove catalyst, drying by distilling the solvent, a faint yellow oily matter was obtained, distillation under reduced pressure to obtain the product (I-18-b), with a purity of 98%

Step 3:

To a reaction vessel was added 0.1 mol (I-18-b) (reactant), 200 ml tetrahydrofuran (solvent), under the protection of nitrogen gases, cooling to −60° C., adding dropwise 0.11 mol n-butyllithium (reactant), during the adding dropwise the temperature is controlled at −55° C.~−60° C., after adding, continuing to control the temperature and stirring to react for 1 hour. Cooling to −70° C., adding dropwise 0.15 mol difluorodibromomethane (reactant), during the adding dropwise the temperature is controlled at −65° C.~−70° C., after adding, continuing to control the temperature and stirring to react for 30 minutes, warming up to room temperature, adding 20 ml concentrated hydrochloric acid (adjusting the pH value) and 50 ml water (solvent) to hydrolyze, separating the liquids, extracting the aqueous phase with 100 ml dichloromethane (solvent), washing the organic phase to become neutral, drying by distilling the solvent to obtain a faint yellow liquid (I-18-c), the purity by gas chromatography is 66%.

Step 4:

To a reaction vessel was added 0.1 mol (I-18-c) (reactant), 100 ml DMSO (solvent), 0.2 mol anhydrous potassium carbonate (reactant), 0.12 mol 3,4,5-trifluorophenol (reactant), heating with stir to 65~70° C. to react for 2 hours. Cooling to room temperature, filtering the solids, and washing the filter cake with 30 ml dichloromethane (solvent), adding 100 ml water to the filtrate, stirring, separating the liquids, extracting the water layer with 200 ml dichloromethane (solvent), washing the organic phase to become neutral, drying by distilling the solvent. The concentrate is dissolved in 500 ml toluene (solvent), decolorized by the silica gel column, eluting with toluene (solvent), collecting eluent and removing the solvent by distillation, recrystallize the resultant 3 times with absolute ethyl alcohol (solvent), so as to obtain a white needle crystal (I-18), with a yield of 40%, the purity by gas chromatography is 99.8%.

The structural verification data of the product are as follows:

(1) MP: 47.8° C.

(2) MS: m/s % 406 (0.05) 259 (100) 189 (18.4) 176 (7.3) 163 (41.1)

(3) $^1$H-NMR: δ(ppm) 1.51 (m, 10H), 1.71 (m, 2H), 2.76 (m, 1H) 6.54 (d, 2H), 6.89 (m, 2H)

Figure 5:
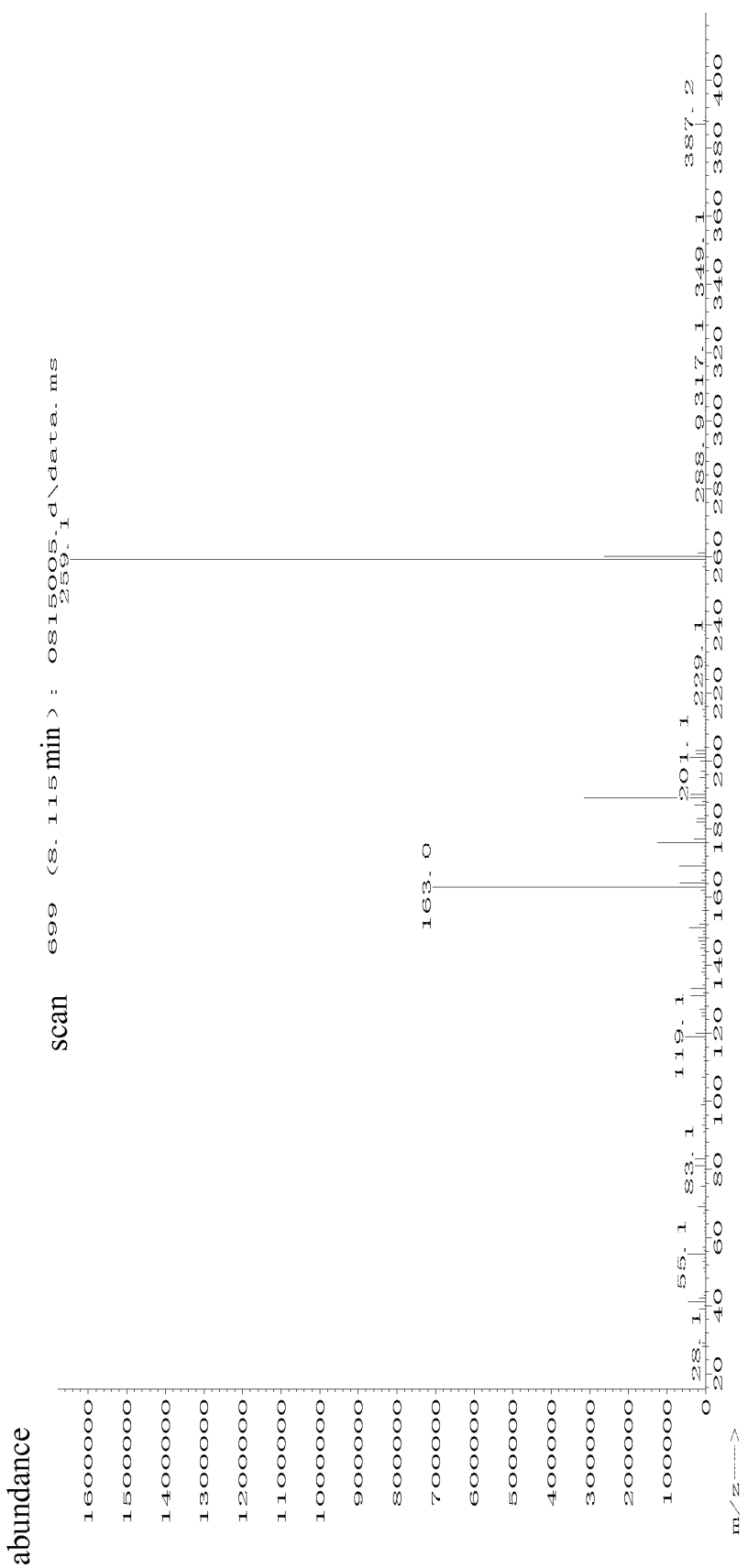
FIG. 5 is a mass spectrogram of the product of Example 5.

The mass spectrogram is shown as in FIG. 5.

Figure 6:
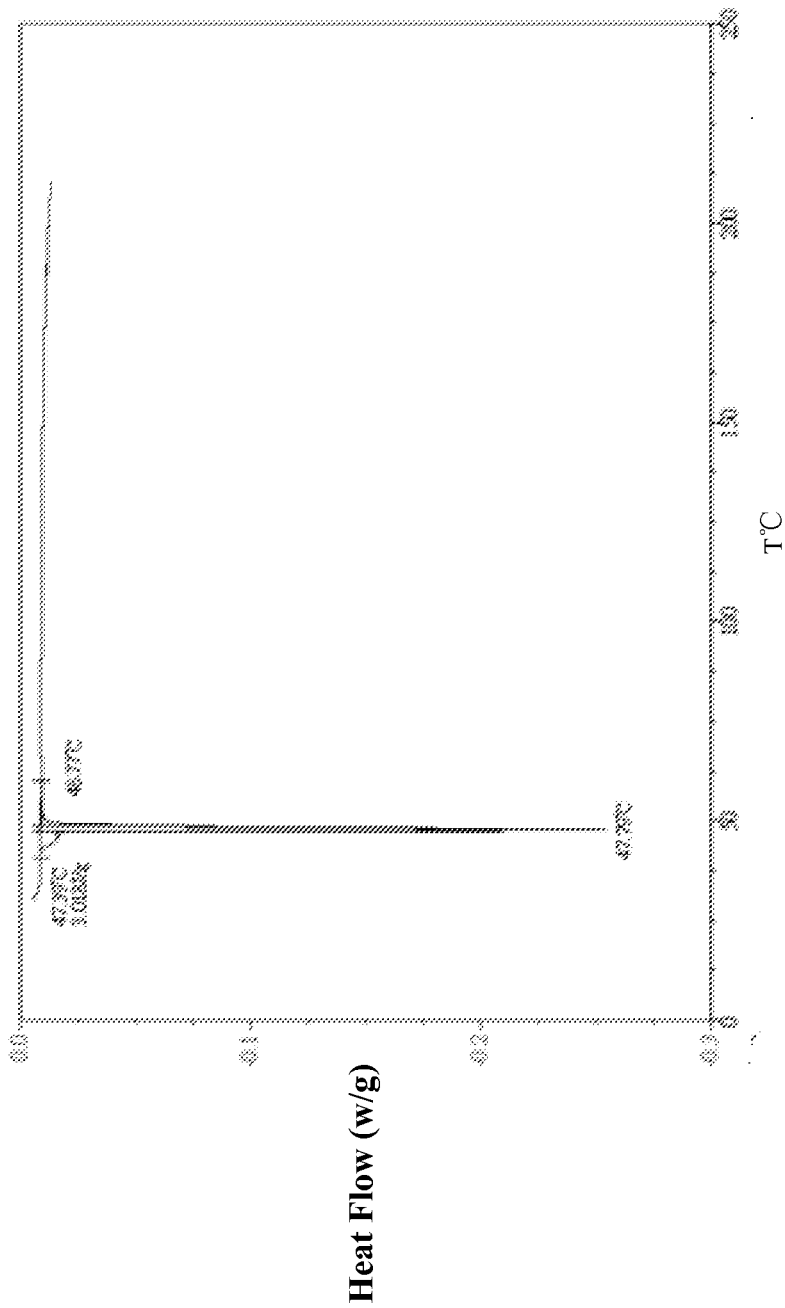
FIG. 6 is a differential thermal chart of the product of Example 5.

The differential thermal chart is shown as in FIG. 6.

It can be seen from the above that the structure of the product is right, belong to the target product of formula I.

The measurement results of liquid crystal properties and viscosity of the product are as follows:

(5) Δ∈: 18.0V;

(6) Δn: 0.12.

(7) η: 64.0.

It can be seen from the above that the product is stable to light and heat, with wider nematic phase, a wider liquid crystal state temperature range, and a better low temperature miscibility.

According to the method of the preceding Examples 1-5, except for corresponding substitution of the substituent of the reactant with the substituent of the target product, so as to obtain the following compounds belonging to formula I:
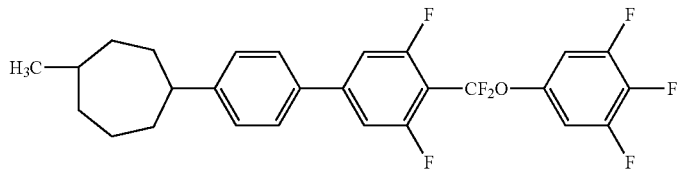
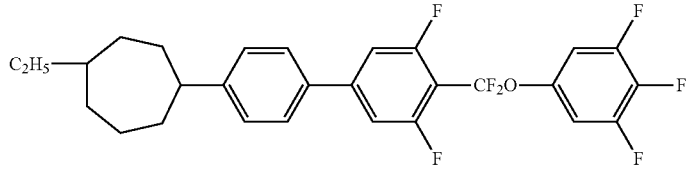
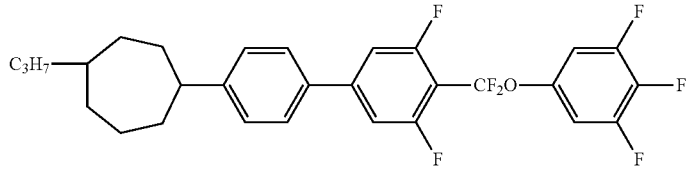
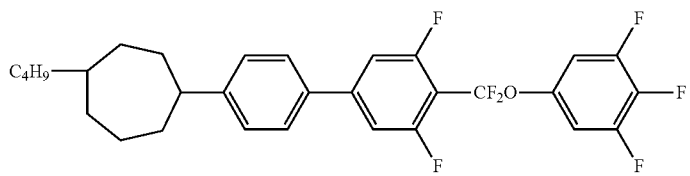
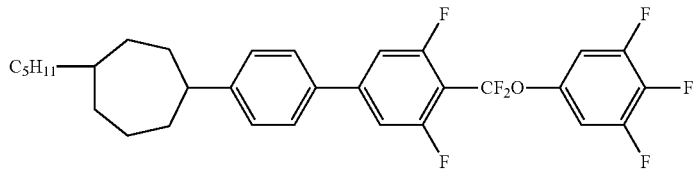
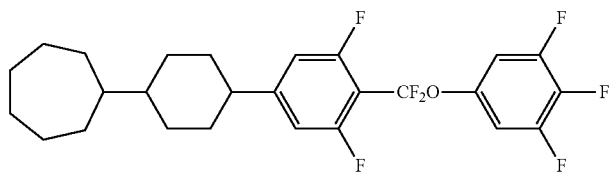
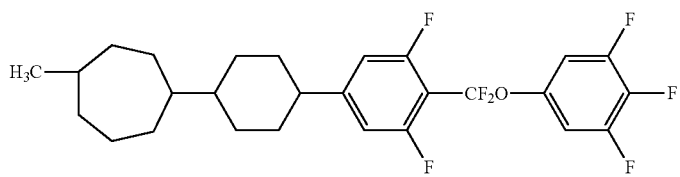
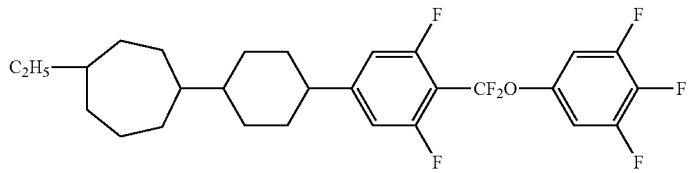
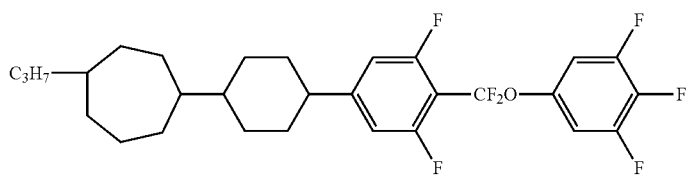

-continued
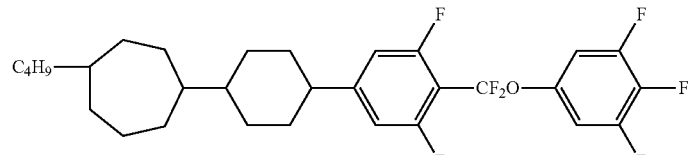
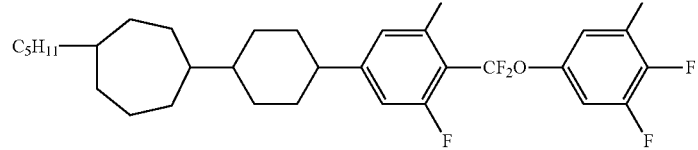
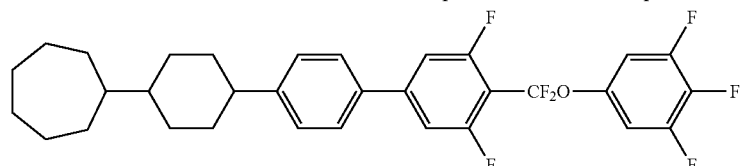
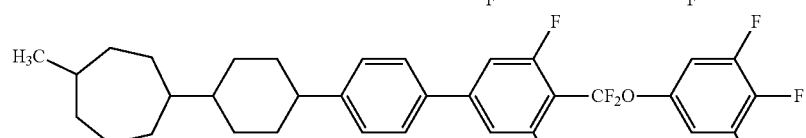
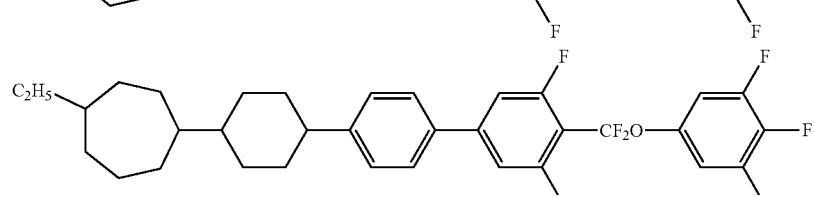
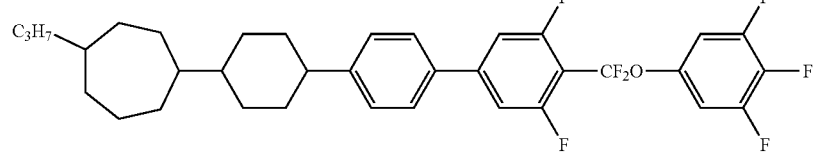
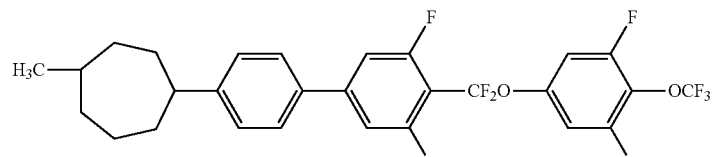
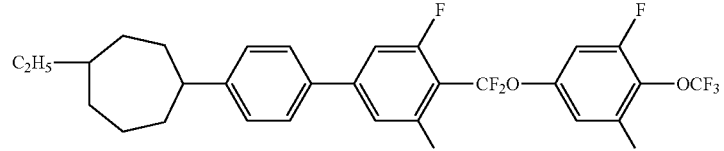
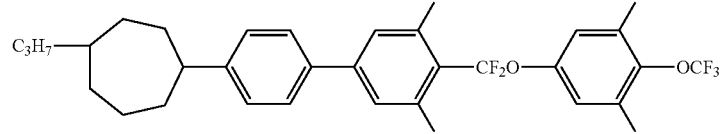
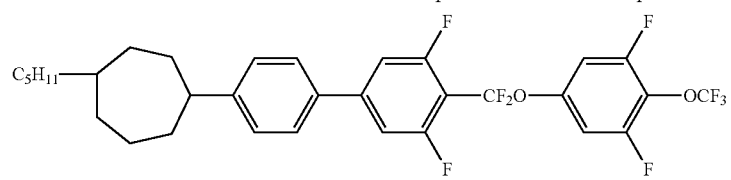

-continued
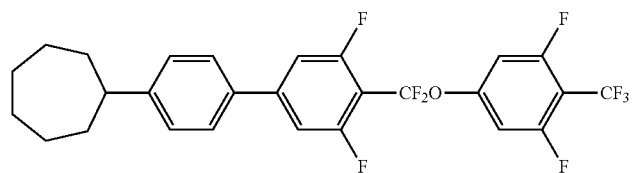
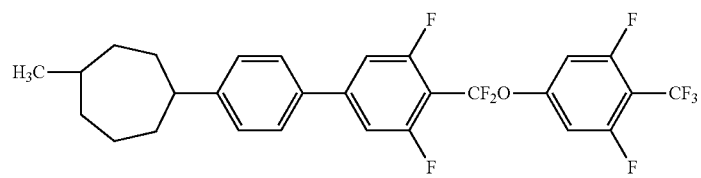
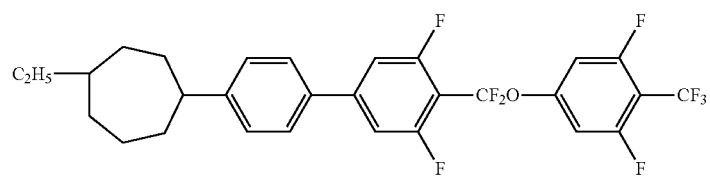
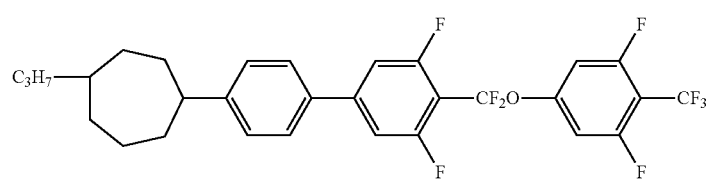
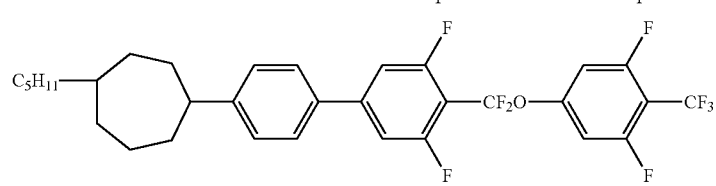
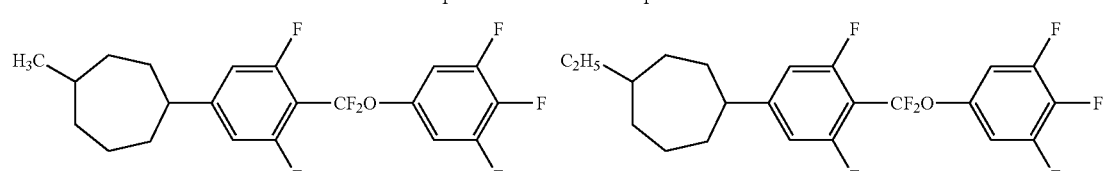
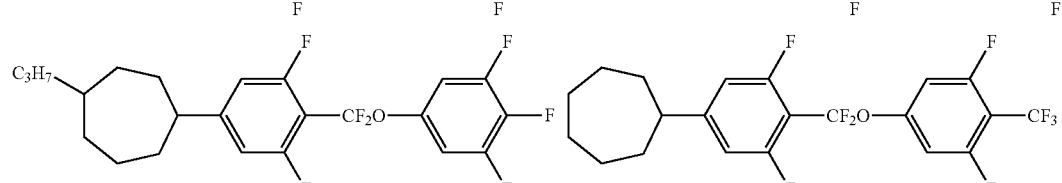
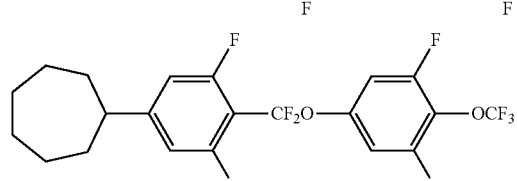
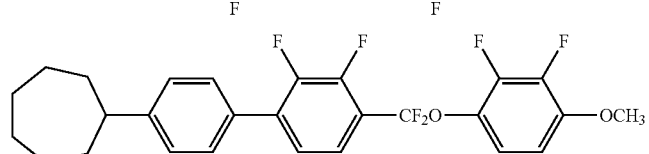
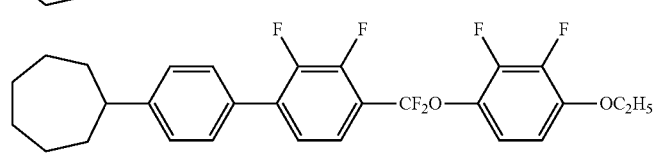

-continued
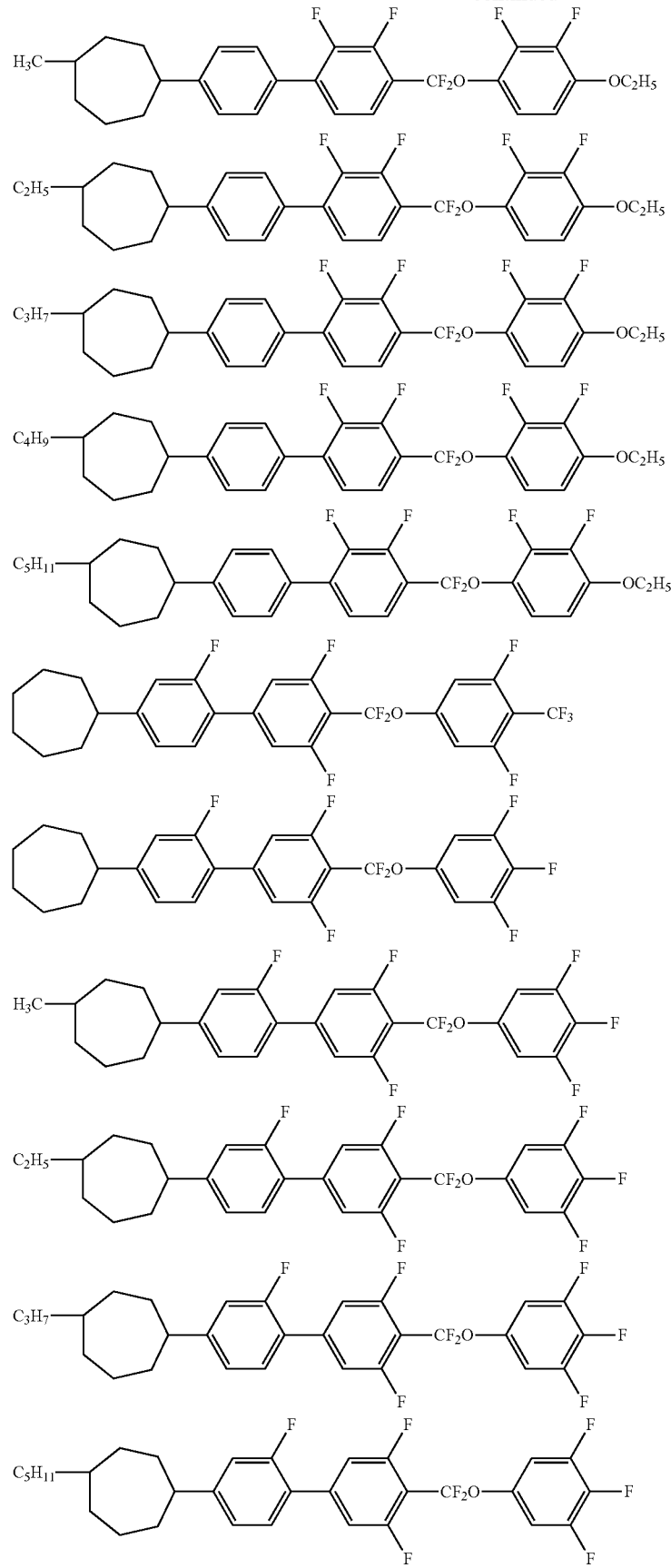

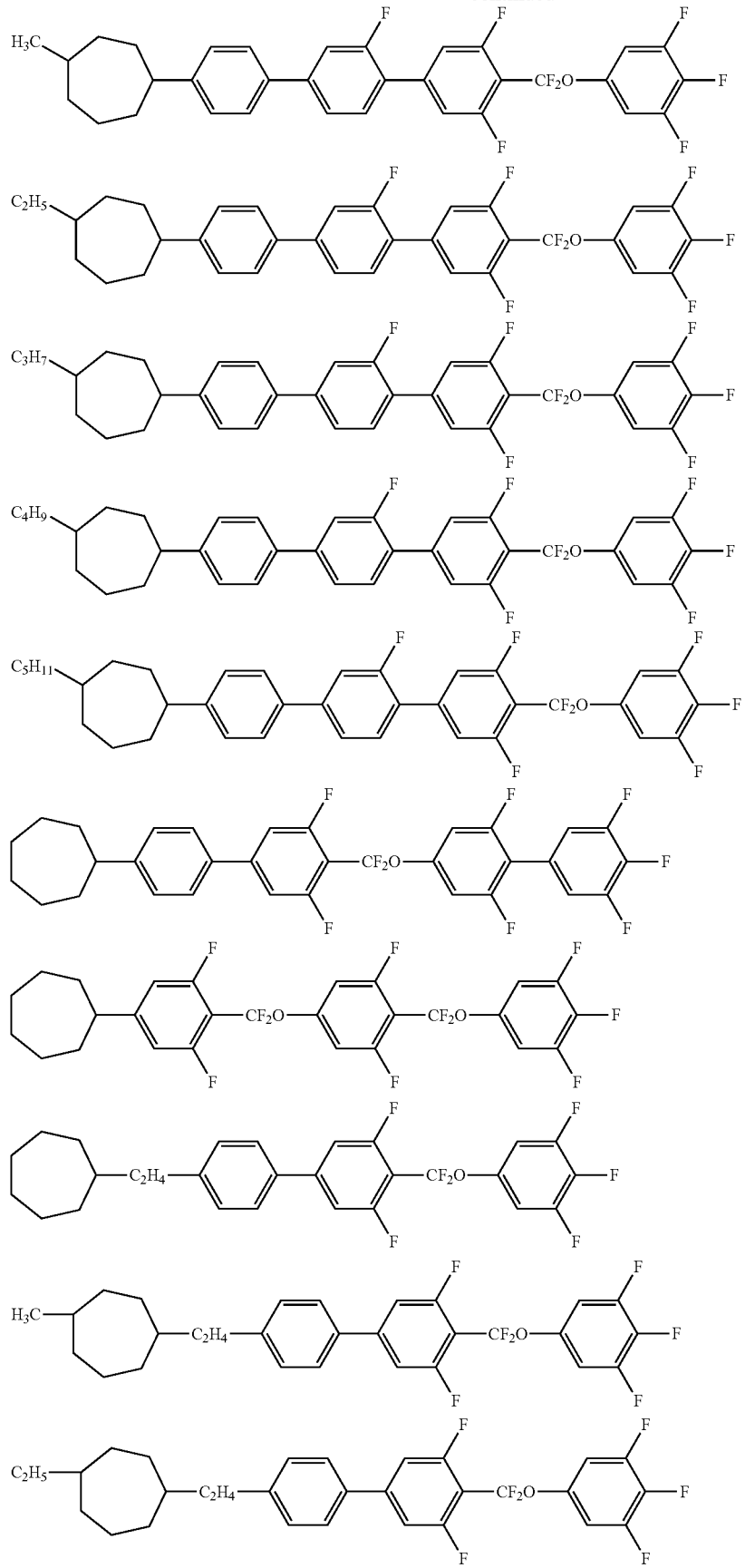

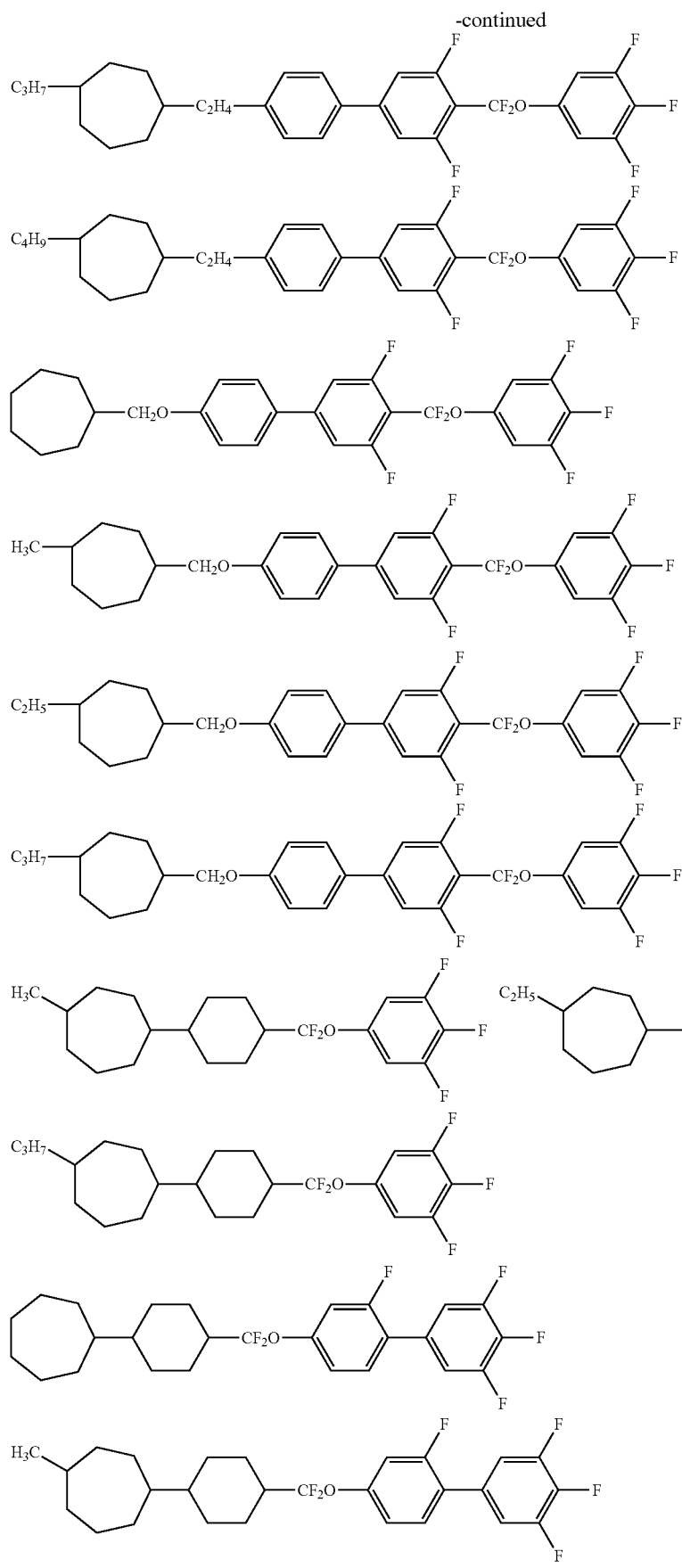

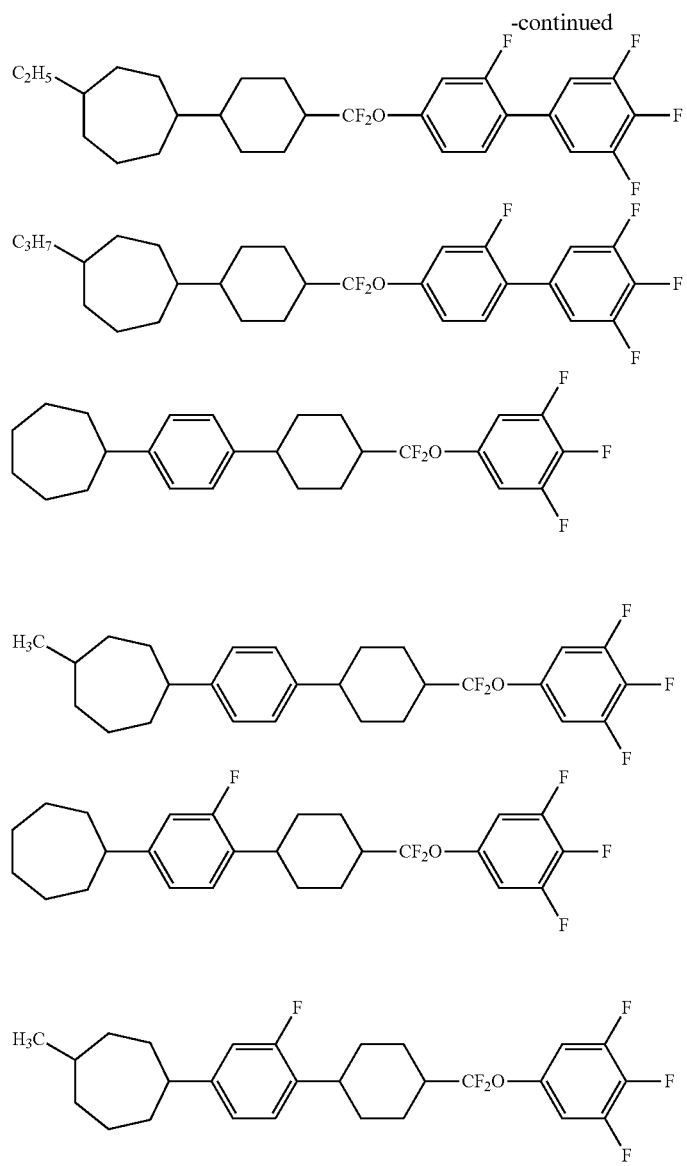
-continued
Example 6
Preparing the Liquid Crystal Mixture a
Mixing each compound according to the following weight percentages to obtain the liquid crystal mixture a:
| | Monomer | Weight Percentages (%) |
|---|---|---|
| Formula II | $C_5H_{11}$— | 18 |
| Formula III | $C_3H_7$— | 10 |

-continued
| | Monomer | Weight Percentages (%) |
|---|---|---|
| Formula III | 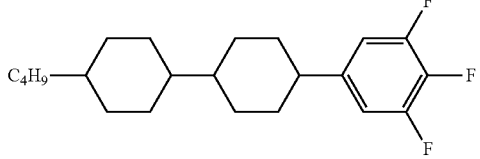 | 7 |
| Formula III | 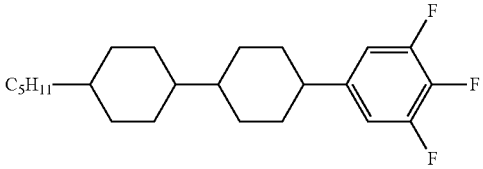 | 5 |
| Formula II | 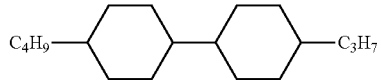 | 9 |
| Formula III | 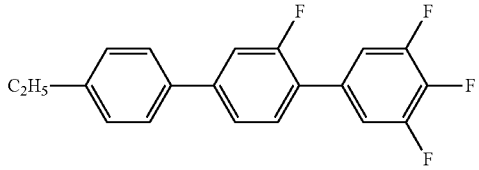 [SMILES: CCc1ccc(-c2ccc(-c3cc(F)c(F)c(F)c3)c(F)c2)cc1] | 7 |
| Formula III | 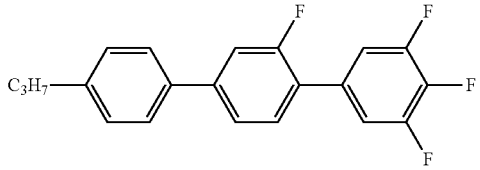 | 8 |
| Formula III | 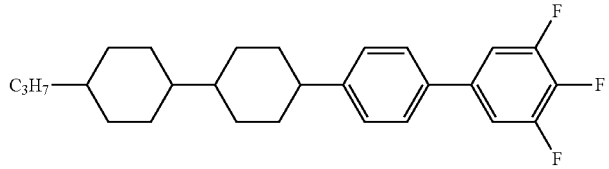 | 4 |
| Formula III | 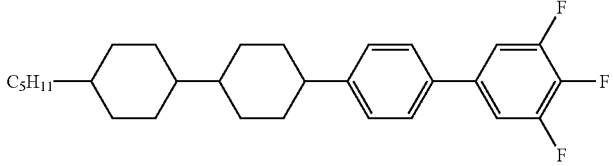 | 4 |
| Formula I-17 | 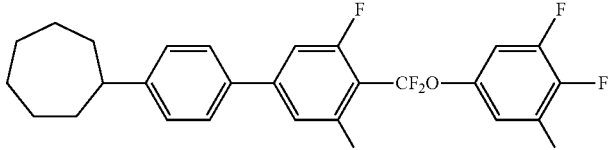 | 10 |
| Formula I-18 | 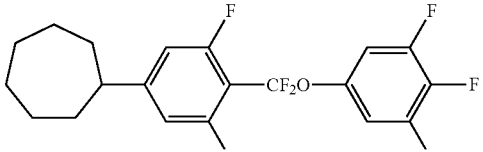 | 4 |

| Monomer | | Weight Percentages (%) |
|---|---|---|
| Formula IV | 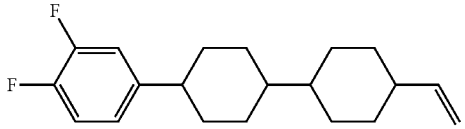 [SMILES: C=CC1CCC(C2CCC(c3ccc(F)c(F)c3)CC2)CC1] | 5 |
| Formula IV | 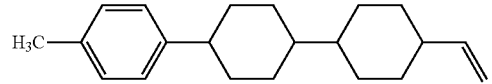 [SMILES: C=CC1CCC(C2CCC(c3ccc(C)cc3)CC2)CC1] | 5 |
| Formula IV | 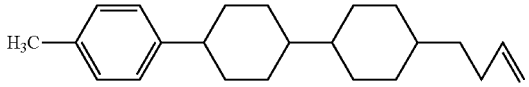 | 4 |

The measurement results of properties of the liquid crystal mixture are shown as follows:
Cp: 87° C.
Δn: 0.105
Δ∈: 7.2V
γ₁: 65;

It can be seen from the above that the composition has a high cleaning point, suitable optical anisotropism, low rotary viscosity and faster responding speed, it can be used in liquid crystal displays.

Comparative Example 1

According to the parts by weight of the components of Example 6 as well as each component, only removing the two components shown in formula I-17 and formula I-18, other components as well as the corresponding parts by weight do not change, the measurement results of the properties of the resulting mixture are shown as follows:
Cp: 80° C.
Δn: 0.115
Δ∈: 5.2V
γ₁: 63;

It can be seen from the above that without the compounds shown in formula I-17 and formula I-18 provided by the present invention, the Δ∈ of the resulting liquid crystal mixture is significantly decreased.

Example 7

Preparing the Liquid Crystal Mixture b

Mixing each compound according to the following weight percentages to obtain liquid crystal mixture b:

| Monomer | | Weight Percentages (%) |
|---|---|---|
| Formula II | 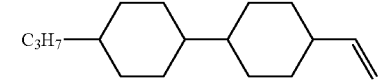 | 24 |
| Formula IV | 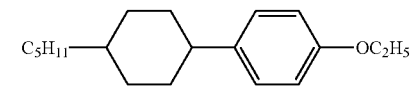 | 10 |
| Formula IV | 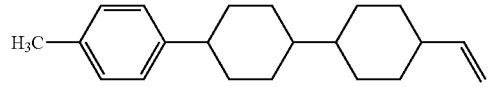 | 12 |
| Formula IV | 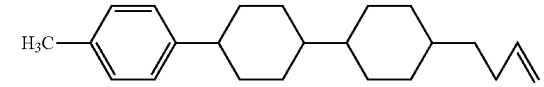 | 8 |
| Formula III | 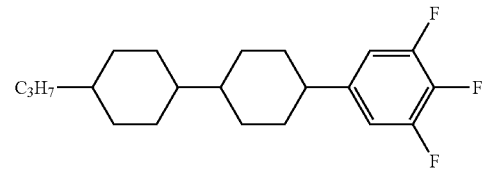 | 8 |

| Monomer | | Weight Percentages (%) |
|---|---|---|
| Formula III | C₅H₁₁–[cyclohexyl]–[cyclohexyl]–[phenyl with 3 F] | 8 |
| Formula IV | C₃H₇–[cyclohexyl]–[phenyl-F]–[phenyl]–[cyclohexyl]–C₃H₇ | 4 |
| Formula IV | C₅H₁₁–[cyclohexyl]–[phenyl-F]–[phenyl]–[cyclohexyl]–C₃H₇ | 4 |
| Formula I-20 | [cycloheptyl]–[phenyl]–[phenyl-F]–[phenyl-F,F]–CF₂O–[phenyl-F,F,F] | 4 |
| Formula I-17 | [cycloheptyl]–[phenyl]–[phenyl-F,F]–CF₂O–[phenyl-F,F,F] | 10 |
| Formula III | C₃H₇–[cyclohexyl]–[cyclohexyl]–[phenyl]–[phenyl-F,F,F] | 4 |
| Formula III | C₃H₇–[cyclohexyl]–[cyclohexyl]–[phenyl]–[phenyl-F,F,F] | 4 |

The measurement results of properties of the liquid crystal mixture are shown as follows:

Cp: 94° C.
Δn: 0.125
Δε: 7.8V
$\gamma_1$: 65;

It can be seen from the above that the composition has a high cleaning point, suitable optical anisotropism, low rotary viscosity and faster responding speed, it can be used in liquid crystal displays.

Example 8

Preparing the Liquid Crystal Mixture c

Mixing each compound according to the following weight percentages to obtain liquid crystal mixture c:

| | Monomer | Weight Percentages (%) |
|---|---|---|
| Formula II | $C_3H_7$—[cyclohexyl]—[cyclohexyl]—CH=CH$_2$ | 20 |
| Formula II | $C_3H_7$—[cyclohexyl]—[cyclohexyl]—CH=CH—CH$_3$ | 10 |
| Formula II | $C_3H_7$—[cyclohexyl]—[cyclohexyl]—$C_4H_9$ | 6 |
| Formula IV | $H_3C$—[phenyl]—[cyclohexyl]—[cyclohexyl]—CH$_2$CH=CH$_2$ | 6 |
| Formula III | $C_3H_7$—[cyclohexyl]—[phenyl]—[phenyl(3,4,5-triF)] | 9 |
| Formula III | $C_2H_5$—[cyclohexyl]—[phenyl]—[phenyl(3,4,5-triF)] | 7 |
| Formula IV | $C_3H_7$—[phenyl]—[phenyl(2-F)]—[phenyl]—CH$_2$CH=CH$_2$ | 5 |
| Formula IV | $C_2H_5$—[phenyl]—[phenyl(2-F)]—[phenyl]—CH$_2$CH=CH$_2$ | 5 |
| Formula IV | [3,4-diF-phenyl]—[cyclohexyl]—[cyclohexyl]—CH=CH$_2$ | 5 |
| Formula I-17 | [cycloheptyl]—[phenyl]—[phenyl(3,5-diF)]—CF$_2$O—[phenyl(3,4,5-triF)] | 4 |

| Monomer | Weight Percentages (%) |
|---|---|
| Formula III 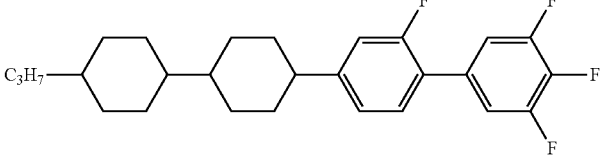 | 4 |
| Formula III 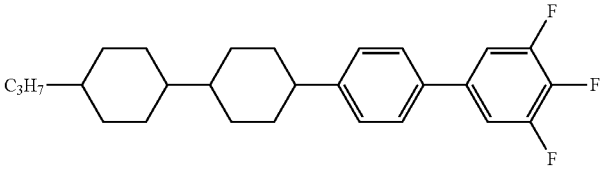 | 4 |
| Formula I-18 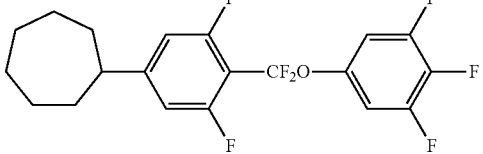 | 7 |
| Formula III 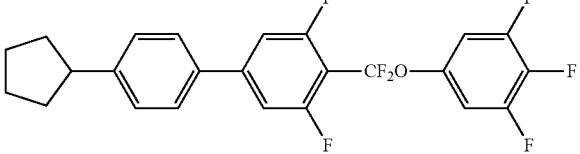 | 8 |

The measurement results of properties of the liquid crystal mixture are shown as follows:

Cp: 95° C.
Δn: 0.105
Δ∈: 7.2V
γ$_1$: 60;

It can be seen from the above that the composition has a high cleaning point, suitable optical anisotropism, low rotary viscosity and faster responding speed, it can be used in liquid crystal displays.

Example 9

Preparing the Liquid Crystal Mixture d

Mixing each compound according to the following weight percentages to obtain liquid crystal mixture d:

| Monomer | Weight Percentages (%) |
|---|---|
| Formula II 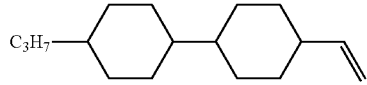 | 22 |
| Formula IV 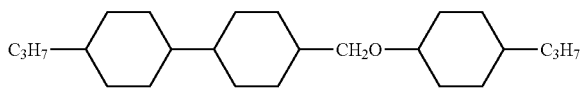 | 2 |
| Formula III 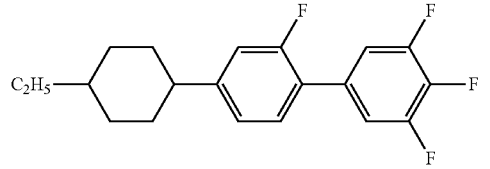 | 5 |

| Monomer | Weight Percentages (%) |
|---|---|
| Formula III 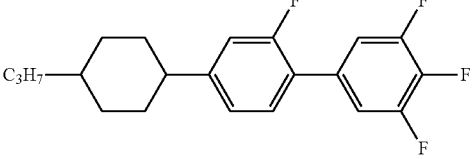 | 12 |
| Formula IV  | 5 |
| Formula IV 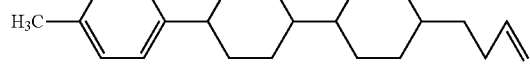 | 4 |
| Formula IV 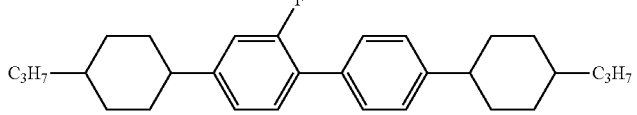 | 4 |
| Formula IV 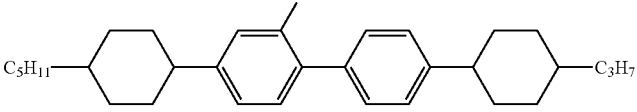 | 4 |
| Formula I-17 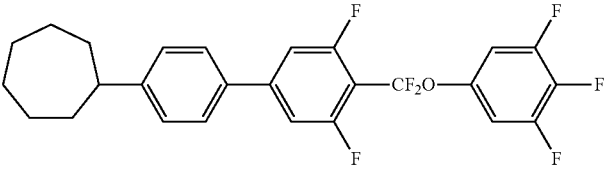 | 4 |
| Formula I 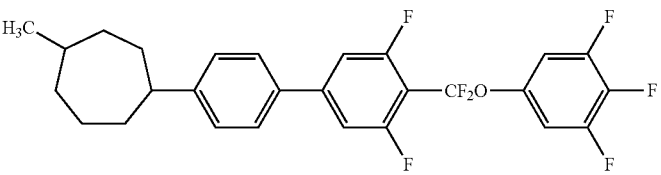 | 8 |
| Formula III 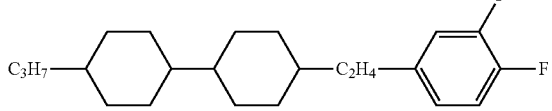 | 10 |
| Formula III 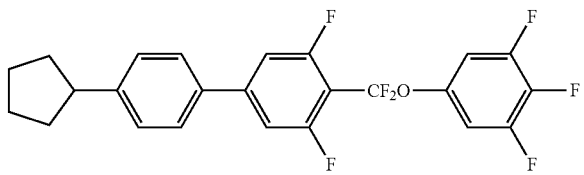 | 7 |
| Formula III 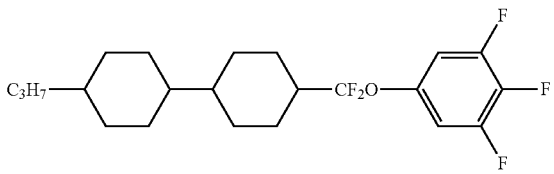 | 7 |

-continued

| Monomer | Weight Percentages (%) |
|---|---|
| Formula III 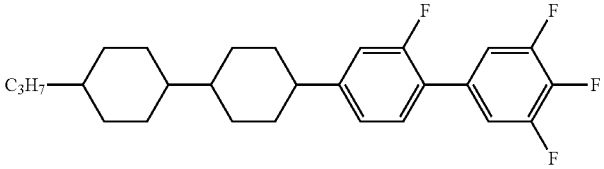 | 6 |

The measurement results of properties of the liquid crystal mixture are shown as follows:
Cp: 91° C.
Δn: 0.098
Δ∈: 6.7V
γ₁: 68;

It can be seen from the above that the composition has a high cleaning point, suitable optical anisotropism, low rotary viscosity and faster responding speed, it can be used in liquid crystal displays.

Example 10

Preparing Liquid Crystal Mixture e

Mixing each compound according to the following weight percentages to obtain liquid crystal mixture e:

| Monomer | Weight Percentages (%) |
|---|---|
| Formula II 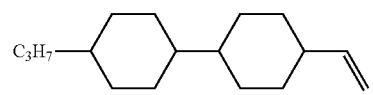 | 20 |
| Formula III 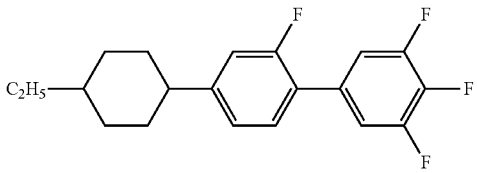 | 5 |
| Formula III 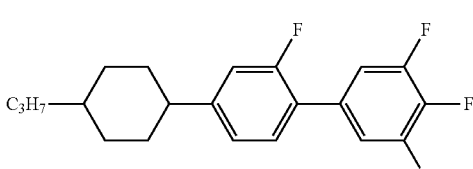 | 5 |
| Formula IV 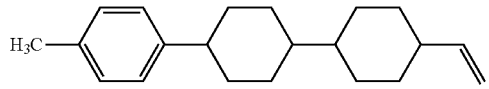 | 8 |
| Formula IV 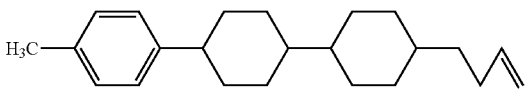 | 5 |
| Formula IV 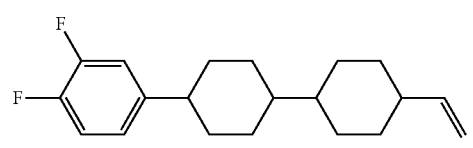 | 7 |
| Formula IV  | 8 |
| Formula IV 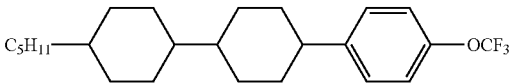 | 5 |

-continued

| Monomer | Weight Percentages (%) |
|---|---|
| Formula III: C₃H₇–[cyclohexyl]–[cyclohexyl]–COO–[phenyl(3,4,5-triF)] | 7 |
| Formula III: C₂H₅–[cyclohexyl]–[cyclohexyl]–COO–[phenyl(3,4,5-triF)] | 6 |
| Formula I-17: [cycloheptyl]–[phenyl]–[phenyl(3,5-diF)]–CF₂O–[phenyl(3,4,5-triF)] | 6 |
| Formula III: C₂H₇–[cyclohexyl]–[cyclohexyl]–[phenyl(2-F)]–[phenyl(3,4,5-triF)] | 7 |
| Formula III: [cyclobutyl]–[phenyl]–[phenyl(3,5-diF)]–CF₂O–[phenyl(3,4,5-triF)] | 8 |
| Formula III: [cyclopentyl]–[phenyl]–[phenyl(3,5-diF)]–CF₂O–[phenyl(3,4,5-triF)] | 3 |

The measurement results of properties of the liquid crystal mixture are shown as follows:

Cp: 86° C.
Δn: 0.10
Δε: 7.1V
$\gamma_1$: 58;

It can be seen from the above that the composition has a high cleaning point, suitable optical anisotropism, a low rotary viscosity and faster responding speed, it can be used in liquid crystal displays.

Example 11
Preparing the Liquid Crystal Mixture f
Mixing each compound according to the following weight percentages to obtain liquid crystal mixture f:
| | Monomer | Weight Percentages (%) |
|---|---|---|
| Formula II | 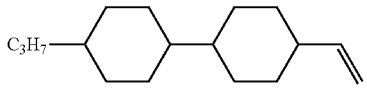 | 12 |
| Formula III | 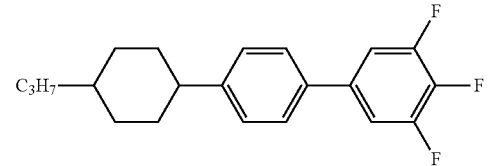 | 6 |
| Formula IV | 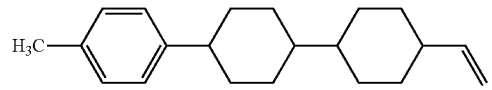 [SMILES: C=CC1CCC(C2CCC(c3ccc(C)cc3)CC2)CC1] | 9 |
| Formula IV | 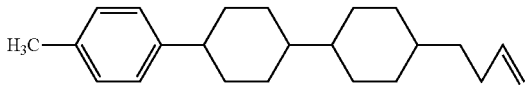 [SMILES: C=CCCC1CCC(C2CCC(c3ccc(C)cc3)CC2)CC1] | 5 |
| Formula IV | 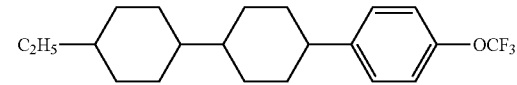 | 7 |
| Formula IV | 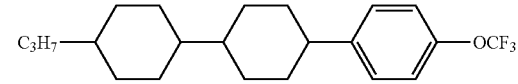 | 8 |
| Formula IV | 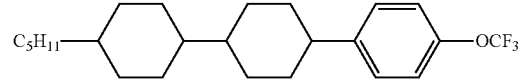 | 5 |
| Formula III | 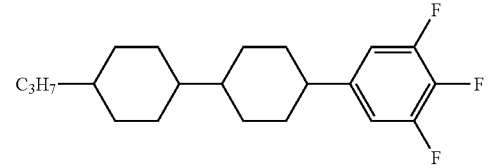 | 7 |
| Formula III | 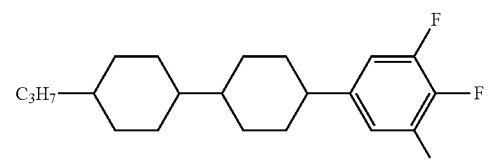 | 6 |
| Formula III | 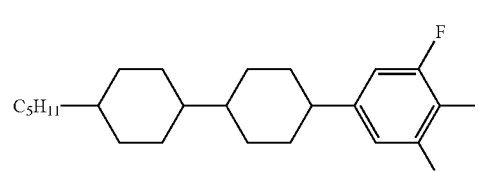 | 6 |

| Monomer | | Weight Percentages (%) |
|---|---|---|
| Formula I-17 | cycloheptyl-phenyl-C6H2F2-CF2O-C6H2F3 | 6 |
| Formula III | C3H7-cyclohexyl-cyclohexyl-C6H3F-C6H2F3 | 7 |
| Formula III | C2H5-phenyl-C6H2F2-CF2O-C6H2F3 | 8 |
| Formula III | C3H7-phenyl-C6H2F2-CF2O-C6H2F3 | 8 |

The measurement results of properties of the liquid crystal mixture are shown as follows:
Cp: 98° C.
Δn: 0.115
Δ∈: 6.8V
γ₁: 58;

It can be seen from the above that the composition has a high cleaning point, suitable optical anisotropism, a low rotary viscosity and faster responding speed, it can be used in liquid crystal displays.

Example 12

Preparing Liquid Crystal Mixture g

Mixing each compound according to the following weight percentages to obtain liquid crystal mixture g:

| Monomer | | Weight Percentages (%) |
|---|---|---|
| Formula II | C3H7-cyclohexyl-cyclohexyl-C4H9 | 12 |
| Formula III | C3H7-cyclohexyl-phenyl-C6H2F3 | 6 |
| Formula III | C3H7-cyclohexyl-CH2CH2-cyclohexyl-C6H2F3 | 9 |

-continued
| Monomer | | Weight Percentages (%) |
|---|---|---|
| Formula IV |  | 5 |
| Formula IV | 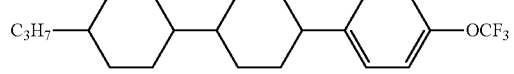 | 4 |
| Formula IV |  | 8 |
| Formula III | 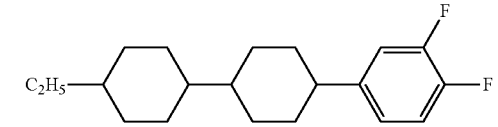 | 8 |
| Formula III | 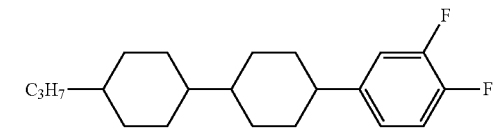 [SMILES: CCC1CCC(C2CCC(c3ccc(F)c(F)c3)CC2)CC1] | 5 |
| Formula III | 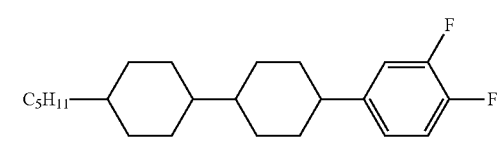 | 3 |
| Formula III | 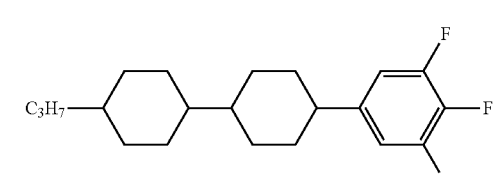 | 6 |
| Formula III | 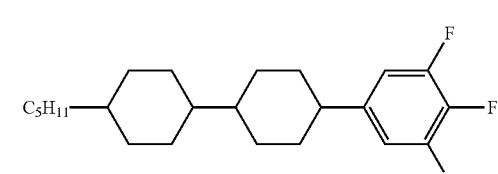 | 6 |
| Formula I-17 | 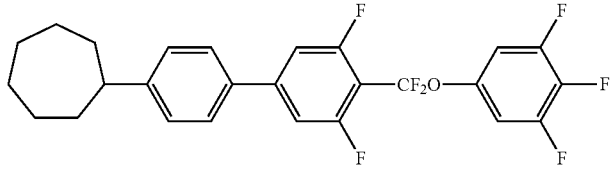 | 6 |
| Formula I-18 | 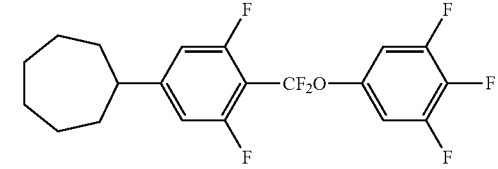 | 4 |
| Formula IV |  | 5 |

| Monomer | | Weight Percentages (%) |
|---|---|---|
| Formula IV |  C$_3$H$_7$—⬡—⬡—⌬—C$_2$H$_5$ | 5 |
| Formula III | 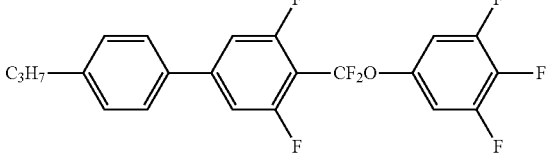 C$_3$H$_7$—⌬—⌬(F,F)—CF$_2$O—⌬(F,F,F) | 5 |
| Formula IV | 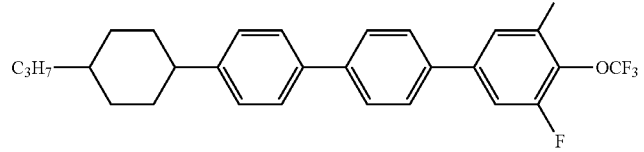 C$_3$H$_7$—⬡—⌬—⌬—⌬(F,F)—OCF$_3$ | 3 |

The measurement results of properties of the liquid crystal mixture are shown as follows:
Cp: 97° C.
Δn: 0.098
Δ∈: 7.2V
γ$_1$: 63;

It can be seen from the above that the composition has a high cleaning point, suitable optical anisotropism, a low rotary viscosity and faster responding speed, it can be used in liquid crystal displays.

Example 13

Preparing the Liquid Crystal Mixture h

Mixing each compound according to the following weight percentages to obtain liquid crystal mixture h:

| Monomer | | Weight Percentages (%) |
|---|---|---|
| Formula II | 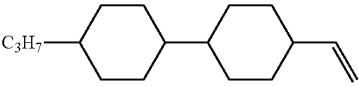 C$_3$H$_7$—⬡—⬡—CH=CH$_2$ | 22 |
| Formula III | 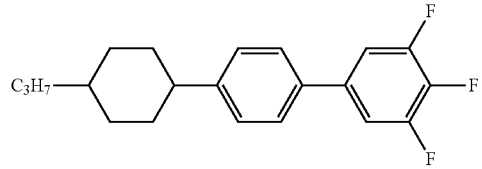 C$_3$H$_7$—⬡—⌬—⌬(F,F,F) | 6 |
| Formula IV | 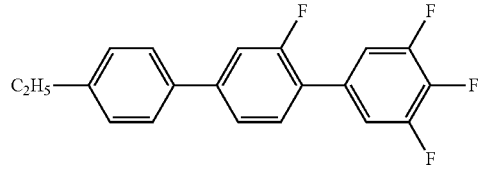 C$_2$H$_5$—⌬—⌬(F)—⌬(F,F,F) | 9 |
| Formula IV | 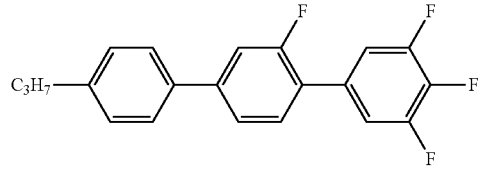 C$_3$H$_7$—⌬—⌬(F)—⌬(F,F,F) | 5 |

-continued

| Monomer | | Weight Percentages (%) |
|---|---|---|
| Formula IV | C₂H₅–⟨phenyl⟩–⟨phenyl(F)⟩–⟨phenyl⟩–C₃H₇ | 4 |
| Formula IV | C₂H₅–⟨phenyl⟩–⟨phenyl(F)⟩–⟨phenyl⟩–C₄H₉ | 4 |
| Formula IV | C₂H₅–⟨phenyl⟩–⟨phenyl(F)⟩–⟨phenyl⟩–C₅H₁₁ | 4 |
| Formula III | C₃H₇–⟨cyclohexyl⟩–⟨cyclohexyl⟩–⟨phenyl(3F)⟩ | 6 |
| Formula III | C₅H₁₁–⟨cyclohexyl⟩–⟨cyclohexyl⟩–⟨phenyl(3F)⟩ | 6 |
| Formula I-17 | ⟨cycloheptyl⟩–⟨phenyl⟩–⟨phenyl(2F)⟩–CF₂O–⟨phenyl(3F)⟩ | 6 |
| Formula I-19 | ⟨cycloheptyl⟩–⟨cyclohexyl⟩–CF₂O–⟨phenyl(3F)⟩ | 4 |
| Formula III | C₃H₇–⟨cyclohexyl⟩–⟨cyclohexyl⟩–CF₂O–⟨phenyl(3F)⟩ | 5 |
| Formula III | C₂H₅–⟨cyclohexyl⟩–⟨cyclohexyl⟩–⟨phenyl⟩–⟨phenyl(3F)⟩ | 5 |

| Monomer | Weight Percentages (%) |
|---|---|
| Formula III ![structure] | 6 |
| Formula III ![structure] | 4 |
| Formula III ![structure] | 4 |

The measurement results of properties of the liquid crystal mixture are shown as follows:
Cp: 90° C.
Δn: 0.120
Δ∈: 7.6V
$\gamma_1$: 60;

It can be seen from the above that the composition has a high cleaning point, suitable optical anisotropism, a low rotary viscosity and faster responding speed, it can be used in liquid crystal displays.

INDUSTRIAL APPLICATION

The liquid crystal compound represented by formula I provided in the present invention has the necessary general physical properties of compounds: stable to light and heat, wider nematic phase, a wider liquid crystal state temperature range, better low temperature miscibility, a better miscibility with other compounds, in particularly the compound has a low rotary viscosity $\gamma_1$ and a high dielectric anisotropy (Δ∈>0). The synthesis of such compounds is of great importance for developing monomer liquid crystal compounds having a low rotary viscosity $\gamma_1$ and high dielectric anisotropy Δ∈. The liquid crystal mixtures comprising formula I have the wider temperature range of liquid crystalline phase, lower viscosity, suitable refractivity anisotropism as well as low starting voltage, can improve the liquid crystal composites and display properties, can achieve a lower threshold voltage and low rotary viscosity $\gamma_1$ when the optical elements are used, which are of great importance to achieve a quick display response.

The invention claimed is:
1. A compound represented by formula I,

Formula I in the formula I, both $R_1$ and $R_2$ are represented as groups shown in the following A, B or C:

A. at least one of group selected from H, —Cl, —F, —CN, —OCN, —OCF$_3$, —CF$_3$, —CHF$_2$, —CH$_2$F, —OCHF$_2$, —SCN, —NCS, —SF$_5$, C1-C15 alkyl, C1-C15 alkoxy, C2-C15 alkenyl and C2-C15 alkenoxy;

B. groups obtained by substituting one or at least two non-adjacent —CH$_2$— in A groups with at least one of following groups and to which oxygen atoms are not directly attached: —CH═CH—, —C≡C—, —COO—, —OOC—, cyclobutyl, —O— or —S—;

C. at least one of groups obtained by substituting at least one of hydrogen in A groups and B groups with fluorine or chlorine;

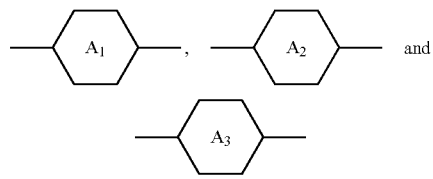

are at least one of a single bond or following groups:

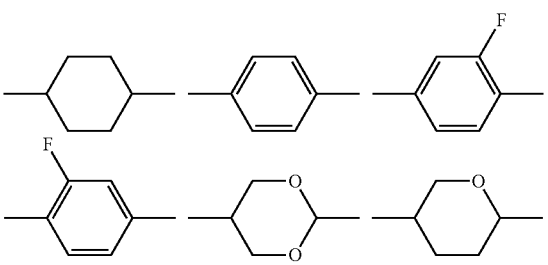

-continued

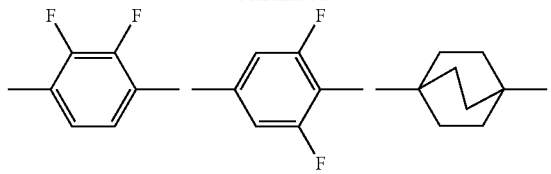

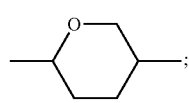

$Z_1$ and $Z_2$ are same or different, both of them are selected from at least one of a single bond, —$CH_2$—, —$CH_2CH_2$—, —$(CH_2)_3$—, —$(CH_2)_4$—, —$CH=CH$—, —$C\equiv C$—, —COO—, —OOC—, —$CF_2O$—, —$OCH_2$—, —$CH_2O$—, —$OCF_2$—, —$CF_2CH_2$—, —$CH_2CF_2$—, —$C_2F_4$— and —$CF=CF$—;

a, b and c are an integer from 0 to 3, and a+b+c≤5;

when a, b and c represents 2 or 3 respectively, the groups represented by

may be same or different, the groups represented by

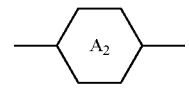

may be same or different, and the groups represented by

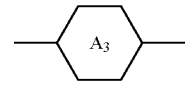

may be same or different.

2. The compound according to claim 1, characterized in that the compound represented by the formula I is any one of the compounds represented by the following formulas I-1 to I-6:

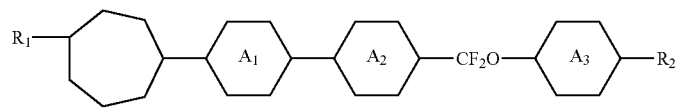
Formula I-1

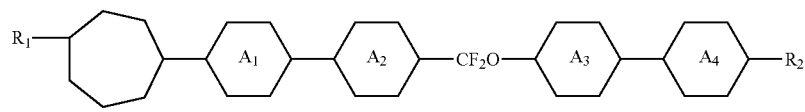
Formula I-2

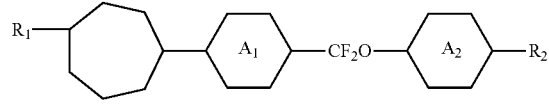
Formula I-3

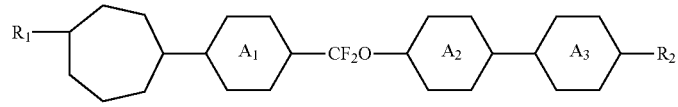
Formula I-4

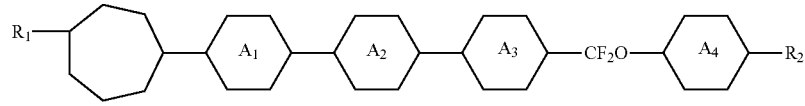
Formula I-5

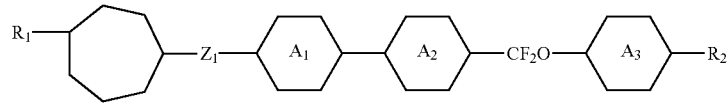
Formula I-6 wherein the definition of

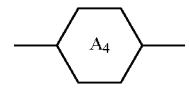

is same as that of

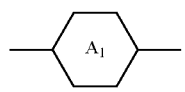

3. A liquid crystal mixture comprising the compound represented by the formula I of claim 2.

4. A liquid crystal mixture comprising any one of the compound represented by formula I and the compound represented by formulas II to IV of claim 2; or,
the liquid crystal mixture consisting of any one of the compound represented by formula I and the compound represented by formula II to formula IV of claim 2:

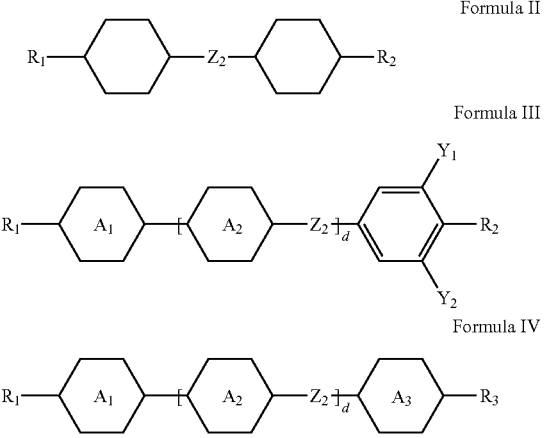

Formula II

Formula III

Formula IV in the formula II to formula IV, $R_1$ and $R_2$ are same or different, both of selected from any one of hydrogen, halogen, —CN, C1-C7 alkyl, C1-C7 alkoxy, C2-C7 alkenyl, C1-C5 fluoroalkoxy, cyclobutyl and cyclopentyl;

$Z_2$ are selected from any one of single bond, —CH$_2$—CH$_2$—, —CH=CH—, —C≡C—, —COO—, —OOC—, —OCH$_2$—, —CH$_2$O—, —CF$_2$O— and —OCF$_2$—;

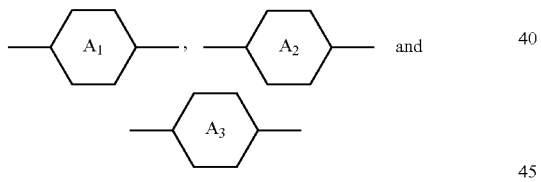

and are selected from at least one of a single bond and the following groups:

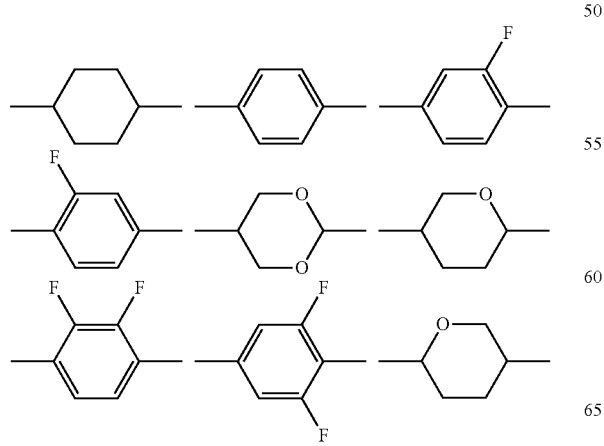

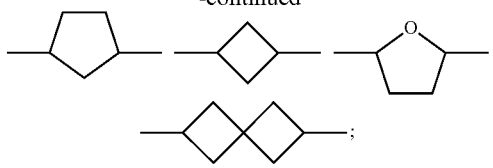

$Y_1$ and $Y_2$ are selected from any one of H and F;

d is an integer from 0 to 2.

5. The liquid crystal mixture according to claim 4, characterized in that the mass ratio of any of the compound represented by formula I, the compound represented by formula II, formula III and formula IV of claim 3 is 0-30: 4-50: 5-50: 3-45; and the weight of the compound represented by formula I is not 0.

6. The liquid crystal mixture according to claim 5, characterized in that the liquid crystal mixture is any one of the liquid crystal mixtures a-h:

the liquid crystal mixture a comprises or consists of the following components in the respective parts by weight thereof:

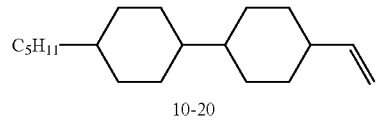

10-20

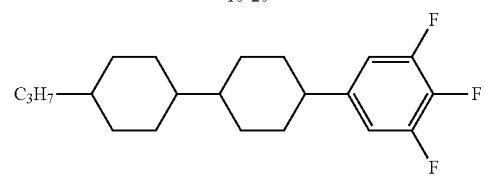

5-15

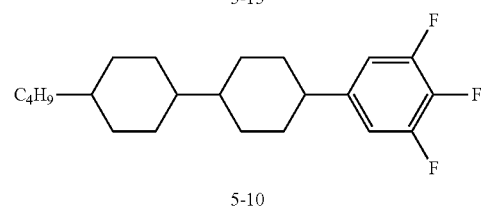

5-10

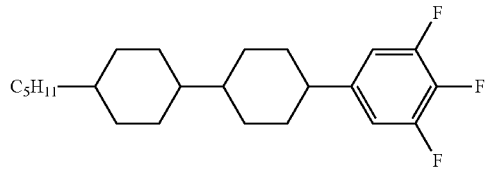

3-8

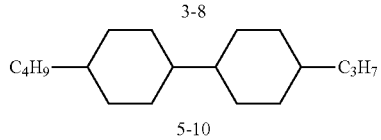

5-10

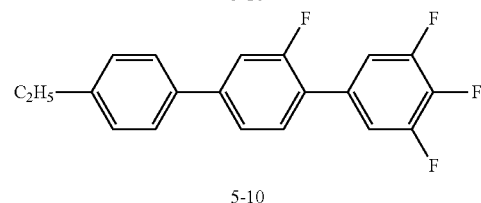

5-10

101
-continued
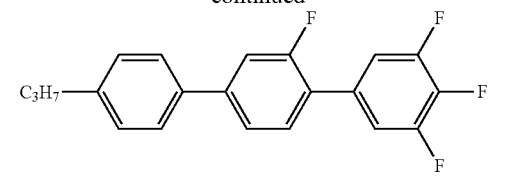
5-10
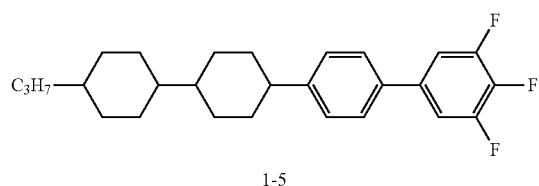
1-5
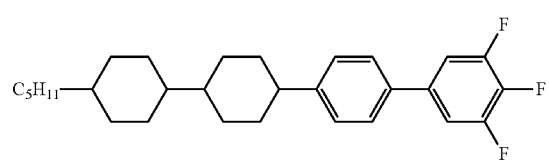
1-5
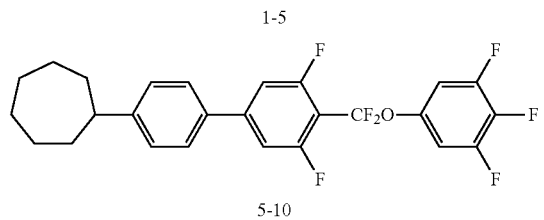
5-10
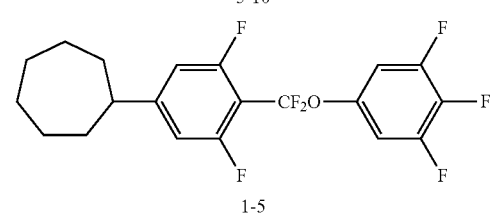
1-5
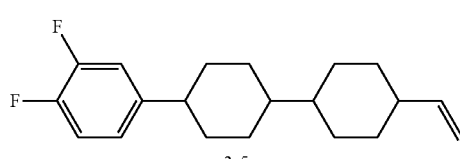
3-5
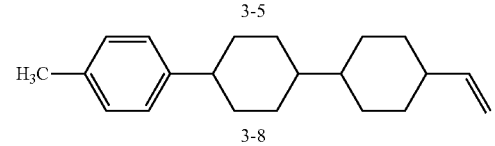
3-8
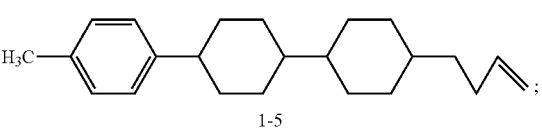
1-5
the liquid crystal mixture b comprises or consists of the following components in the respective parts by weight thereof:
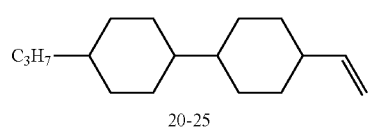
20-25
102
-continued
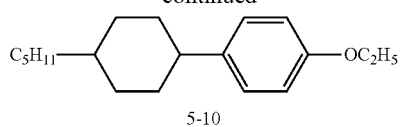
5-10
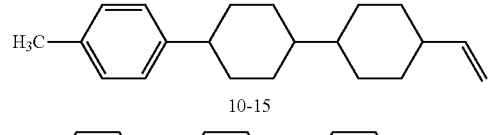
10-15
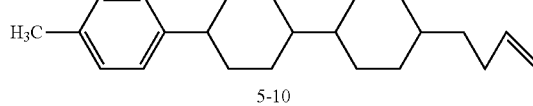
5-10
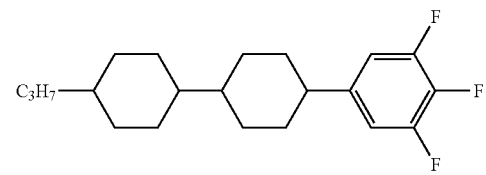
5-10
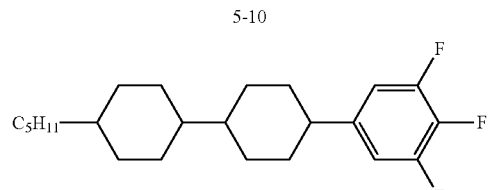
5-10
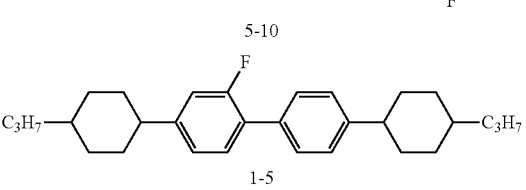
1-5
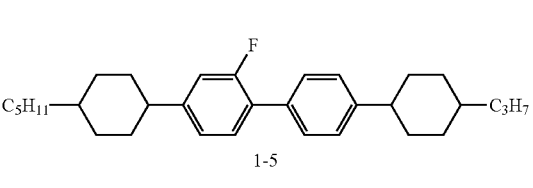
1-5
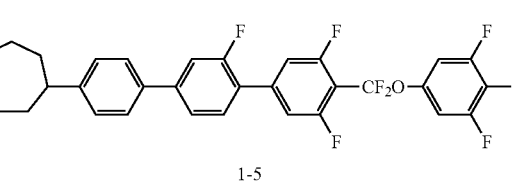
1-5
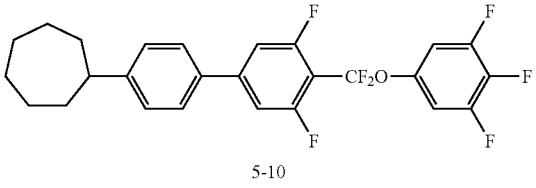
5-10
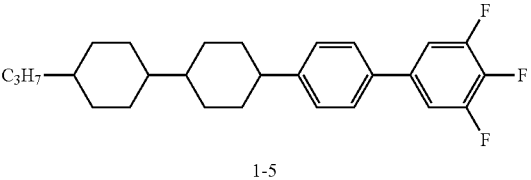
1-5

-continued
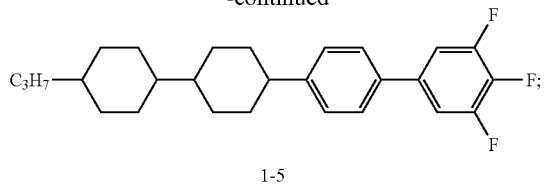
1-5
the liquid crystal mixture c comprises or consists of the following components in the respective parts by weight thereof:
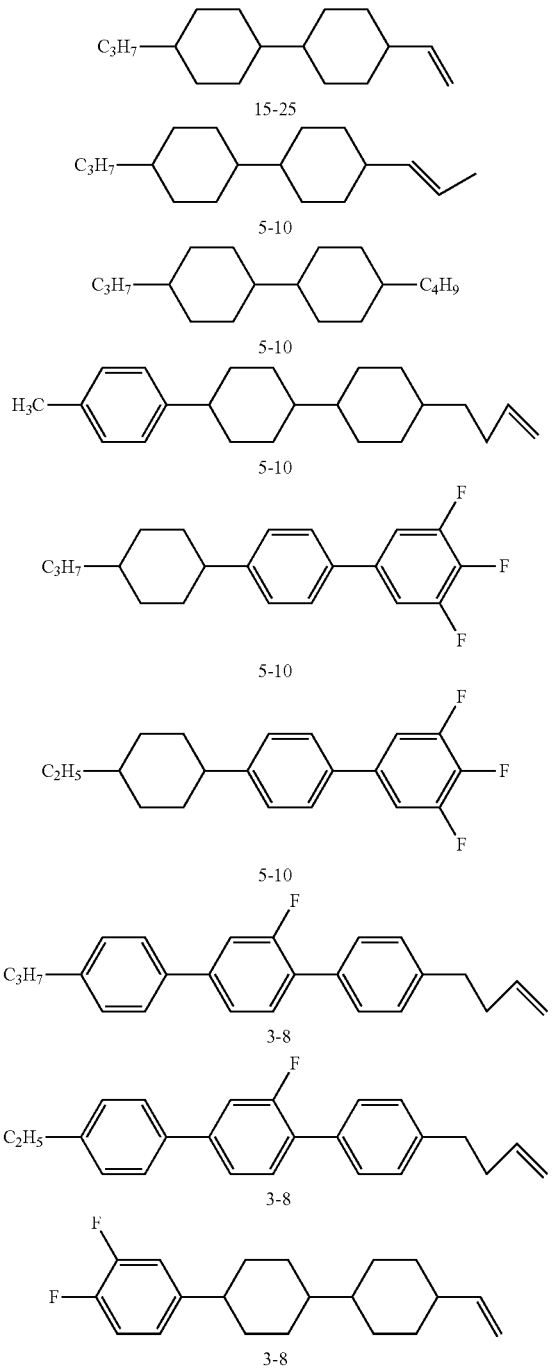
-continued
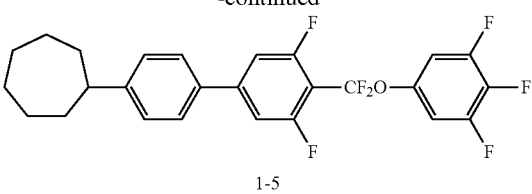
1-5
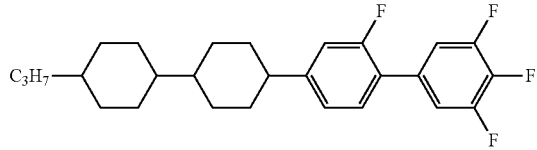
1-5
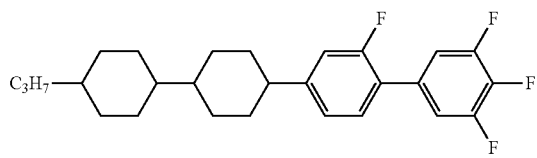
1-5
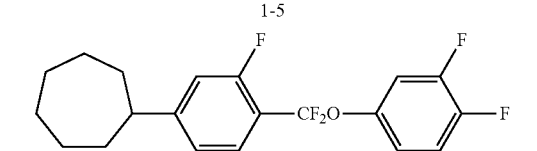
5-10
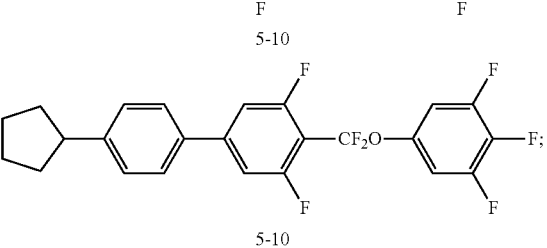
5-10
the liquid crystal mixture d specifically comprises or consists of the following components in the respective parts by weight thereof:
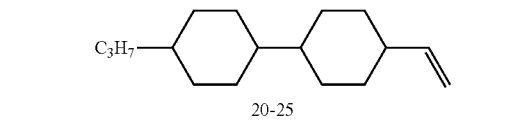
20-25
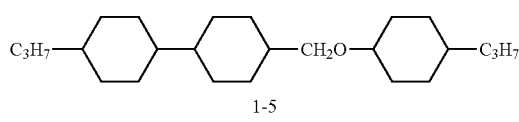
1-5
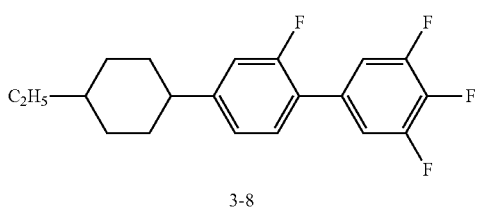
3-8

-continued
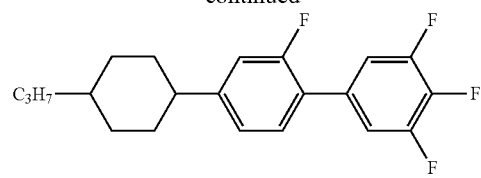
10-15
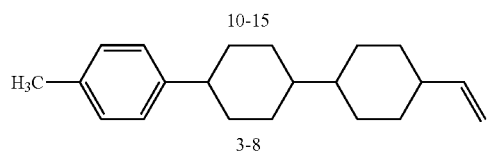
3-8
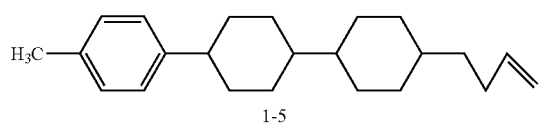
1-5
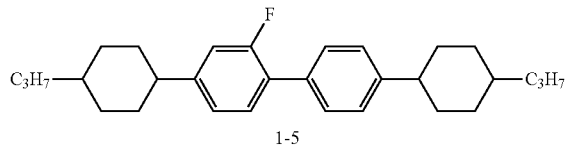
1-5
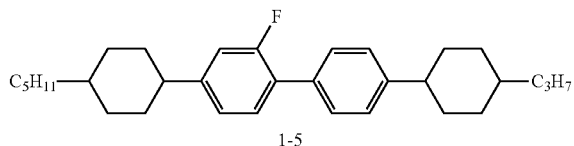
1-5
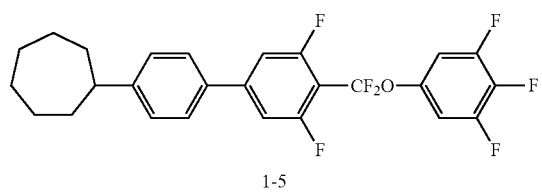
5-10
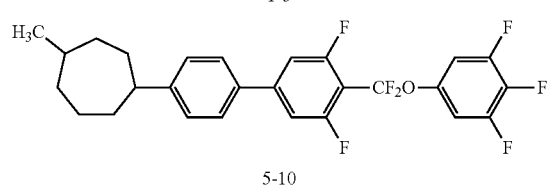
5-10
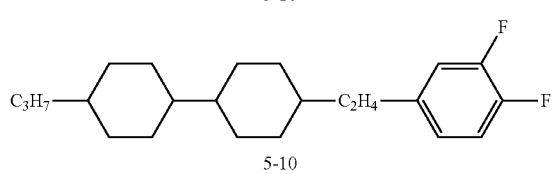
5-10
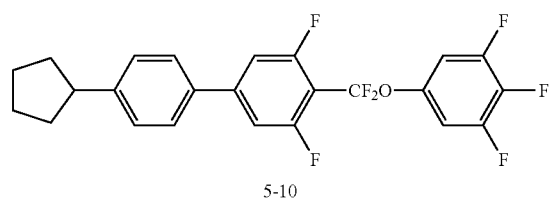
5-10
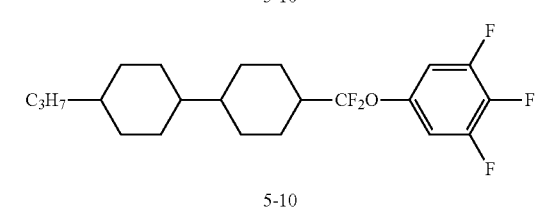
5-10
-continued
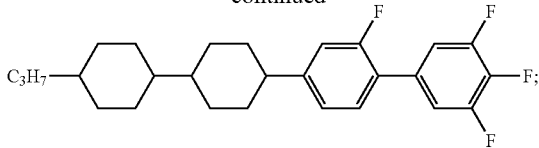
5-10
the liquid crystal mixture e comprises or consists of the following components in the respective parts by weight thereof:
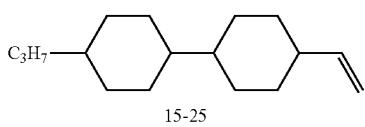
15-25
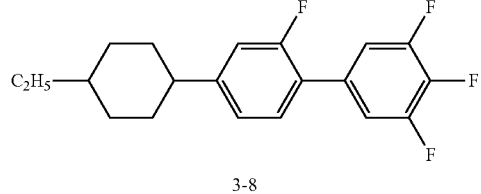
3-8
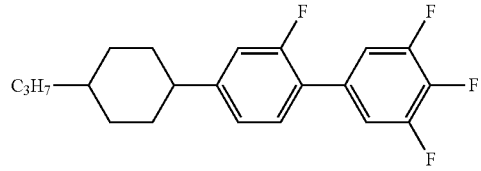
3-8
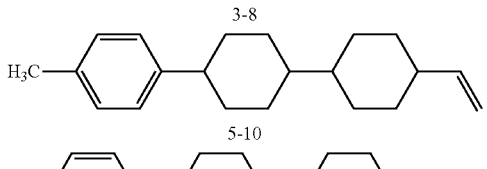
5-10
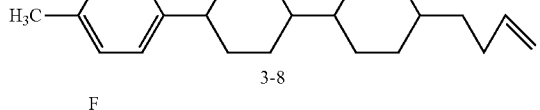
3-8
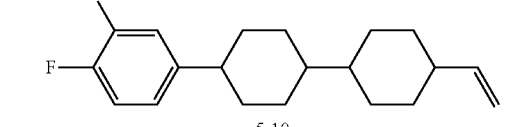
5-10
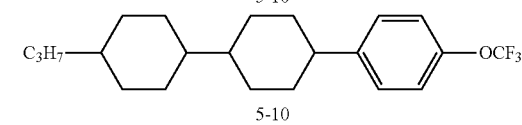
5-10
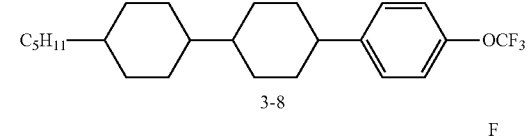
3-8
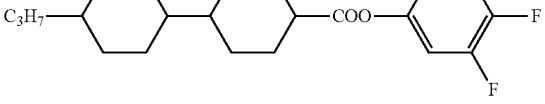
5-10

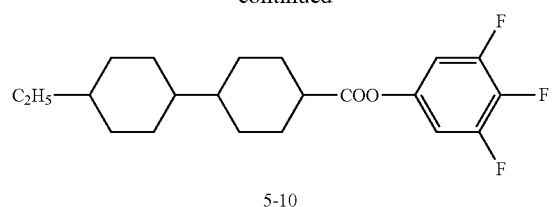
5-10
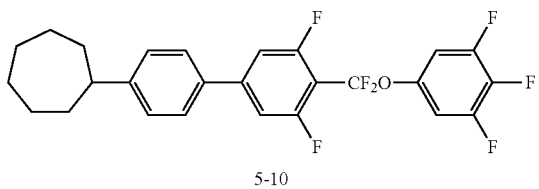
5-10
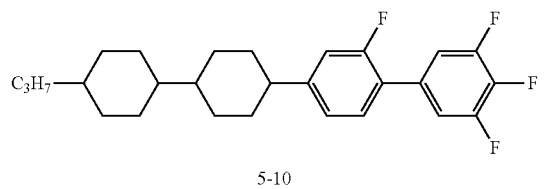
5-10
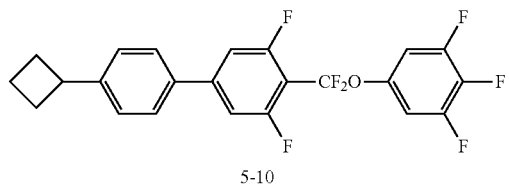
5-10
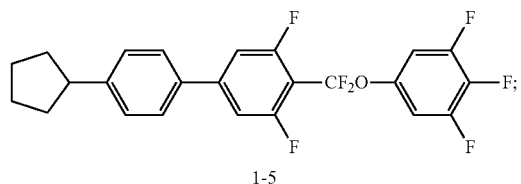
1-5
the liquid crystal mixture f specifically comprises or consists of the following components in the respective parts by weight thereof:
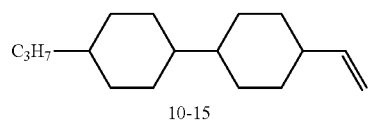
10-15
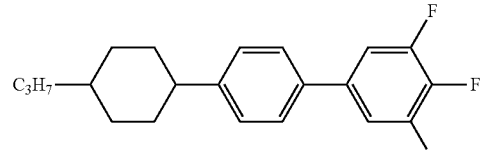
5-10
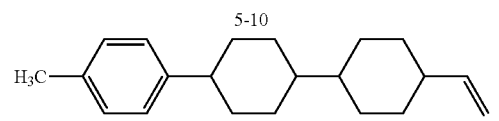
5-10
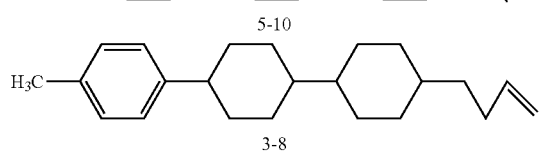
3-8
5-10
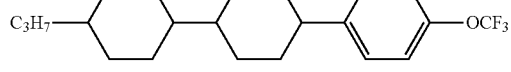
5-10
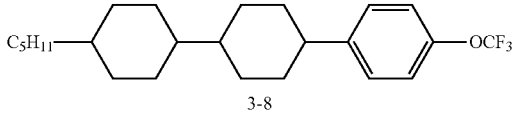
3-8
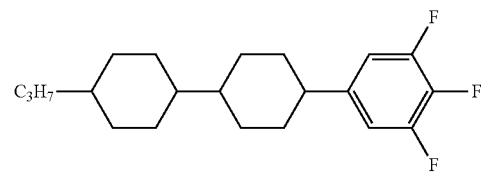
5-10
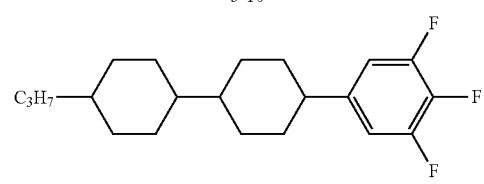
5-10
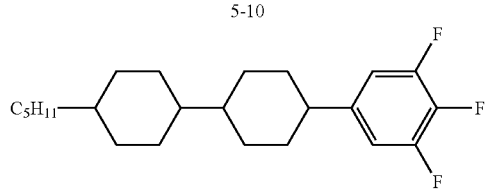
5-10
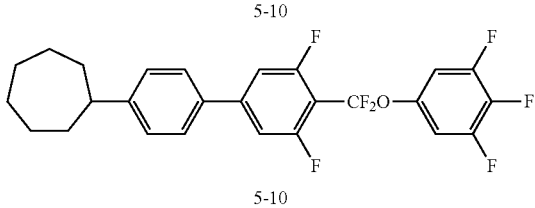
5-10
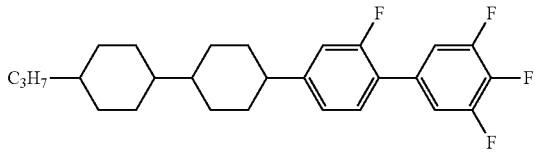
5-10
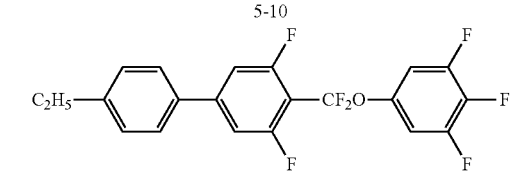
5-10
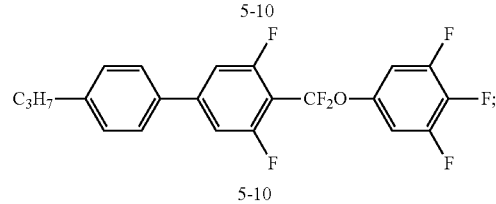
5-10 the liquid crystal mixture g comprises or consists of the following components in the respective parts by weight thereof:
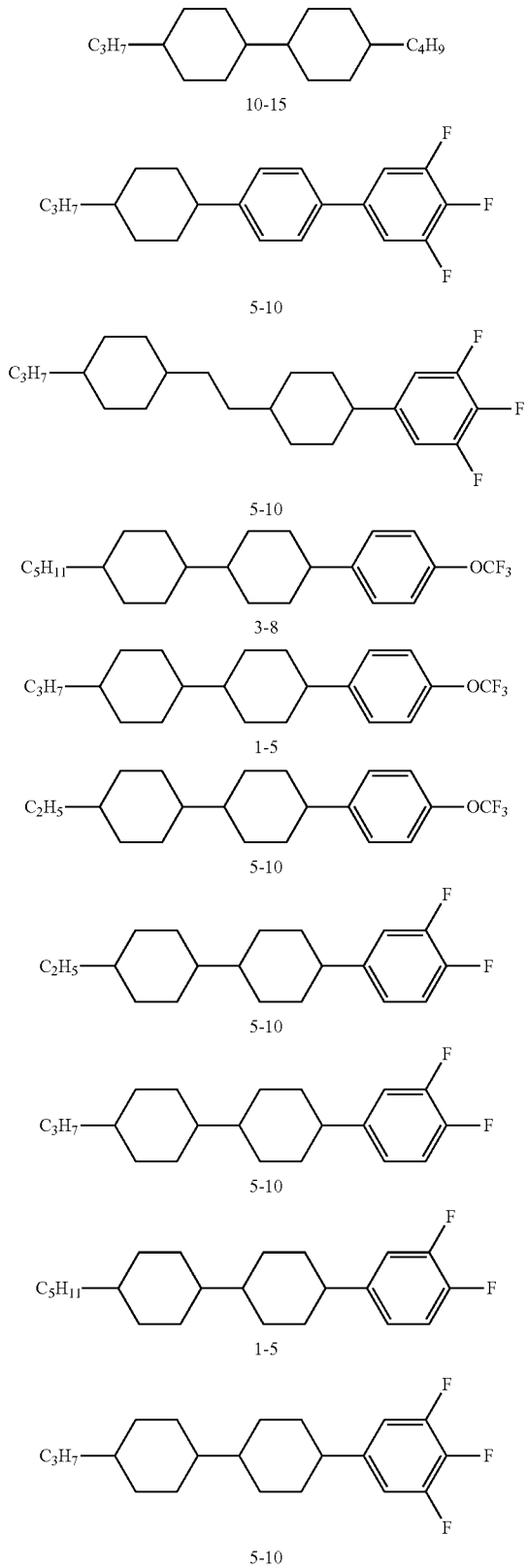
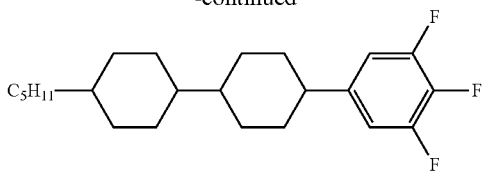
5-10
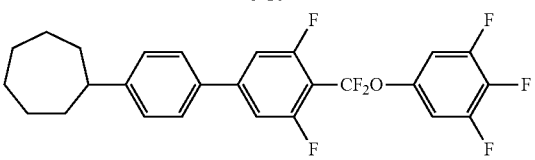
5-10
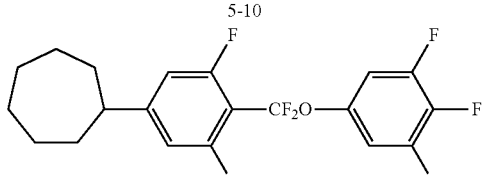
1-5
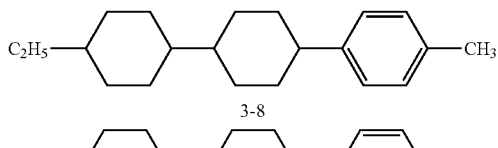
3-8
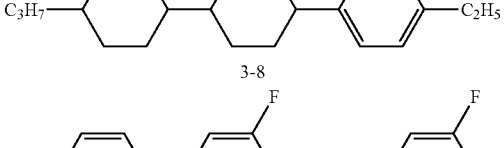
3-8
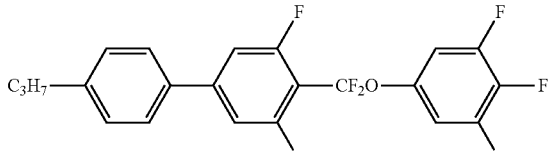
5-10
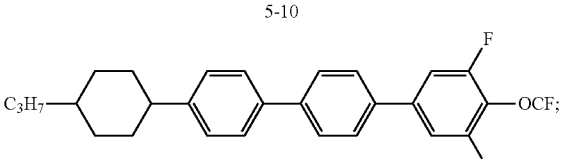
1-5
the liquid crystal mixture h specifically comprises or consists of the following components in the respective parts by weight thereof:
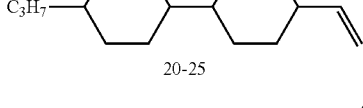
20-25
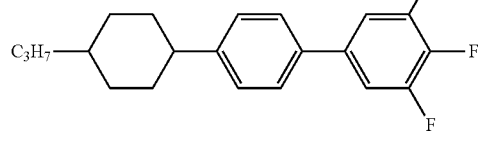
5-10

-continued
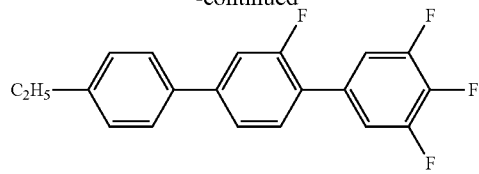
5-10
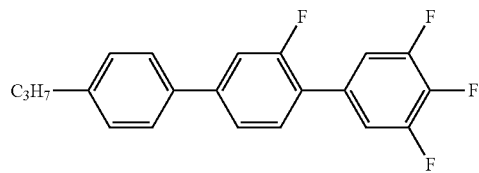
3-8
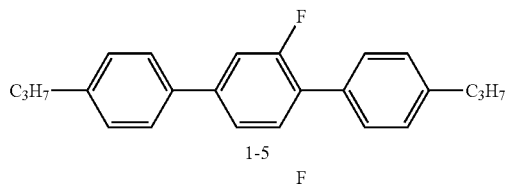
1-5
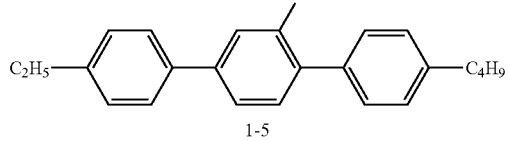
1-5
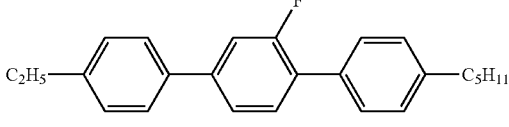
1-5
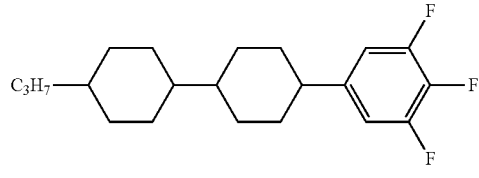
5-10
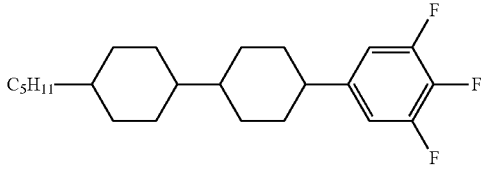
5-10
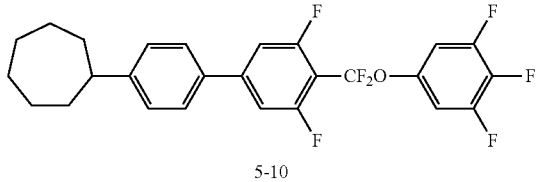
5-10
-continued
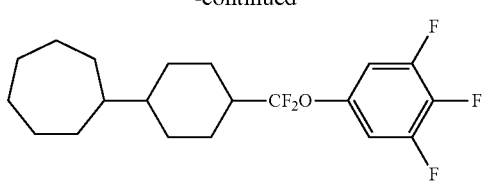
1-5
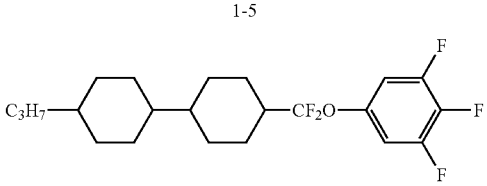
5-10
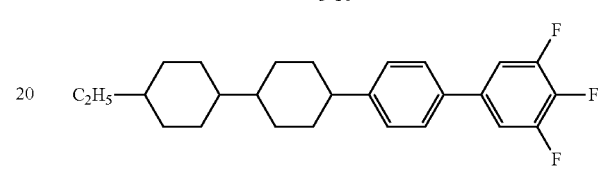
5-10
5-10
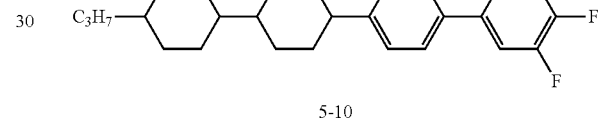
5-10
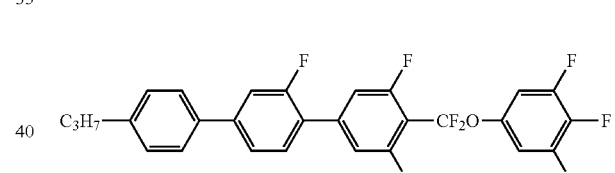
1-5
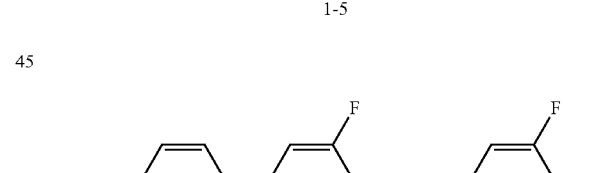
1-5
7. A method of using any one of the liquid crystal compound represented by formula I,
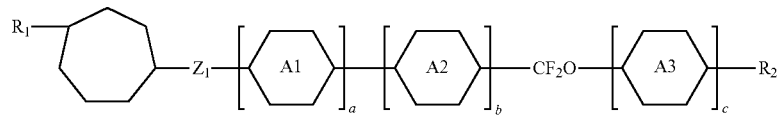
Formula I in the formula I, both $R_1$ and $R_2$ are represented as groups shown in the following A, B or C:

A. at least one of group selected from H, —Cl, —F, —CN, —OCN, —OCF$_3$, —CF$_3$, —CHF$_2$, —CH$_2$F, —OCHF$_2$, —SCN, —NCS, —SF$_5$, C1-C15 alkyl, C1-C15 alkoxy, C2-C15 alkenyl and C2-C15 alkenoxy;

B. groups obtained by substituting one or at least two non-adjacent —CH$_2$— in A groups with at least one of following groups and to which oxygen atoms are not directly attached: —CH=CH—, —C≡C—, —COO—, —OOC—, cyclobutyl, —O— or —S—;

C. at least one of groups obtained by substituting at least one of hydrogen in A groups and B groups with fluorine or chlorine;

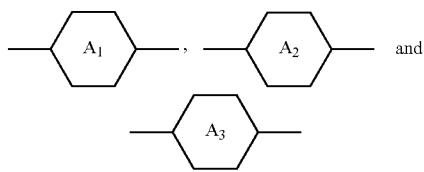

are at least one of a single bond or following groups:

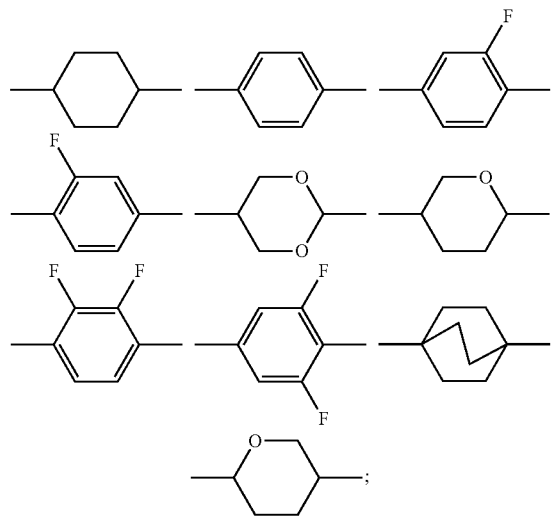

$Z_1$ and $Z_2$ are same or different, both of them are selected from at least one of a single bond, —CH$_2$—, —CH$_2$—CH$_2$—, —(CH$_2$)$_3$—, —(CH$_2$)$_4$—, —CH=CH—, —C≡C—, —COO—, —OOC—, —CF$_2$O—, —OCH$_2$—, —CH$_2$O—, —OCF$_2$—, —CF$_2$CH$_2$—, —CH$_2$CF$_2$—, —C$_2$F$_4$— and —CF=CF—;

a, b and c are an integer from 0 to 3, and a+b+c≤5;

when a, b and c represents 2 or 3 respectively, the groups represented by

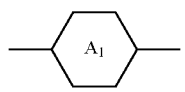

may be same or different, the groups represented by

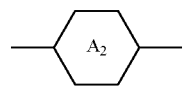

may be same or different, and the groups represented by

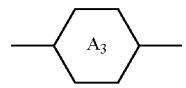

may be same or different and any one of the liquid crystal composition of a liquid crystal mixture comprising the compound represented by formula I in the manufacture of a liquid crystal display material or an electro-optical display material.

8. The method according to claim 7, wherein the liquid crystal display material or electro-optical display material is a display, in particularly a TN type display, VA type display, IPS type display or PDLC type display.

9. The liquid crystal mixture according to claim 5, characterized in that the liquid crystal mixture is any one of the liquid crystal mixtures a-h:

the liquid crystal mixture a comprises or consists of the following components in the respective parts by weight thereof:

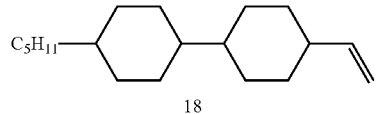

18

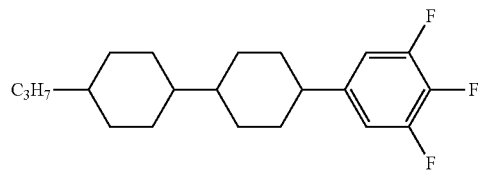

10

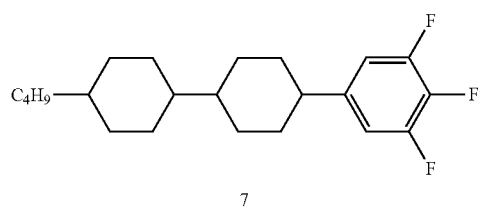

7

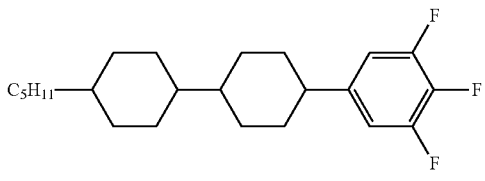

5

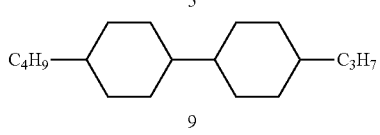

9

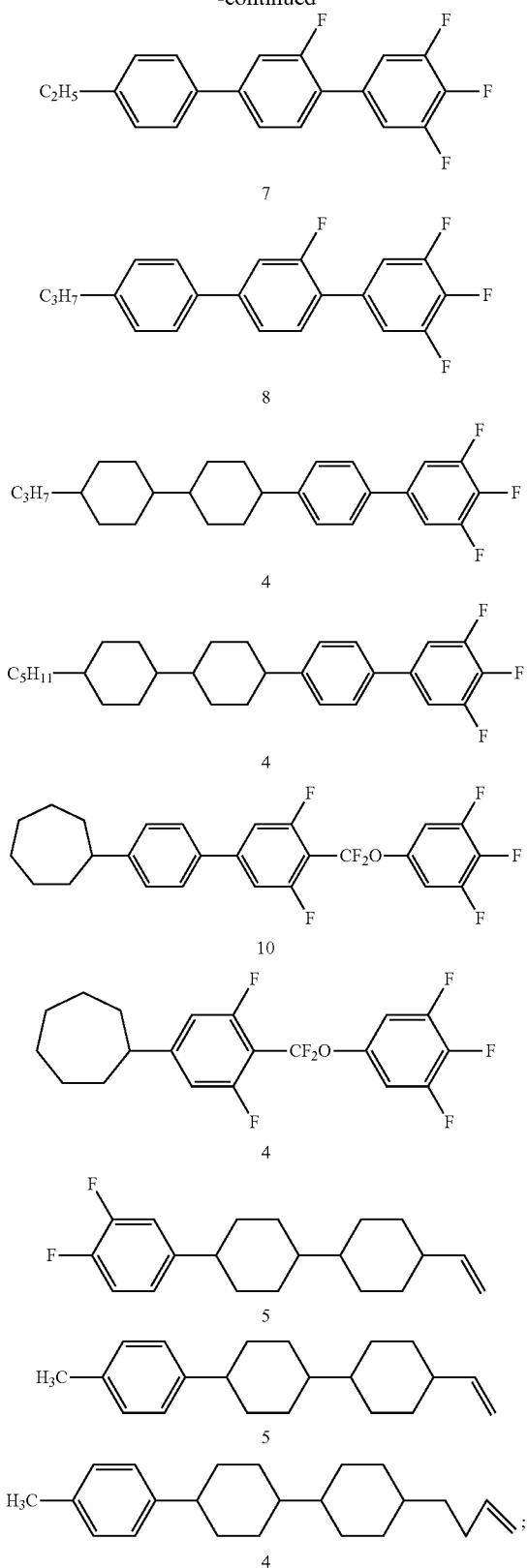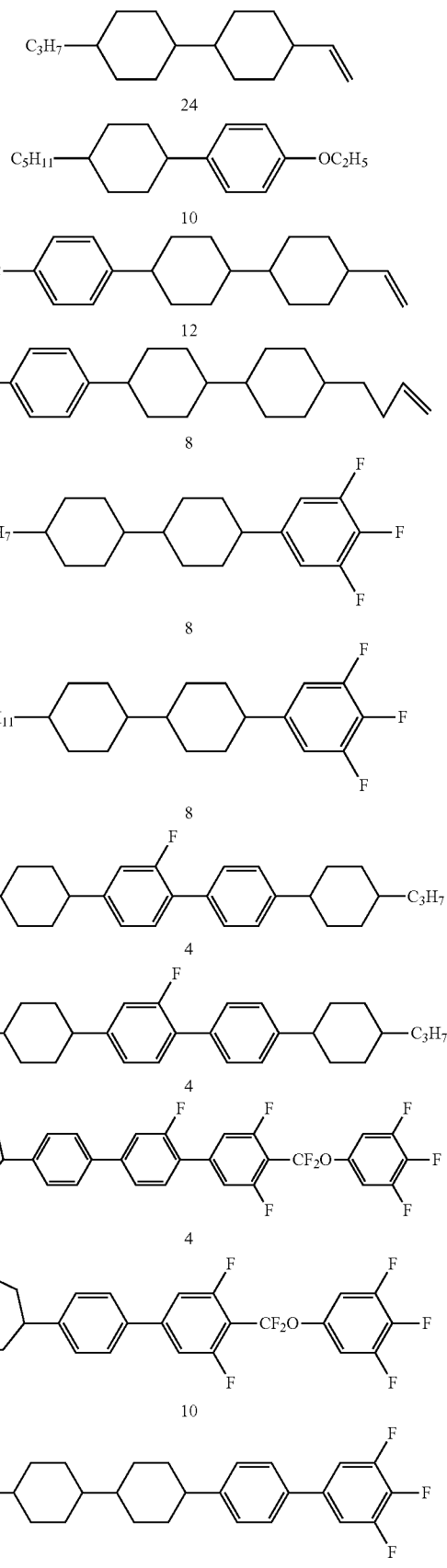
the liquid crystal mixture b comprises or consists of the following components in the respective parts by weight thereof:

the liquid crystal mixture c comprises or consists of the following components in the respective parts by weight thereof:

- C₃H₇-Cy-Cy-CH=CH₂ : 20
- C₃H₇-Cy-Cy-CH=CH-CH₃ : 10
- C₃H₇-Cy-Cy-C₄H₉ : 6
- H₃C-Ph-Cy-Cy-CH₂-CH=CH₂ : 6
- C₃H₇-Cy-Ph-Ph(3,4,5-F₃) : 9
- C₂H₅-Cy-Ph-Ph(3,4,5-F₃) : 7
- C₃H₇-Ph-Ph(3-F)-Ph-CH₂-CH=CH₂ : 5
- C₂H₅-Ph-Ph(3-F)-Ph-CH₂-CH=CH₂ : 5
- (2,3-F₂)Ph-Cy-Cy-CH=CH₂ : 5
- C₃H₇-Cy-Cy-Ph-Ph(3,4,5-F₃) : 4 the liquid crystal mixture d comprises or consists of the following components in the respective parts by weight thereof:

- cycloheptyl-Ph-Ph(3,5-F₂)-CF₂O-Ph(3,4,5-F₃) : 4
- C₃H₇-Cy-Cy-Ph(2-F)-Ph(3,4,5-F₃) : 4
- C₃H₇-Cy-Cy-Ph-Ph(3,4,5-F₃) : 4
- cycloheptyl-Ph(3,5-F₂)-CF₂O-Ph(3,4,5-F₃) : 7
- cyclopentyl-Ph-Ph(3,5-F₂)-CF₂O-Ph(3,4,5-F₃) : 8

- C₃H₇-Cy-Cy-CH=CH₂ : 22
- C₃H₇-Cy-Cy-CH₂O-Cy-C₃H₇ : 2
- C₂H₅-Cy-Ph(2-F)-Ph(3,4,5-F₃) : 5

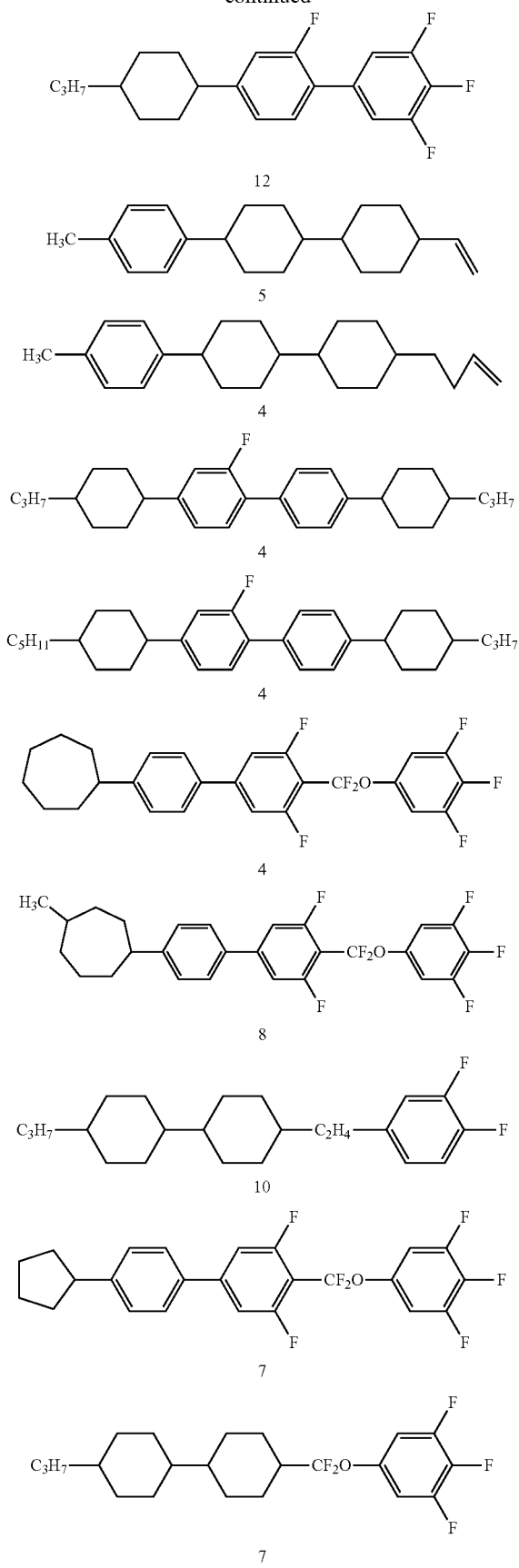
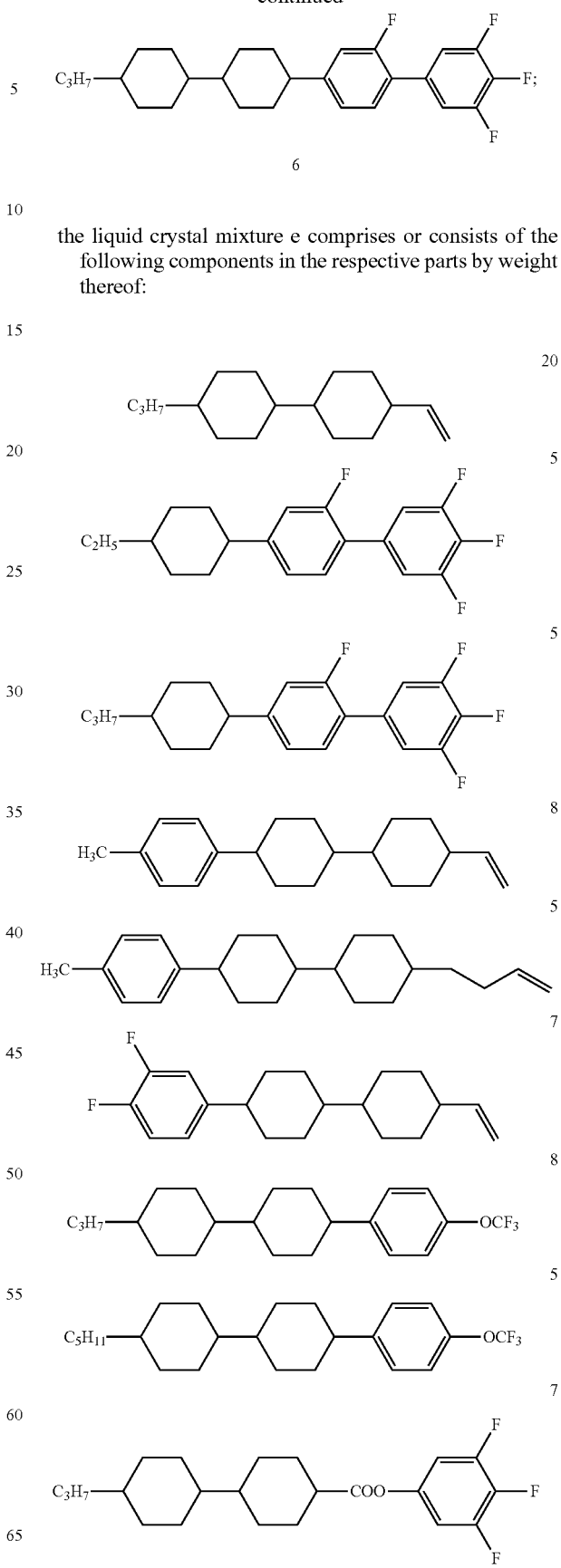
the liquid crystal mixture e comprises or consists of the following components in the respective parts by weight thereof:

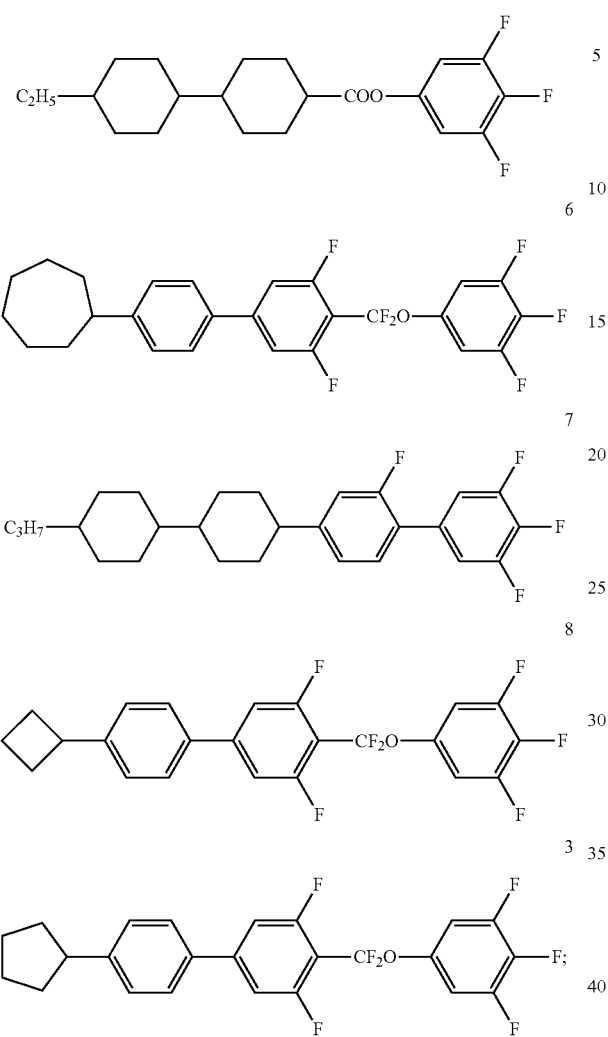
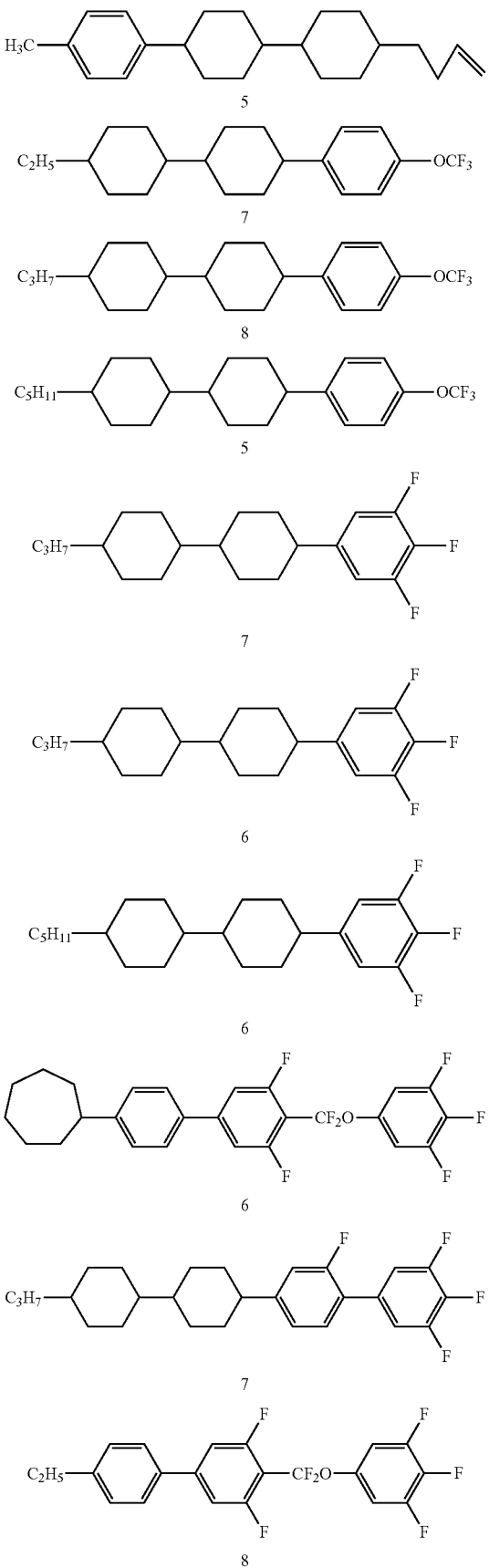
the liquid crystal mixture f comprises or consists of the following components in the respective parts by weight thereof:

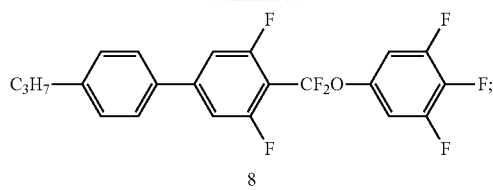
8
the liquid crystal mixture g comprises or consists of the following components in the respective parts by weight thereof:
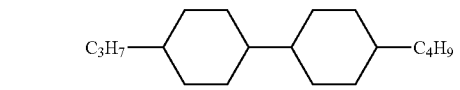
12
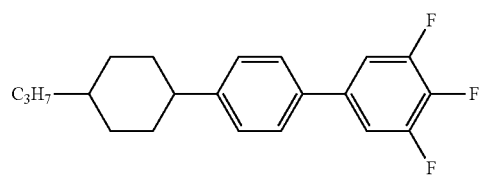
6
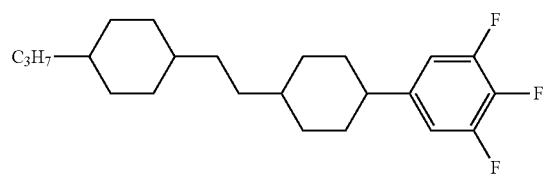
9
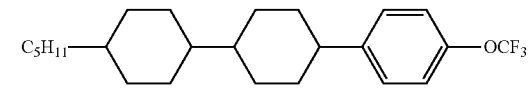
5
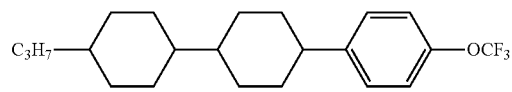
4
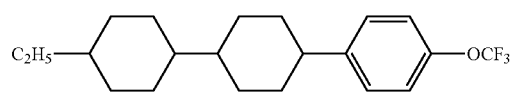
8
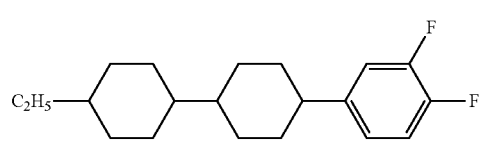
8
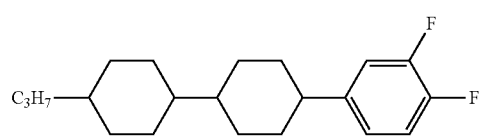
5
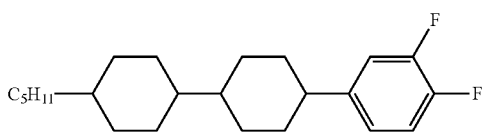
3
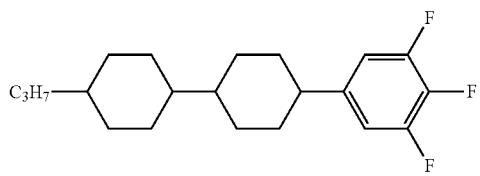
6
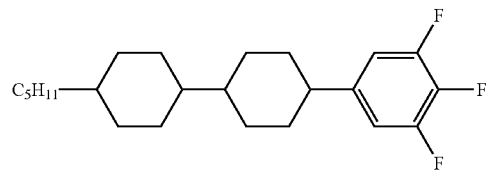
6
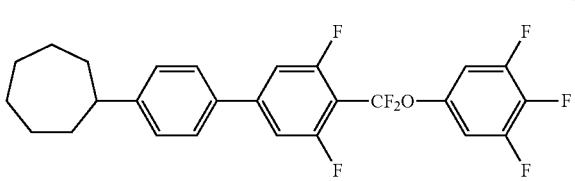
6
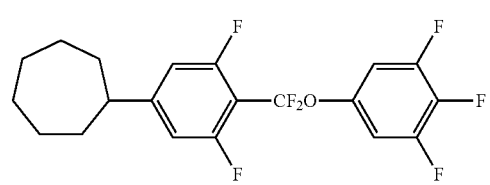
4
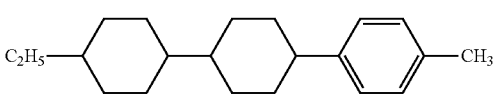
5
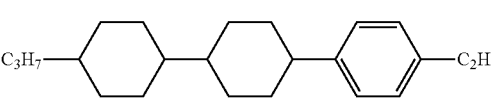
5
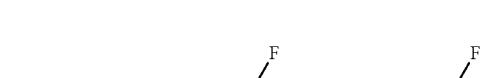
5
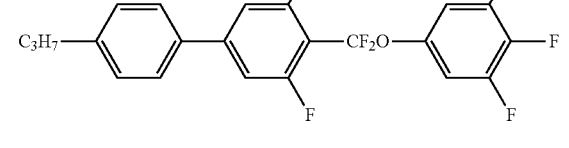
3
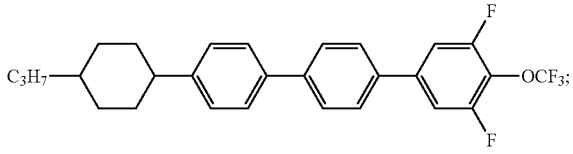
the liquid crystal mixture h comprises or consists of the following components in the respective parts by weight thereof:
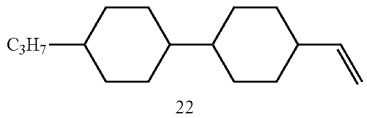
22

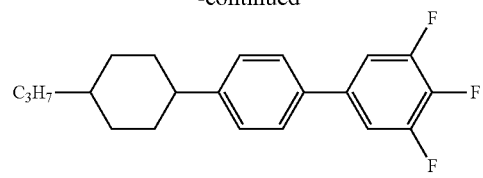
6
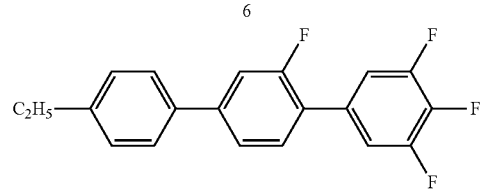
9
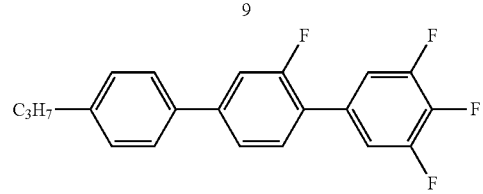
5
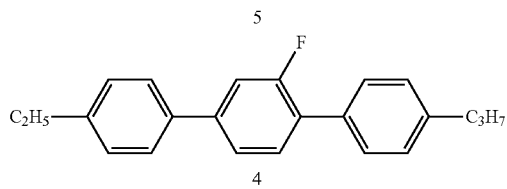
4
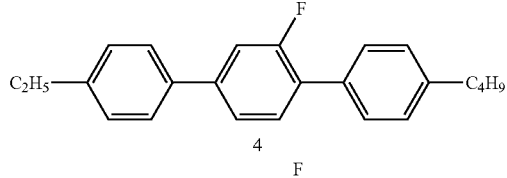
4
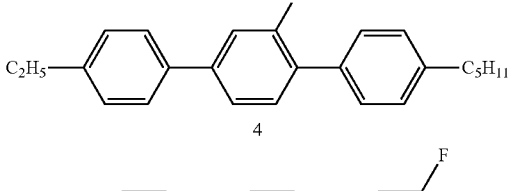
4
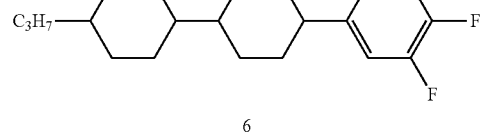
6
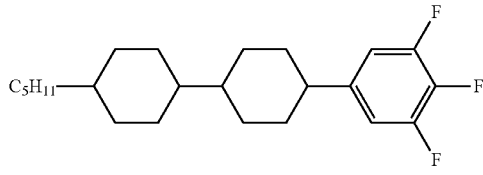
6
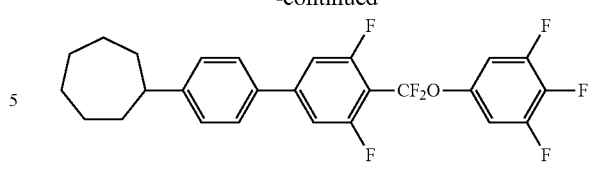
6
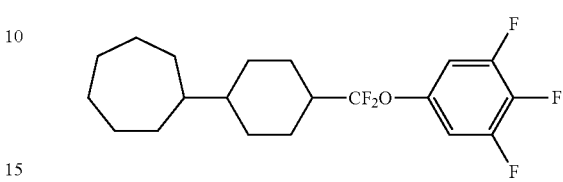
4
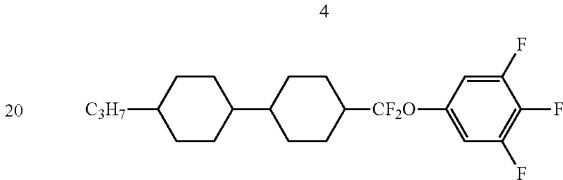
5
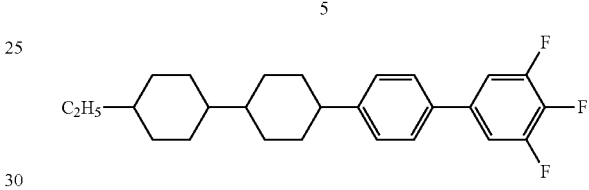
5
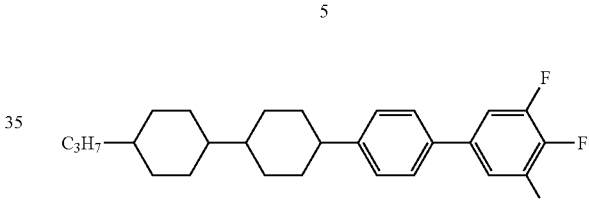
6
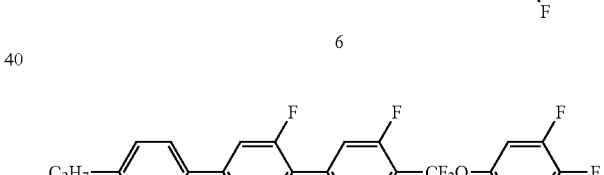
4
4
* * * * *